United States Patent
Boehnke et al.

(10) Patent No.: US 12,194,055 B2
(45) Date of Patent: Jan. 14, 2025

(54) SOLUTE CARRIER FAMILY 46 MEMBER 3 (SLC46A3) AS MARKER FOR LIPID-BASED NANOPARTICLE CANCER THERAPY AND DIAGNOSTICS

(71) Applicants: MASSACHUSETTS INSTITUTE OF TECHNOLOGY, Cambridge, MA (US); DANA-FARBER CANCER INSTITUTE, INC., Boston, MA (US)

(72) Inventors: Natalie Boehnke, Cambridge, MA (US); Joelle Payne Straehla, Cambridge, MA (US); Angela Koehler, Cambridge, MA (US); Paula Hammond, Cambridge, MA (US)

(73) Assignees: MASSACHUSETTS INSTITUTE OF TECHNOLOGY, Cambridge, MA (US); DANA-FARBER CANCER INSTITUTE, INC., Boston, MA (US)

( * ) Notice: Subject to any disclaimer, the term of this patent is extended or adjusted under 35 U.S.C. 154(b) by 235 days.

(21) Appl. No.: 17/582,594

(22) Filed: Jan. 24, 2022

(65) Prior Publication Data
US 2022/0233576 A1 Jul. 28, 2022

Related U.S. Application Data

(60) Provisional application No. 63/248,438, filed on Sep. 25, 2021, provisional application No. 63/170,874, filed on Apr. 5, 2021, provisional application No. 63/140,315, filed on Jan. 22, 2021.

(51) Int. Cl.
| | |
|---|---|
| A61K 31/7105 | (2006.01) |
| A61K 9/127 | (2006.01) |
| A61K 9/16 | (2006.01) |
| A61K 38/46 | (2006.01) |
| A61K 45/06 | (2006.01) |
| A61P 35/00 | (2006.01) |
| C12N 15/113 | (2010.01) |
| C12Q 1/6886 | (2018.01) |
| G01N 33/574 | (2006.01) |

(52) U.S. Cl.
CPC ........ *A61K 31/7105* (2013.01); *A61K 9/1271* (2013.01); *A61K 9/1617* (2013.01); *A61K 9/1635* (2013.01); *A61K 9/1647* (2013.01); *A61K 38/465* (2013.01); *A61K 45/06* (2013.01); *A61P 35/00* (2018.01); *C12N 15/1135* (2013.01); *C12Q 1/6886* (2013.01); *G01N 33/574* (2013.01); *C12N 2320/34* (2013.01); *C12Q 2600/106* (2013.01); *C12Q 2600/158* (2013.01)

(58) Field of Classification Search
CPC .............. A61K 31/7105; A61K 9/1271; A61K 9/1617; A61K 9/1635; A61K 9/1647; A61K 38/465; A61K 45/06; A61P 35/00; C12N 15/1135; C12N 2320/34; C12Q 1/6886; C12Q 2600/106; C12Q 2600/158; G01N 33/574

See application file for complete search history.

(56) References Cited

U.S. PATENT DOCUMENTS
2018/0064679 A1 3/2018 Pierce et al.

FOREIGN PATENT DOCUMENTS
WO 2020157508 A1 8/2020

OTHER PUBLICATIONS

Qing Zhao et al, Increased expression of SLC46A3 to oppose the progression of hepatocellular carcinoma and its effect on sorafenib therapy, Biomedicine & Pharmacotherapy, vol. 114, 2019, 108864, (Year: 2019).*

Krista Kinneer et al., SLC46A3 as a Potential Predictive Biomarker for Antibody-Drug Conjugates Bearing Noncleavable Linked Maytansinoid and Pyrrolobenzodiazepine Warheads. Clin Cancer Res Dec. 15, 2018; 24 (24): 6570-6582. https://doi.org/10.1158/1078-0432.CCR-18-1300 (Year: 2018).*

Kevin J. Hamblett et al., SLC46A3 Is Required to Transport Catabolites of Noncleavable Antibody Maytansine Conjugates from the Lysosome to the Cytoplasm. Cancer Res Dec. 15, 2015; 75 (24): 5329-5340. https://doi.org/10.1158/0008-5472.CAN-15-1610 (Year: 2015).*

Li, Q., Shu, Y. Role of solute carriers in response to anticancer drugs. Mol and Cell Ther 2, 15 (2014). https://doi.org/10.1186/2052-8426-2-15 (Year: 2014).*

Arati Sharma, SubbaRao V Madhunapantula & Gavin P Robertson (2012) Toxicological considerations when creating nanoparticle-based drugs and drug delivery systems, Expert Opinion on Drug Metabolism & Toxicology, 8:1, 47-69, DOI: 10.1517/17425255.2012.637916 (Year: 2011).*

Tissue Expression of SLC46A3—Summary—the Human Protein Atlas. www.proteinatlas.org/ENSG00000139508-SLC46A3/tissue. (Year: 2024).*

Tang et al. ggfortify: Unified Interface to Visualize Statistical Results of Popular R Packages. R. J. 8, 474-485 (2016).

(Continued)

*Primary Examiner* — Stephen T Kapushoc
*Assistant Examiner* — Amanda M Zahorik
(74) *Attorney, Agent, or Firm* — MCDONNELL BOEHNEN HULBERT & BERGHOFF LLP

(57) ABSTRACT

SLC46A3 has been identified as a lipid-based nanoparticle-specific biomarker predictive of nanoparticle-cancer cell affinity. SLC46A3 has a strong inverse association with lipid-based nanoparticle uptake across multiple nanoparticle formulations. Tissues with decreased expression levels of SLC46A3 have a greater uptake of lipid-based nanoparticles. The inverse relationship of SLC46A3 expression in tumor tissue and affinity for lipid-based nanoparticles has therapeutic and diagnostic implications, including cancer therapy and diagnosis, and identification of patients most likely to benefit from a lipid-based nanotherapeutic for improved stratification in clinical trials.

9 Claims, 19 Drawing Sheets

Specification includes a Sequence Listing.

(56) References Cited

OTHER PUBLICATIONS

Tran et al. Cancer nanomedicine: a review of recent success in drug delivery. Clin. Transl. Med. 6, 1-21 (2017).
Tsuchikama et al. Antibody-drug conjugates: recent advances in conjugation and linker chemistries. Protein Cell 9, 33-46 (2018).
Tsui et al., CRISPR-Cas9 screens identify regulators of antibody-drug conjugate toxicity. Nat. Chem. Biol. 15, 949-958 (2019).
Voigt et al. Differential uptake of nanoparticles by endothelial cells through polyelectrolytes with affinity for caveolae. Proc. Natl. Acad. Sci. U.S.A. 111, 2942-2947 (2014).
Von Mering et al. String: a database of predicted functional associations between proteins. Nucleic Acids Res. 31, 258-261 (2003).
Wickham. ggplot2: Elegant Graphics for Data Analysis. Use R, 1-212 (2009).
Wilhelm et al. Analysis of nanoparticle delivery to tumours. Nat. Rev. Mater. 1, 16014 (2016).
Yokoi et al. "Serum biomarkers for personalization of nanotherapeutics-based therapy in different tumor and organ microenvironments". Cancer Lett. 345(1):48-55 (2014).
Youn et al. Perspectives on the past, present, and future of cancer nanomedicine. Adv. Drug Deliver. Rev. 130, 3-11 (2018).
Yu et al., High-throughput identification of genotype-specific cancer vulnerabilities in mixtures of barcoded tumor cell lines. Nat. Biotechnol. 34, 419-423 (2016).
Zhao et al., Increased expression of SLC46A3 to oppose the progression of hepatocellular carcinoma and its effect on sorafenib therapy. Biomed. Pharmacother. 114, 108864 (2019).
International Search Report and Written Opinion for PCT/US2022/013491 mailed May 10, 2022.
Aberg et al. Reply to 'The interface of nanoparticles with proliferating mammalian cells'. Nat. Nanotechnol. 12, 600-603 (2017).
Adelmann et al. MFSD12 mediates the import of cysteine into melanosomes and lysosomes. Nature 588, 699-704 (2020).
Ashburner et al., Gene Ontology: tool for the unification of biology. Nat. Genet. 25, 25-29 (2000).
Barretina et al. The Cancer Cell Line Encyclopedia enables predictive modelling of anticancer drug sensitivity (vol. 483, p. 603, 2012). Nature 492, 290-290 (2012).
Behzadi et al. Cellular uptake of nanoparticles: journey inside the cell. Chem. Soc. Rev. 46, 4218-4244 (2017).
Berg et al. Labeling Antibodies Using N-Hydroxysuccinimide (NHS)-Fluorescein. Cold Spring Harb. Protoc. 3, 229-231 (2019).
Boehnke et al. "Massively parallel pooled screening reveals genomic determinants of nanoparticle delivery". Science 377(6604):eabm5551 (2022).
Boehnke et al. "Power in Numbers: Harnessing cominatorial and integrated screens to advance nanomedicine". JACS Au. 2(1): 12-21 (Jan. 2022).
Boehnke et al. Electrostatic Conjugation of Nanoparticle Surfaces with Functional Peptide Motifs. Bioconjug. Chem. 31, 2211-2219 (2020).
Boehnke et al. Theranostic Layer-by-Layer Nanoparticles for Simultaneous Tumor Detection and Gene Silencing. Angew. Chem. Int. Ed. Engl. 59, 2776-2783 (2020).
Carbon et al., The Gene Ontology resource: enriching a GOld mine. Nucleic Acids Res. 49, D325-D334 (2021).
Cheng et al. Meta-Analysis of Nanoparticle Delivery to Tumors Using a Physiologically Based Pharmacokinetic Modeling and Simulation Approach. ACS Nano 14, 3075-3095 (2020).
Correa et al. Highly Scalable, Closed-Loop Synthesis of Drug-Loaded, Layer-by-Layer Nanoparticles. Adv. Funct. Mater. 26, 991-1003 (2016).
Correa et al. Solution Conditions Tune and Optimize Loading of Therapeutic Polyelectrolytes into Layer-by-Layer Functionalized Liposomes. ACS Nano 13, 5623-5634 (2019).
Correa et al., Tuning Nanoparticle Interactions with Ovarian Cancer through Layer-by-Layer Modification of Surface Chemistry. ACS Nano 14, 2224-2237 (2020).
Corsello et al., Discovering the anticancer potential of non-oncology drugs by systematic viability profiling. Nat. Cancer 1, 235-248 (2020).
Dahlman et al., Barcoded nanoparticles for high throughput in vivo discovery of targeted therapeutics. Proc. Natl. Acad. Sci. U.S.A. 114, 2060-2065 (2017).
Decher. Fuzzy nanoassemblies: Toward layered polymeric multicomposites. Science 277, 1232-1237 (1997).
Deng et al. Layer-by-Layer Nanoparticles for Systemic Codelivery of an Anticancer Drug and siRNA for Potential Triple-Negative Breast Cancer Treatment. ACS Nano 7, 9571-9584 (2013).
Dreaden et al. Bimodal Tumor-Targeting from Microenvironment Responsive Hyaluronan Layer-by-Layer (LbL) Nanoparticles. ACS Nano 8, 8374-8382 (2014).
Dreaden et al. Tumor-Targeted Synergistic Blockade of MAPK and PI3K from a Layer-by-Layer Nanoparticle. Clin. Cancer Res. 21, 4410-4419 (2015).
Frohlich. The role of surface charge in cellular uptake and cytotoxicity of medical nanoparticles. Int. J. Nanomed. 7, 5577-5591 (2012).
Ghandi et al. Next-generation characterization of the Cancer Cell Line Encyclopedia. Nature 569, 503-508 (2019).
Hamblett et al. SLC46A3 Is Required to Transport Catabolites of Noncleavable Antibody Maytansine Conjugates from the Lysosome to the Cytoplasm. Cancer Res. 75, 5329-5340 (2015).
Horikoshi et al. ggfortify: Data Visualization Tools for Statistical Analysis Results. https://CRAN.R-project.org/package=ggfortify (2016).
Jin et al., A metastasis map of human cancer cell lines. Nature 588, 331-336 (2020).
Kim et al. Role of cell cycle on the cellular uptake and dilution of nanoparticles in a cell population. Nat. Nanotechnol. 7, 62-68 (2012).
Kinneer et al., SLC46A3 as a Potential Predictive Biomarker for Antibody-Drug Conjugates Bearing Noncleavable Linked Maytansinoid and Pyrrolobenzodiazepine Warheads. Clin. Cancer Res. 24, 6570-6582 (2018).
Li et al., Mechanisms of Acquired Resistance to Trastuzumab Emtansine in Breast Cancer Cells. Mol. Cancer Ther. 17, 1441-1453 (2018).
Martin et al. GOToolBox: functional analysis of gene datasets based on Gene Ontology. Genome Biol. 5, R101 (2004).
Mitchell et al. Engineering precision nanoparticles for drug delivery. Nat. Rev. Drug. Discov. 20, 101-124 (2020).
Morton et al. The architecture and biological performance of drug-loaded LbL nanoparticles. Biomaterials 34, 5328-5335 (2013).
Nogrady. How cancer genomics is transforming diagnosis and treatment. Nature 579, S10-S11 (2020).
Oommen et al. Multifunctional Hyaluronic Acid and Chondroitin Sulfate Nanoparticles: Impact of Glycosaminoglycan Presentation on Receptor Mediated Cellular Uptake and Immune Activation. ACS Appl. Mater. Inter. 8, 20614-20624 (2016).
Panet et al., The interface of nanoparticles with proliferating mammalian cells. Nat. Nanotechnol. 12, 598-600 (2017).
Poon et al. A framework for designing delivery systems. Nat. Nanotechnol. 15, 819-829 (2020).
Poon et al. Elimination Pathways of Nanoparticles. ACS Nano 13, 5785-5798 (2019).
R Core Team. R: A language and envrionemnt for statistical computing. R Foundation for Statistical Compouting. https://www.R-project.org/.
Rees et al. The origin of heterogeneous nanoparticle uptake by cells. Nat. Commun. 10 (2019).
Rejman et al. Size-dependent internalization of particles via the pathways of clathrin-and caveolae-mediated endocytosis. Biochem. J. 377, 159-169 (2004).
Rosenblum et al. "Progress and challenges towards targeted delivery of cancer therapeutics". Nat Commun. 9(1):1410 (2018).
Saravanakumar et al. Polysaccharide-Based Nanoparticles: A Versatile Platform for Drug Delivery and Biomedical Imaging. Curr. Med. Chem. 19, 3212-3229 (2012).
Shamay et al. P-selectin is a nanotherapeutic delivery target in the tumor microenvironment. Sci. Transl. Med. 8, 345 (2018).
Shi et al. Cancer nanomedicine: progress, challenges and opportunities. Nat. Rev. Cancer 17, 20-37 (2017).

(56) References Cited

OTHER PUBLICATIONS

Snel et al. String: a web-server to retrieve and display the repeatedly occurring neighbourhood of a gene. Nucleic Acids Res. 28, 3442-3444 (2000).
Stephens. False discovery rates: a new deal. Biostatistics 18, 275-294 (2017).
Stern et al. NCL Method GTA-12. NCI Hub, doi:10.17917/YPTH-N396.
Straehla et al. "Development of a multi-omic, pooled cancer cell screen for nanoparticle delivery". Proceedings of the American Association for Cancer Research Meeting 2021. Poster Abstract. Cancer Res (2021) 81 (13_Supplement): 309 (Jul. 2021).
Suk et al. PEGylation as a strategy for improving nanoparticle-based drug and gene delivery. Adv. Drug Deliver. Rev. 99, 28-51 (2016).
Szklarczyk et al. String v11: protein-protein association networks with increased coverage, supporting functional discovery in genome-wide experimental datasets. Nucleic Acids Res. 47, D607-D613 (2019).

\* cited by examiner

Fig. 1B-D
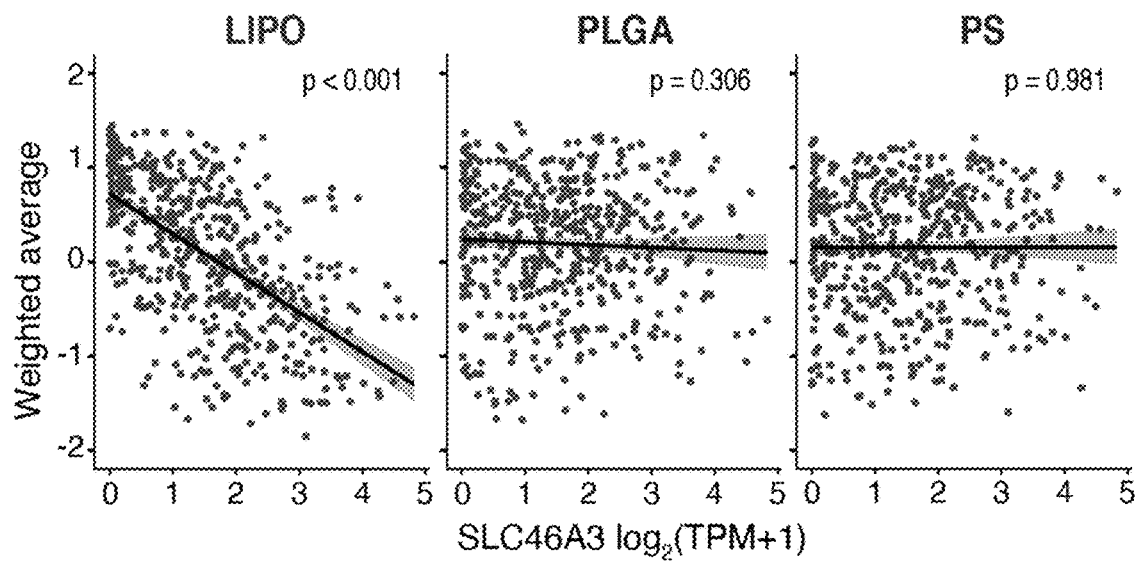
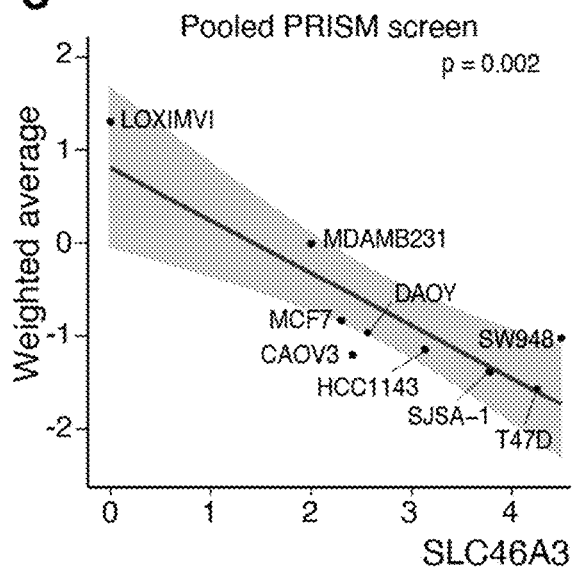
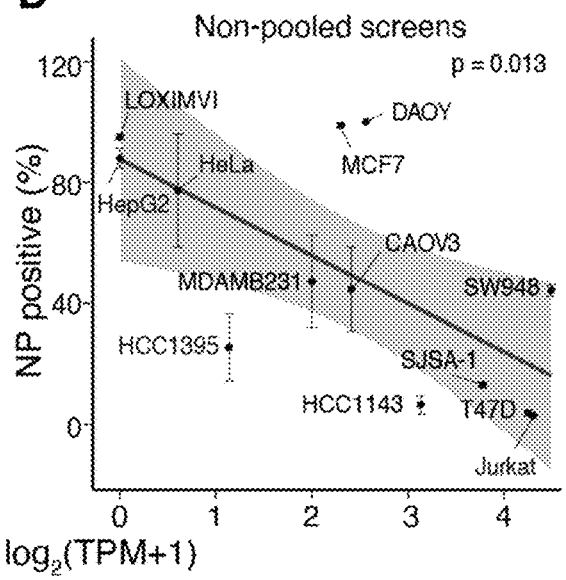

Fig. 2A-B
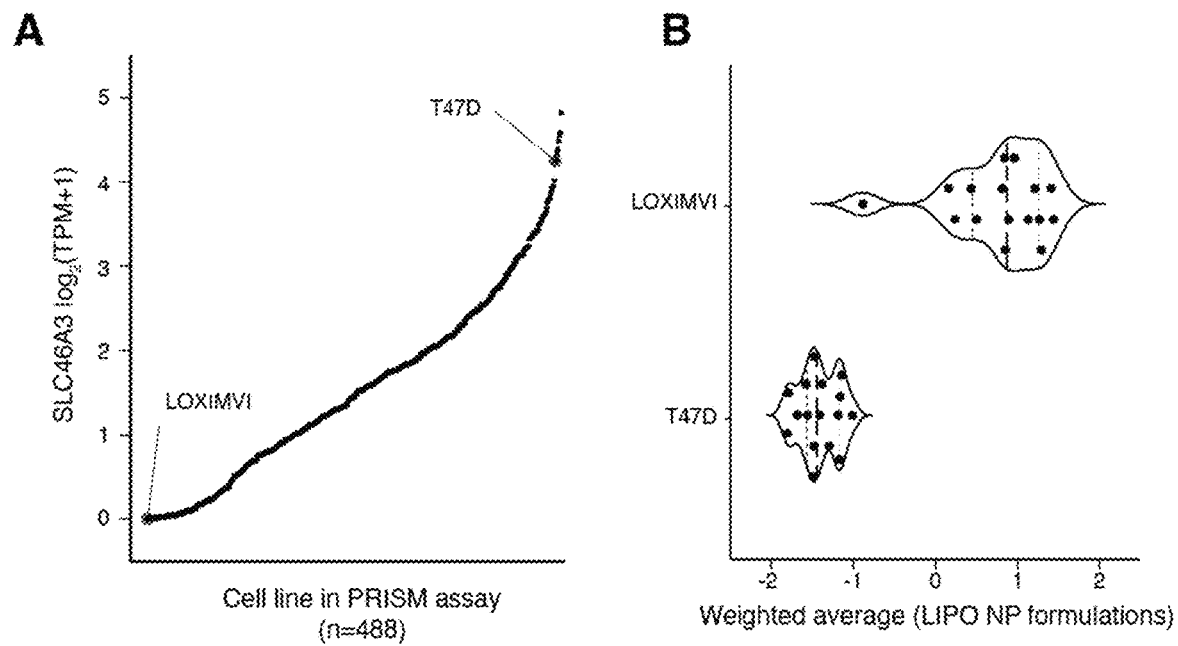

Fig. 2D-E
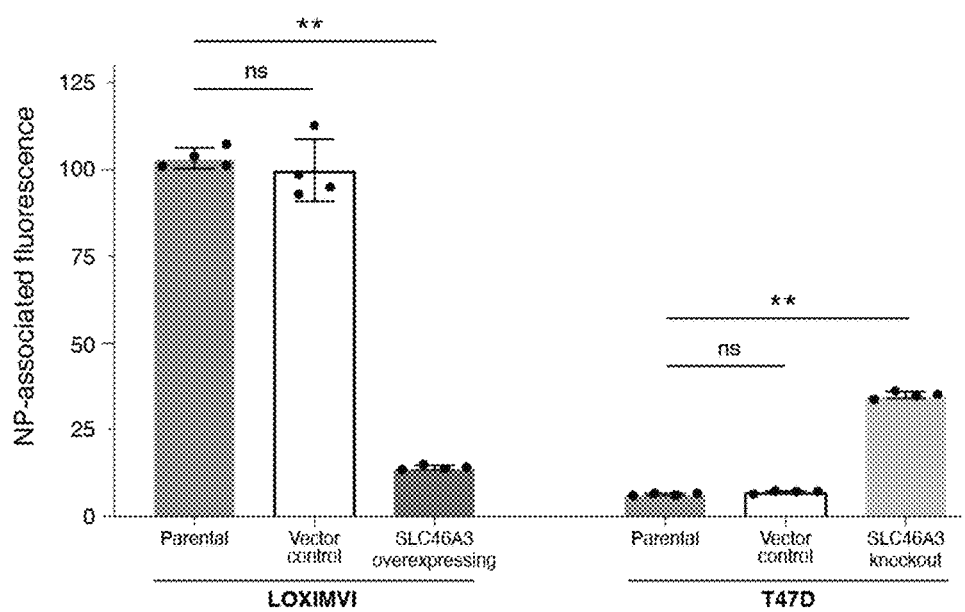
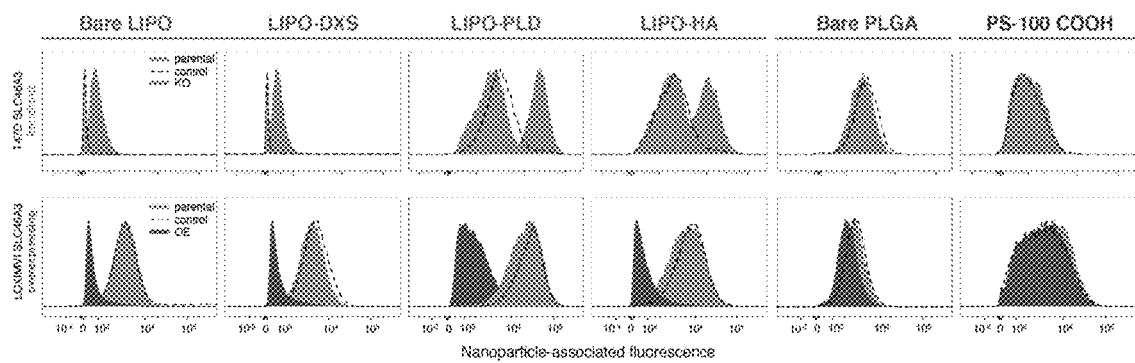

Fig. 4A-B
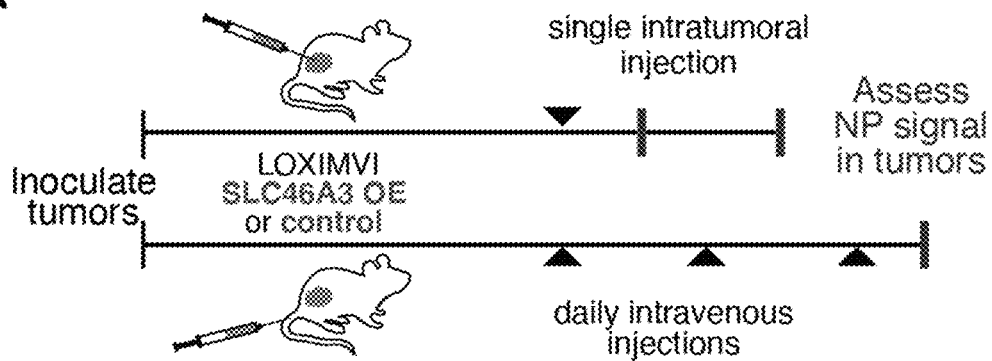
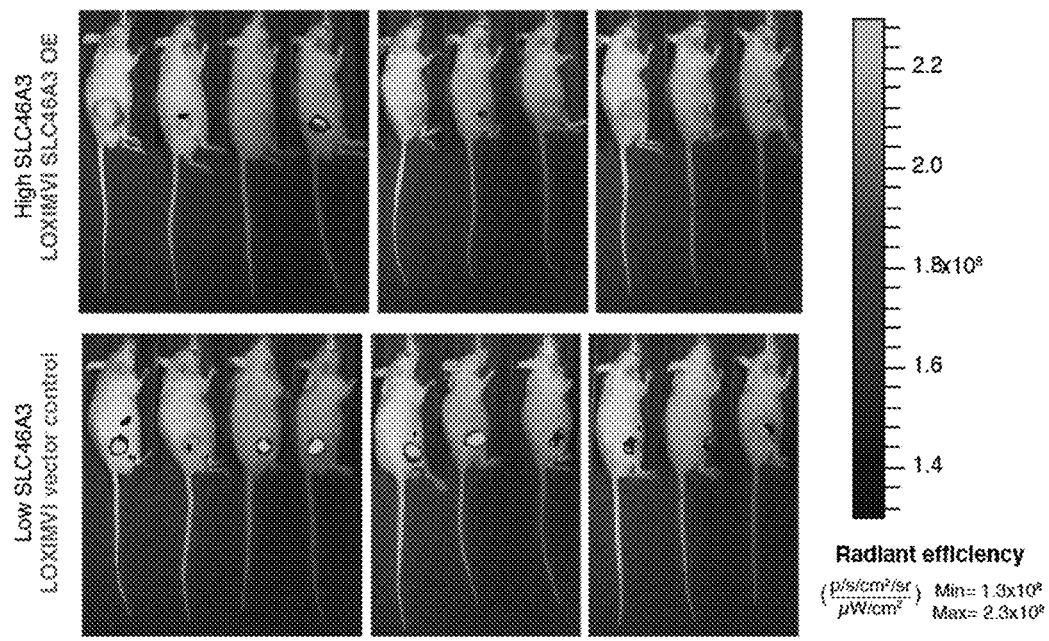

Fig. 4C-D
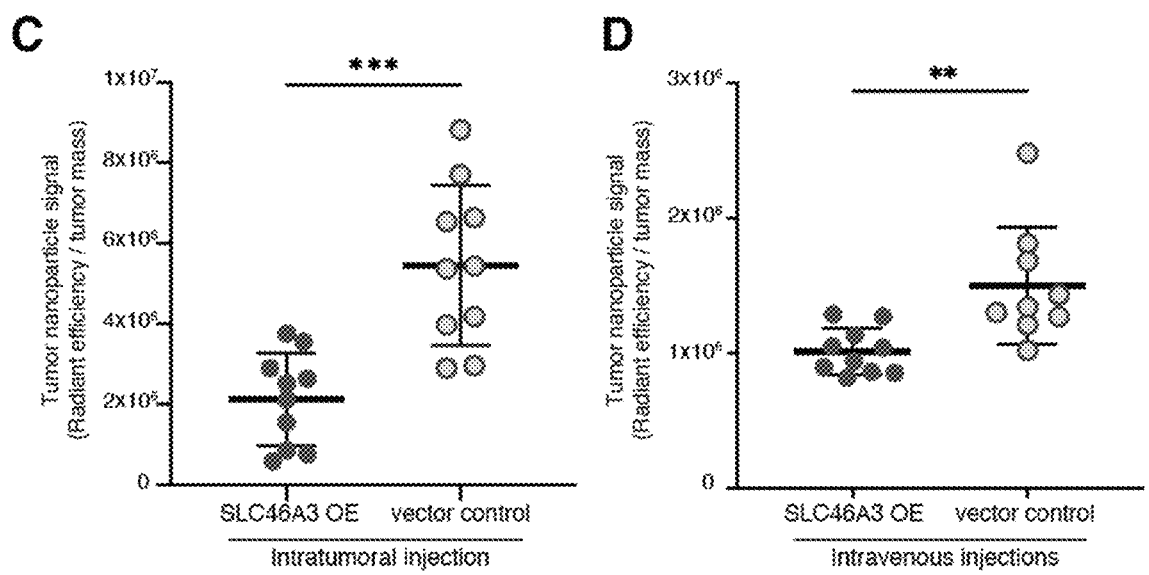

Fig. 5B-C
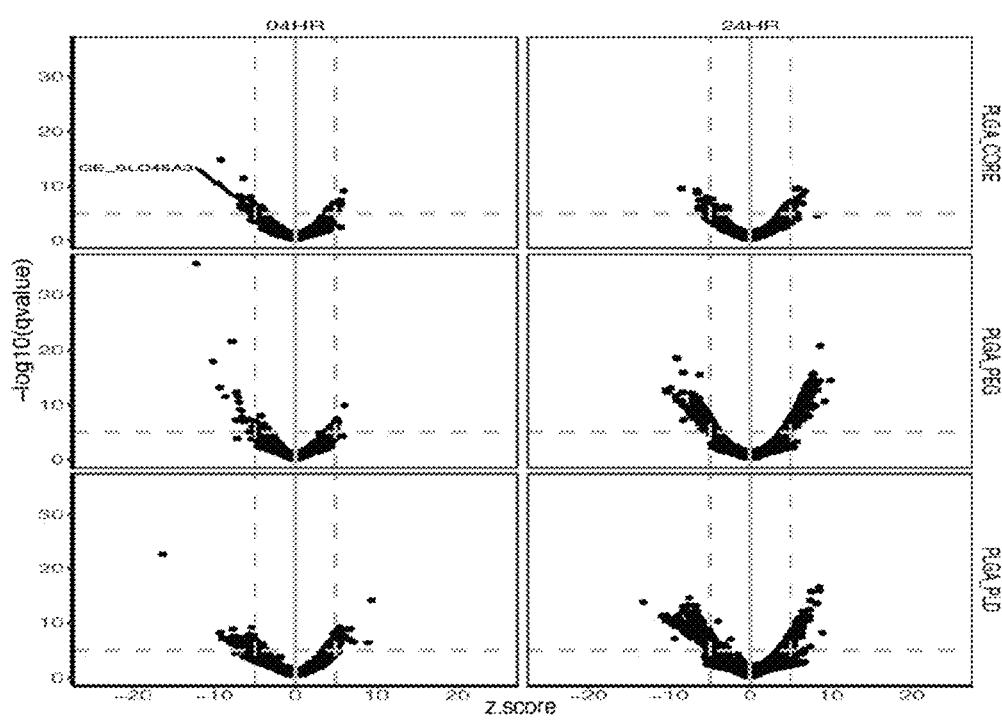
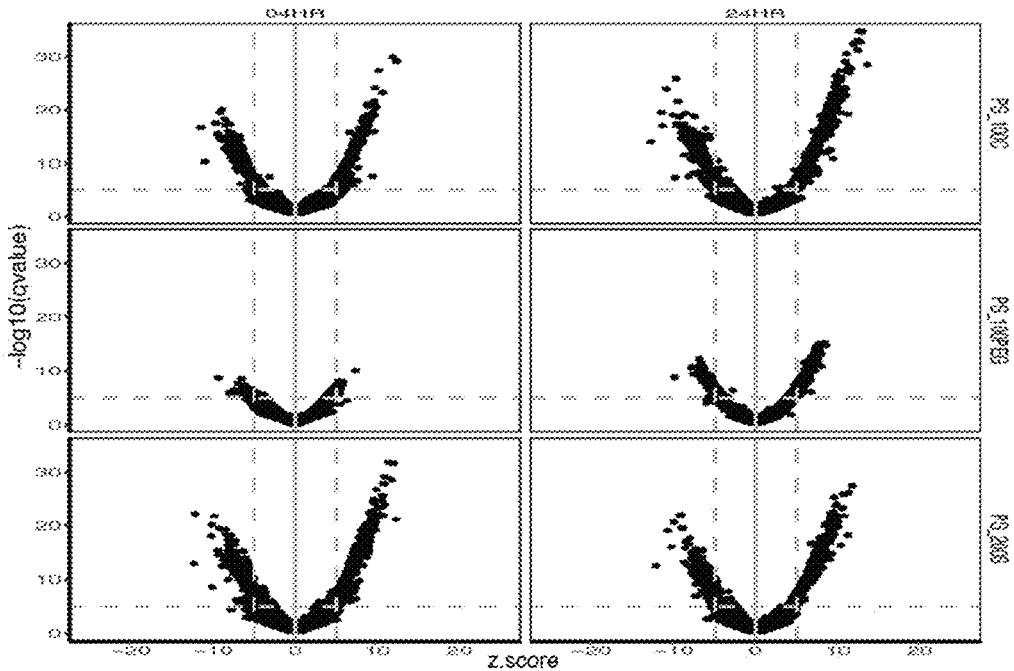

Fig. 9A-C
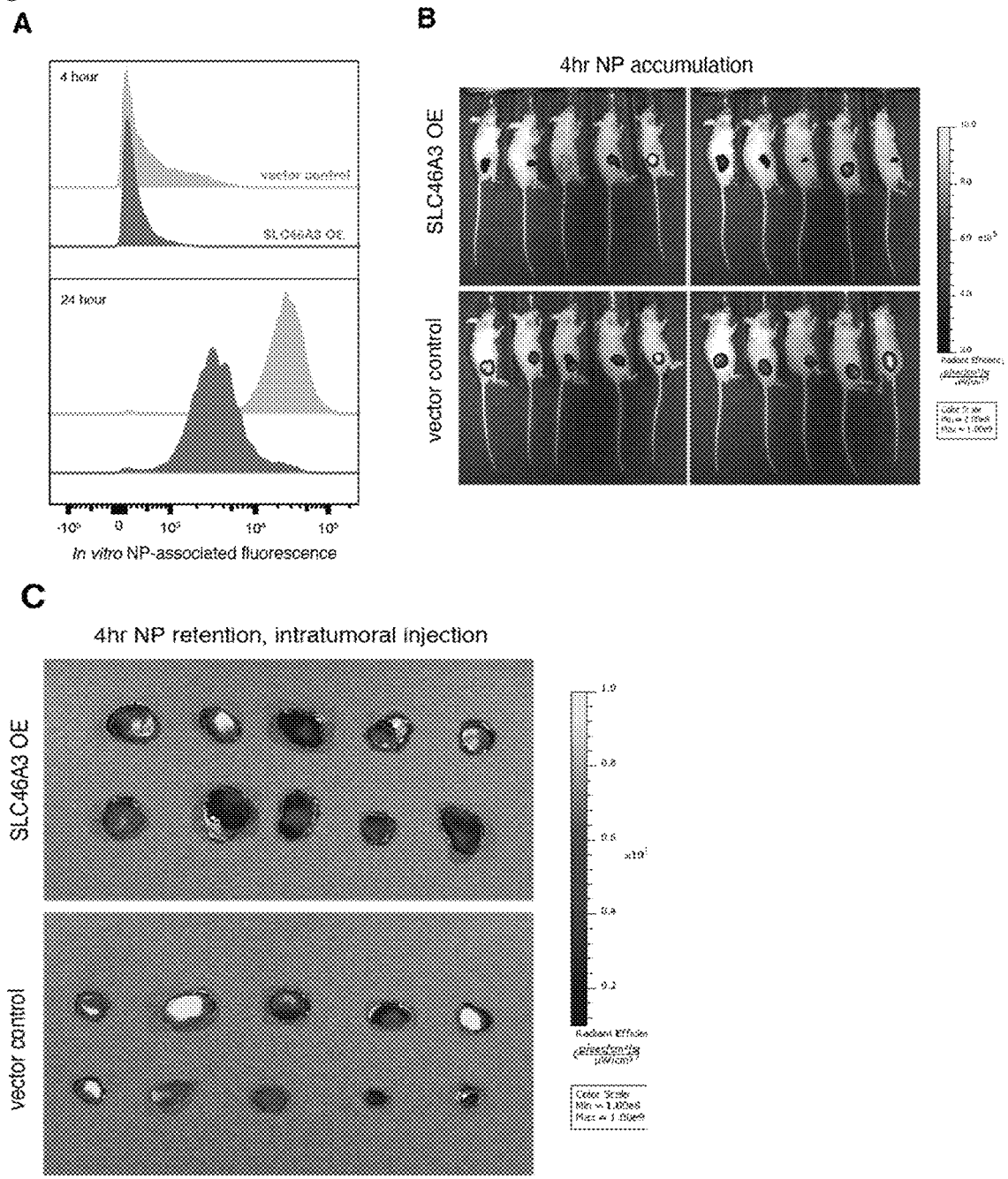

Fig. 9D-E
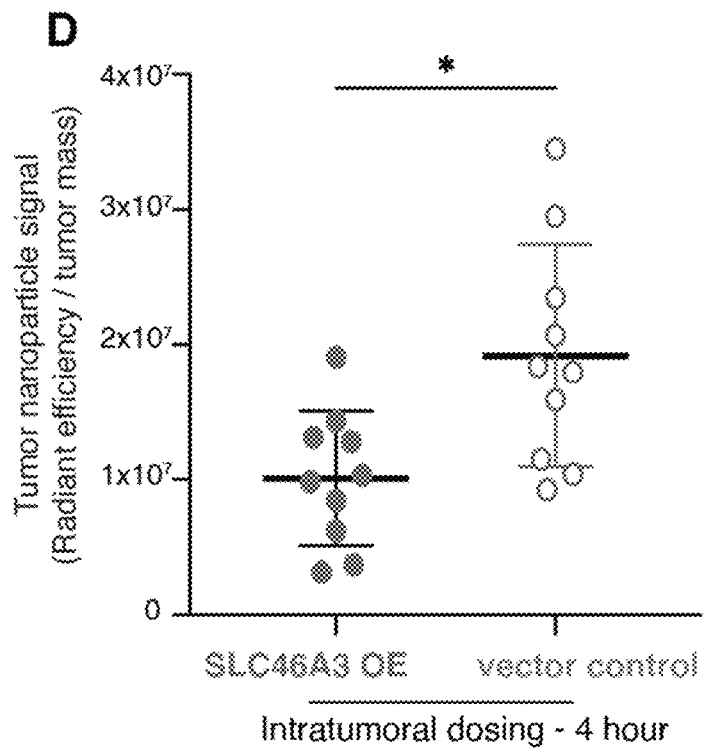
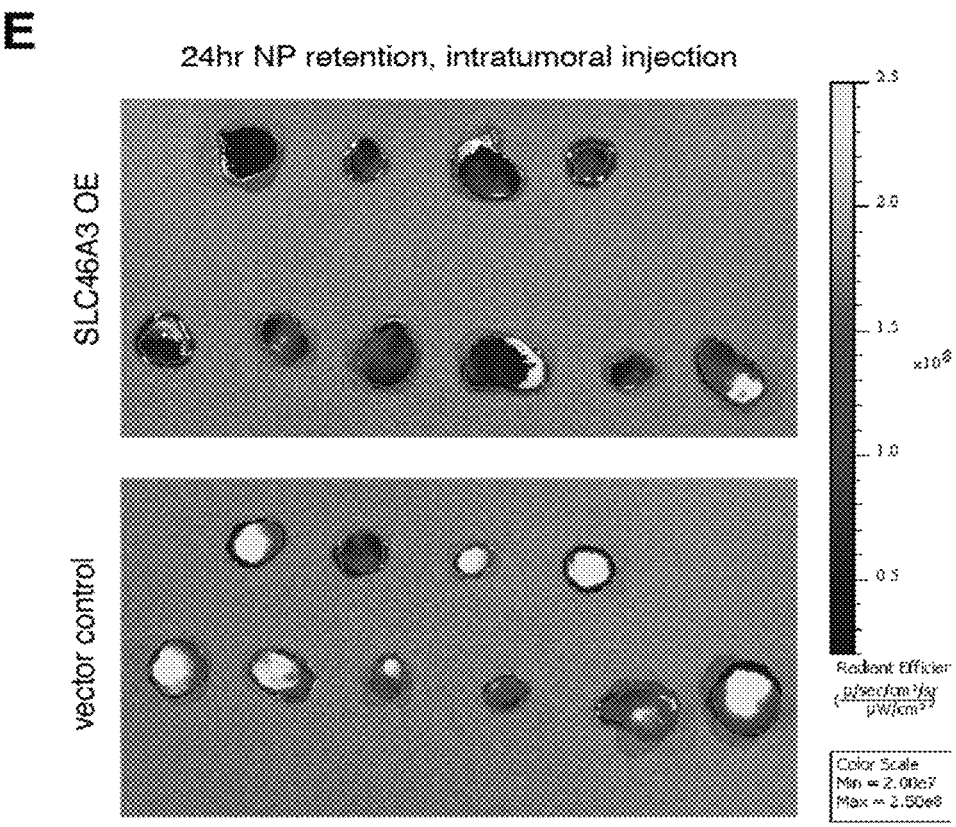

Fig. 9F-G
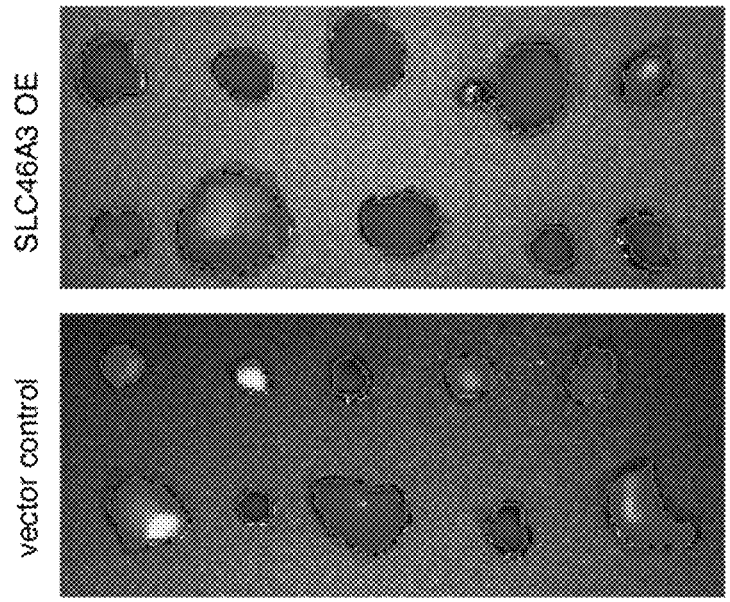
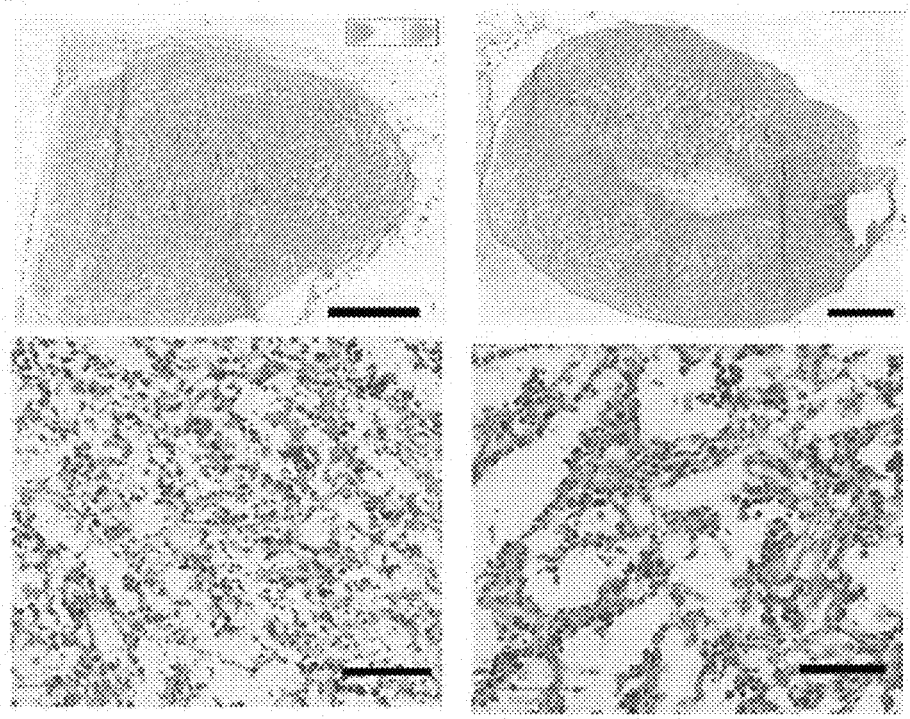

SEQUENCE LISTING

<160> NUMBER OF SEQ ID NOS: 12

<210> SEQ ID NO 1
<211> LENGTH: 18907
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| ggacagcgat | gctcagctgg | ctgcggccga | gtcatcgcct | agcgctggca | gggccgctga | 60 |
| ccgaccgacg | gaggcgccga | ttggccgatt | gtccactgcg | cagaaggagc | agctgctccg | 120 |
| cgccccgccg | cgccgcgctg | aggccgaggt | ccgcagggcc | gcggggaagc | cgagggctgc | 180 |
| cggagaaccc | tgcaggtgtc | actcgggacg | cggaagtgcg | cttgccgagg | tttgctttac | 240 |
| aatacgcttg | agactccccg | acaagcgtaa | tttggtcgag | ttcgacggga | aagtactctc | 300 |
| cccacccag | cgccggccgc | gtagtccgag | gttactgtcc | ccggcgcgtc | ctctgttgcc | 360 |
| ccagtccaga | ggctgccctt | gaacccgggc | gcgcacgagc | gcagggcatc | cgaggcgaca | 420 |
| gcccctggca | cggcccgacc | tgtacccagc | ctggcaggaa | gactgtaatc | gtggggtgag | 480 |
| ttaaaaataa | ggccctttcg | attgggagct | gcttttaaa | acgcccctc | cctgtccgtt | 540 |
| tttaatacgc | agcaaaataa | caataacaat | tgtgcaactg | tcgcttccca | aaaggaacct | 600 |
| cattgttgaa | cttacgaaaa | atcagttggc | aatatacagt | gtgggaactg | tactgtgatc | 660 |
| attggctaac | caagatgggt | gacagtttat | gatttcaaag | actcaaaggc | ggcttgagtc | 720 |
| ctacaatgtc | ctactcataa | aaatggaaag | catggcagcc | tcaggttgtt | acagagtact | 780 |
| ctactccaaa | gtaaaagtta | ttctctgaga | aagtgcttac | tgccttttct | gttctctagt | 840 |
| ttgcttgttt | aaacatttac | tccacaaaat | tgctcaaact | tacccatctt | tgaatatcta | 900 |
| gcctctggga | tgagacagat | gatctttctc | cgttttcact | ttttatagaa | tacagctacc | 960 |
| tacccaggca | atatgaagat | tttatttgta | gaacctgcca | ttttccttag | tgcatttgct | 1020 |
| atgactttga | ccggtccact | gacaacgcaa | tatgtttatc | ggagaatatg | ggaagaaact | 1080 |
| ggcaactaca | cttttttcatc | tgatagcaat | atttctgagt | gtgaaaaaa | caaaagcagc | 1140 |
| ccaattttg | cattccagga | ggtaagaaat | tacaatatcc | atagtattta | ataaaatggg | 1200 |
| aatgtatacc | gggctttgag | ttaaagagga | ccgtgaactc | atcatccatt | ggtctctcta | 1260 |
| gggcggccat | caaagtccta | aatcccaaac | ctaatggcct | ttactgggaa | ctcacctcat | 1320 |
| ttgaagtttc | ctgacaccctt | tcaaatctgc | ctcttcttct | taaaacaccc | tcctgctctg | 1380 |
| tgacactagc | tcttctcctt | tctctcggaa | aatttcacca | cagtgtcatc | tcttctgtgg | 1440 |
| ctgtctcctt | gctttgtcct | aaaaaaaaa | aaaaaaaa | aaaagtctg | aaaattgggg | 1500 |
| cagggcaggc | tggaatgagc | tacttggtgg | acaggggtgg | ctgaaacatg | gtgtttctgt | 1560 |
| ctctcacttg | ctctattctt | ccccaatcct | tttactgttt | ctgcatgtcc | cagctttcag | 1620 |
| ggactctaga | aagtggccca | tcactgaaga | ttgtgagcca | gtgtctgtca | cagggtgggg | 1680 |
| tggaggagca | tttattattt | ggtggtggta | tcaaatcagc | cttggctctc | acgtgttgag | 1740 |
| gagcagctgt | gtggggacat | ctggagtggg | gagtacccac | cgttgacacc | aaagatgttt | 1800 |
| agccagatat | taaggaggct | tcttcctcc | ctctccagca | atctccccag | ttttttttgtg | 1860 |
| tgtaaaacag | gaggcaggca | cttcaccatt | ctcctggtcc | cttgggcagt | ttttgacaaa | 1920 |
| agtctaccat | ttcaaaatgc | aaagagatag | tatccaggtt | tggaaatttt | ttttttttc | 1980 |
| ctacaatgcc | tcaaaaacaa | atcacacctg | taaactctaa | actcttcttc | tgggggatat | 2040 |

-continued

```
tttgtgattg taaaggagtg gtgctgcctt cccagtgaaa gatgaaatga attaaaagga    2100
attgagtcac ctcctgctgg ctctgtgagt ctctgtgact gggagaagag cctgagaagg    2160
aggaaatggc aaaccgcccc agaggcaagg ttctagcact tcccgaggtg tcaggtggaa    2220
ccttgctggg gtgaggttag gcaatttggc acaatcccta atcttactca tttcctcatt    2280
cccatgggaa acgttttctt gggagtgatt atttctgagc agcctggaag acatcaaggt    2340
tctggcgtag agtaaggtca taaaaaaaaa gggccctgag tctcacccag cggtcttatc    2400
tcccttcaag aatgtctcct aggtcattcc cgggagtgag aagcttcgat cggctcacag    2460
tttcttttg taagtgttta ttcatgcatt aaacaaatgt ttatcacaca ttatcctgtg    2520
gtgacaagga taagcaaaac ggctctgaac ccgagaagcc cagagtctct ctaggttgag    2580
aaaaacacac ataaacagaa tagagtttaa caaatcctct tagtttcaaa gttgggtcc    2640
tacagcaggg atgctcttca gatttcggct ctggagacgt tgttaatat acatacttga    2700
atcccatcct ggaacctcta acacagtgtt ttttaacctt gactgacat gggaatcacc    2760
tgaagtgttt tttattttat tttgtttatt atgtatttat gcatgtatgg tacttttga    2820
gacagggtct cattctgctg cccacgctgg agtggagtgg cgtggtaata gctcgctgca    2880
actttgaact cctaggctca agggatcctc tcacctcagc ctcctgagta gctgggacta    2940
caggcacgtg ccactacact cagctaattt ttgatttttt ttttttttt ttgtagagac    3000
agggtcttcc tctgtttccc aggctggcct tgaactcgtg gcctcaagtg agcctcctgt    3060
ctggtcctct caaagtgttg ggattacagg cgtgagccac cgtgcccggt cttatttat    3120
ttttttaatt gacagataat cattgtacat attcatggag tatacagtgg tgttttgata    3180
catacaatgt atagtgatca gatcaggcta attagcatat ccatcaactc agacatctct    3240
catttctttg tgttgggaac attcaatacc ctccttcttg ctatttgaaa ctatataaca    3300
tattactgtt aactgtagtc accctgtggt gctacagaac accagaactt attcctcctg    3360
tctagctgta attttgtatc ctttaacaaa tttcttctta caggctcatc aatttctgta    3420
tttgattctg tgctttcttt tggctgacct gtaggagcag gcccctggt tgcagtggga    3480
gggaccaggg aggagaggac aagaatgtct gggaaagtct gctgctcttg ccctcttgga    3540
ctgagggaag acgggccttg gtccagccag cttggtggct tctgcaacca tacaggggc    3600
aagtgttggc ccacctccag cctggcccag ctgctgagag cccctactg cccacagcag    3660
tggtctcatg tcaaagattt ttgccgaatt ttcaaattga cttttcatt tattgtttct    3720
taattggatt aatattcaag agaacctact actctagatc ccttcccta aagttggtgc    3780
tcttagacct ctgggaacca gaaccacccc taccctcac ctgccaccca cgctggagtg    3840
gtggcctact ctctgtttgc tccttaggac aaaggaacat ttttgtttcc caggaggcac    3900
caccatcgcc ttcagtgatt cattcaatga ctaaaaacgg tttacatctg ttttttaaat    3960
cagcttagca tttcccagta tacaaatggc acacactttt tatattgact ttggaaaata    4020
cagagcaatg gcaagcaaaa aatgttttaa gatcatgcaa aatttcttcc atcaagtaac    4080
tagtgtaatg attgacacat cttccaatct gtgtgtgtat gtcatctgtc attgtcattt    4140
tggtccttgg aagttgagtt tatcttactc ctcaggtcat gacatactac caccttttat    4200
tacttttat ttttattat ttgagatgga gtctcactgt gtcacccagg ctggagtgca    4260
atggcacaat ctcagctcat tgcaacctct gcctcccagg ttcaagcaat tcttctgcct    4320
cagcctccca agtagcggag actacaggcg tacgccacca cgcctggcta ttttttgtat    4380
```

```
ttttagtaga  gacagggttt  tgccatgttg  gccaggctgg  tctcaaactc  ctgacctcaa   4440
gtgatccgcc  caccttggcc  ccccaaagtg  ctaggattac  aggcgtgagc  caccgtgcct   4500
ggcctagttt  ttttaaattt  attttagag   acagggtctc  gctatgttgc  ccaggctggt   4560
ctcaaattcc  tgggcacaag  tgatgctccc  acctcggcct  cccacagtgc  tgggattata   4620
agcgtaagcc  accacactca  gccacggtat  gctaccatct  gtagacagtg  taagtctcct   4680
ctttcaattt  tatcttattt  taaattcttt  tatttagtaa  ataaaggaag  atgtttctca   4740
ctaatctatc  tgtgaagaca  taggtaaaaa  aaaaaaataa  gggcaacagc  caagctctcc   4800
ctaaataaag  gtttttttt   ttttttttg   tattttttgg  tagagacaga  gttttaccat   4860
gttggccaag  ctggtctcaa  actcctgacc  tcaagtgatc  ctcctgcctc  agcctcccaa   4920
aatatgagga  ttacaggcat  gagccaccac  gcccgaccaa  atctgaaaac  ttttttgatca  4980
ccacactta   ccacaagtgt  aaaattccac  acacaagtac  tcaatggcaa  ctgttttatg   5040
cacaaatttg  tttaaaatat  tgtataaaat  taccttcagg  ctgtatgtat  gaggtatata   5100
tgaaacataa  atgaattttg  tgtttaaatg  tgagtcccat  ccacaaggta  tctcattata   5160
tacatgcaaa  tatcccaaag  tctgaaaaaa  tccaaaatcg  gaaatacttc  tggtctcaag   5220
catttcagat  aagggatact  cagtctgcat  tgctttataa  actggatgaa  aatgtaagct   5280
ctattagtcc  cgcccatcca  ccagagattc  cccacccata  acctactggc  cacagggaaa   5340
aaagcatatg  caccatgata  tttttataca  cgttgtgtta  actactgtaa  acacattgtc   5400
ttctttatat  ttctttgcag  gaagttcaga  aaaaagtgtc  acgttttaat  ctgcagatgg   5460
acataagtgg  attaattcct  ggtctagtgt  ctacattcat  actttgtct   attagtgatc   5520
actacggacg  aaaattccct  atgattttgt  cttccgttgg  tgctcttgca  accagcgttt   5580
ggctctgttt  gctttgctat  tttgcctttc  cattccagct  tttgattgca  tctaccttca   5640
ttggtgcatt  ttgtggcaat  tataccacat  tttggggagc  ttgctttgcc  tatatagttg   5700
atcagtgtaa  agaacacaaa  caaaaaacaa  ttcgaatagc  tatcattgac  tttctacttg   5760
gacttgttac  tggactaaca  ggactgtcat  ctggctattt  tattagagag  ctaggttttg   5820
agtggtcgtt  tctaattatt  gctgtgtctc  ttgctgttaa  tttgatctat  attttatttt   5880
ttctcggaga  tccagtgaaa  gagtgttcat  ctcagaatgt  tactatgtca  tgtagtgaag   5940
gcttcaaaaa  cctattttac  cgaacttaca  tgcttttaa   gaatgcttct  ggtaagagac   6000
gattttgct   ctgtttgtta  ctttttacag  taatcactta  ttttttgtg   gtaattggca   6060
ttgccccaat  tttatccctt  tatgaattgg  attcaccact  ctgctggaat  gaagttttta   6120
taggttatgg  atcagctttg  ggtagtgcct  ctttttttgac tagtttccta  ggaatatggc   6180
ttttttctta  ttgtatggaa  gatattcata  tggccttcat  tgggatttt   accacgatga   6240
caggaatggc  tatgaccgcg  tttgccagta  caacactgat  gatgttttta  ggtgagttcc   6300
aagtgtagct  ttagaactaa  ctatgtattt  gatattcata  taaatgaat   ttagtctact   6360
gggggagaaa  ctttaatcta  aagccctcta  tttaagccat  tctagttcaa  ttaagggta    6420
ataactagtt  tgccaggagt  caataagcca  aaagccgaat  tcactttaaa  aatttaatcc   6480
actgaataac  cacaatttcc  caaatgtgta  tatttgcctc  aaaattgttt  tgaggaacat   6540
tcttcttatg  aatcagttct  tcaatatagc  tttcattaaa  gtgaagattt  cttaaaatgc   6600
tgctaataag  actacttccc  ataaaaatat  ttaggacaat  gatataaagt  atactaaaaa   6660
tacttataag  aaaaaaacta  tatcaattta  atatattcaa  gaagaaattt  tttaaagaca   6720
ggttttgcaa  attgatcttt  cagcaaattg  gccatttcat  aaaattgattt ttgatgaatt   6780
```

```
gctggttggc aaattagact gcttccttaa ctacctacct tataactgtt tttgcaggat    6840
tcaaatgaga tactgcattg aaaaaggctg tggaactata aaatgagact ctgggaaagg    6900
tccaatttac tcttttctct aataaaagtg ttaacccctt actatcttgc agggaagcag    6960
tgtgaccaaa tagaattggg cctaacttcc atctatagta ctagatgatc ttgggcaagt    7020
tactgaacta ctctcagccc tcattttctc atctgtaaaa tgggcgtggt actacctaat    7080
ttagaggatt acagtgaaca ttaggtagct gtcaagcact cgcttggcac aatccctact    7140
attcaataat agccagtttt tctccctgtc tccctaagag ctgccaaggt caggtaagtt    7200
aatctatgtg aaaacacttt gagaattgta aagtggtctg ctaatgtcat attttactat    7260
tttatgatgt aattaaaact actgactatt aagggtcata actgaagacc agaggtaatt    7320
tgtgtttatg aagttattct gccacaaaga tgaacaggca agatgataaa gaaccagttt    7380
accaataaat aaatcaatat aataaaggca tgctaacact aagagtgcca agtctgaaaa    7440
aagcacaaac aaaaatgaat tagcagtctc aatttgctaa ataagaggtt aatatataat    7500
taggaaaata agcagatcag tttttttttt tgttttttt ttttctttga gatggagtct    7560
cactctgtcg ccaggctgga gtgcagtggc atgatctggg ctcactgcaa cctccacctc    7620
ccgggttcaa gtgattctcc tgcctcagcc tcccaagtag ctgggattgc aggcatgcgc    7680
caccacgcct ggctaatttt gtattttag taaagacagg atttctccat gttggtcagg    7740
ctggtctcga actcccgaac tcaggtgatc tgccctcctc ggcctcccaa agtgctggga    7800
ttacaggtgt gagccactgc gcccggccag cagatcagtc ttaatcggca gattatataa    7860
atagatctag acctaaaaat tacatgaact cttgttctct gtactggaat aagaattcta    7920
gagtaaagta accttaaact gacctgtcca tagtctactt taattcatca aacagagttc    7980
tacaattaat taattcaatt tttagataca atgagttagg atgcttgtag aaaaggaagt    8040
atttagacag agtgaaagtg tttcctattt taaattggcc attagctttc agaatcagcc    8100
agtgattttg aatcctttct ctcacagcca gggtgccgtt cctttcact attgtgccat    8160 tctctgttct acggtccatg ttgtcaaaag tggttcgttc gactgaacaa ggtgagttta    8220
atttgcttaa gaaatatgaa tctaccatct ttacaaactc aaatctgtgt acaatcaatg    8280
tttaatgctt cagaatattc tacagcccTT tttatgcacg gatctccttt tgaataaagt    8340
ggtaagctct gtgagggaaa ggcttacact cttgcaaggg agccctgcc tagggccttg    8400 tactttagag agctccctcg gctctgggcc gtgccccgcc ctaagaagaa aggagctctc    8460
agggccaagt gggagatgcc cactgggagc tcaccacatc tccttccttc tagactgaac    8520
tctgcccacc tgggtccctg caattcccag cccagttctg ggcttatgtc cagtaagggc    8580
ctggatgatc ctcttcctca gccaccttct cctgagggtg gactgtgccc agtgtgctca    8640
cctgtagacc aaggaaggag ccaaggggcg actccttcta aagggtgtgg ctggactttg    8700
gaatcacagg gtggggctgt tccacaccct gtaatgaccc tttctgagca gggtggtgca    8760
aggggtagag cagaatgggg gtgggctcca gctgggcacc aagggctgag ggccagttca    8820
ccctgggcta ccctgttcct acgtggaatt ctgaaaacgt ctgagaatcc taagtgtgtg    8880
cgggtctcct agatcattca ttacaaaggg atattttca cagtaggaag gcataatata    8940
ttttagttaa cagtttgttg gccagatttc aaataactga ccacttttaa atcctaagaa    9000
tataatatat aggcctctga taatgttctt acactggccc ctacaactgt cacagctggg    9060
cctgactcag agtcctggca gaaaacgggg ccccactcag ctggttcaat caagaaactt    9120
```

```
tcatgaaggc cattatagag agtgggcatt gtcgaggcag ccagagagat gccccagata   9180
ggaagcagag aagaaacacc ataacctttc tccccatca tccttttaac caagtgcagc    9240
aggaactcgg gccagcaaga agtccaagt catataattt gtggggtcag cctccaaagc    9300
acagagcagg gtacacaaag tcaaacagtt gaaggggcag gcagagaata accaggatgc   9360
agcaaagaca aaaattaaat ttccattgag aactagttac tagttagata tcaggcatat   9420
gggcttgtcc tccttccctt ttgtatcata tgaatcttat tagacattgg cactttcttt   9480
aatgtcatat gttagcccgg tgctgtgaat gtacttattt gatttatgaa taattcataa   9540
ttatgctgtt gtattttac cagtttagtc aatactggag aaggctacat aattcaataa    9600
attaaaaata tatttcttct tttactttct ctctttttt ttttttttga gacggagttt    9660
cactcttgct gcccaggctg gagtgcaatg gtgtgatctc ggctcactgc aacctctgcc   9720
tcctgggttc aagcaattct cctgcctcag cctcccaagt agctggaatt acaggctcct   9780
gccaccatgc ctggctaatt tttgtgtttt tagcagagac agggtttcac catgttggcc    9840
aggctggtct caaactcctg acctcaggta atcagcccgc ctcagcctcc caaagtgctg   9900
ggattatagg cgtgacccac cgcacccggc ctcttatttt tcactcataa gatgtagcta   9960
tatattcaca catctgttta tagatgatgt gatgatgatt gctttgaaaa ccaataacaa   10020
atggaaaaat ttatataaac tatgtaaaaa tctatctgct tctttggact atgcaatagt   10080
ttcttagata tgacaccaaa agcacaagaa caaaggaaaa attgatagat tagacttcat   10140
ccaaaaactt cattcaaagt ttgtcctttg aaaatttttt atgtttcaaa ggacaacatc   10200
aagaaagtga ggccaggcgc agtggctcac atgtgcaatc ccagcacttt gggaggccaa   10260
agcgggtgga tgacccgagg ttaggagttt gagaccagcc tgaccaacat ggtgaaaccc   10320
cgtctctact aaaaatacaa aaaaaaaaa aaaaagaaa agaaaagaa agaaagtgaa      10380 atgacaaccg acaacccaca gaatgggaga agatatttgc aaattatatt tgtctgagca   10440
ggaactcgta tccagcatat ttaagaactc ttaaaattca acaacaaaaa gacaactcaa   10500
tttaaaaatg ggcaaaggat ttgaatagaa gatatacaag tgaccaatat gcgcatgaaa   10560
atgctggata tcattagcca tcagggaaat gcaaagcaaa accacagagt gggctggggt   10620
ggccaaaata aaataggcca tagcaagtgt tgatgaggat gtggagaaat tggagccctc   10680
atacactgcg agtgggaaca taaaatggtg cagcagctgt acaaagcagt ttggcagttc   10740
ctcagaaagt tagttgcctt atgactcagc aatccctccc ctacttacat accatgagaa   10800
gtgaaagcat atgtccacat aaaatcttgt tcatggcagc attattcata atagccaaaa   10860 agtgaaaccct atgcaaatgt tcatgaactg acaaatgggt aaacaaaatg tggtttatcc   10920
atccagcaaa ctgctcttct gcaataaaaa gaaatatcgt tctgttacat gccataacat   10980
ggatgaacta tgaaatgatt atgccaaatt taagaagcta gtcacaaaag gccacatatt   11040
gtcatttaaa tatgattctg tttacgtgaa atgtgcagaa taggcaaatc catagagaca   11100
gaaatttgat tagggcttga ctgggctgg ggaagggaa tgactactta tgggtataca    11160
gtttcttttc ggggtgatga aaatgttcca cagatagtgg tgatggttgc acaaatctgc   11220
aacatactaa gaaccactga attgcagact ttaaagggt gaggtttgtg ggatgttaat    11280
tatatcccaa taaagctatt gggaaaaaaa atttacctgc tttgacttag agctaaaata   11340
gagctgtcaa gaggtatagt ttatttttgt ttatatttgg tttagtttat aaaggctttt   11400
taaaattttt tttattatac tttaagtttt agggtacatg tgcacaacgt gcaggtttgt   11460
tacatatgta tacatgtgcc atgttggtgt gccgcaccca ttaactcgtc atttagcatt   11520
```

```
aggtatatct cctaatgcta tccctccccc ctcctccctc ccccactcc acgacaggcc   11580 ccggtgtgtg atgttcccct tcctgtgtcc aagtgttctc attgttcaat tcccacctgt   11640
gagtgagaac atgtggtgtt tggttttttg ctcttgcgat ggtttgctga gaatgatggt   11700
ttccagcttc atccatgtcc ctacgaagga catgaactca tccttttgta tggctgcata   11760
gtattccatg gtgtatatgt gccacatttt ctcaatccag tctatcattg atggacattt   11820
gggttggttc caagtctttg ctattgtgaa cagtgccaca ataaacatac gtgtgcatgt   11880
gcctttatag cagcatgttt tataatcctt tgggtatata cccagtaatg ggattgctgg   11940
gtcaaatggt atttctagtt ctagatcctt gaggaatcac cacactgtct tccacaatgg   12000
ttgaactagt ttacagtccc accaacagtg taaaagtgtt cctatttctc cacatcctct   12060
ctagcacctg ttgtttccta acttttaat gatcgccatt ctaactggtg tgagatggta   12120
tctcattgtg gttttgattt gcatttctct gatggccagt gatgatgagc atttttcat    12180 gtgtctgttg gctgcataaa tgtcttcttt tgagaagtgt ctgttcatat ccttataaag   12240
gcttttaaaa agtcatctcc gccaggtgca gtggctcaca tctgtaatcc cagcactttg   12300
ggaggccgag gtgggaggat cacttgagac caggagttca aaagcagtgt gggcaacaga   12360
gggaggctct atctctacga aaaataaaca taaaaataaa aagtcatat catactgtta    12420 aatatagtaa tattttaaaa tgtttacatt ttggcatttc ttattttgaa ttacggtaac   12480
tgtgaattgt gacttcatta ttctaggata cttactttgt tcttaactgc aaactaaaca   12540
atcttttgga tgatgtcaac atttctataa ctaaatgtat tcgcatcctt cattattatt   12600
taaattggcc attttgtgaa atattaggc actttaaata atcagaggag tggggaaata    12660
ctgccgaagt tttcagttgg ctctcattat ttctattatc ttaaataaga aggtaagaa    12720 agtggaattc tggtaattat tttgcaatct ctgcgctctg caccactgtg aactcatagc   12780
tgaagctgcc ttggactatt ttacctgggc atcacccata tactccttgt tattataaat   12840
tgggagacag taaaacagac ttgattttg aggtctattg cattaaaaaa aaacagaatt    12900
tagaagatga actcagttgt acttatcctt taatcctgtt ttatctctgg caactattaa   12960
acaagtcgaa ctgctcagag aagttgggca ataagctaaa gctacttcat aatagtatgg   13020
ttccatcaga acagatggtg cagtgtctga cctatttccc atcaagaata gattaaaact   13080
cttacataat agaactagta ctgtgcagtc tgttttccat agcactattc ctggctgcag   13140
aaagagatca gaaataaaag aaaataatgt agttagacaa gtagaagaac atccttccaa   13200
ttaaactgac ttaatgtatt atcataaatc atggaggcag taagtctgca tgctacttga   13260
tgactggtaa atgggatcct gaattaagct ttgattcatt catttgacaa atatttatta   13320
aatgtctgcc atgcacccgg acagctgagc cctaggata cagctgtgag caaggcagat    13380
gtacaaggca gatcgacaaa gctttcattt tagtcaaaag aagacacata agtgagcaca   13440
cgatattttg cagagataga cgtatgtttt atgaatgttt gtcctatcat tcaatgaata   13500
atttgaagca atatatgaga atatgtacaa taaatgaaa agtttaaat  agataaaaat    13560 caatacacag tctaaaagat gaagaccatg gggaaatta gaatatacac ataagccata    13620
tctaactttg aaagataacc ctcaagcttg gccatttcct tcctatcagt ccaagcaaac   13680
acaattattt acatgatttg tattgtcagt aagaaaaatg cattgcagtt tttcatggaa   13740
aagtaaactt ggcaaagtag ggaacaagca tagtgacttg ttgacaaaat ctgcagaaag   13800
cagaagctac atatatagga actgagacca agaaagccag gtcaatctga ctgaaaatgg   13860
```

```
tcatgaaatt ttatatctga tgatgagcaa tttgacaaag aggaagaaaa gcacatgaag    13920
atggccagcc tgtctttgg aagtttaact cttcagttga catggtcttg gattccagac    13980
aaaactaaac ataggtagaa tactgtctgt ttctctctga ttgtgagctt gcactgacca    14040
tgcagacttc atgaacaatg ctgagtggcc taccttgac caactttggt gtatagcaag     14100
tgtgaccata gcagaatccc cactcttcat cttgtaaggc accttagggc agaggcagtt    14160
gcaagcaata aggtggaaac atatgtttta aagaatcact taacattaaa ctgtggcata    14220
aaccttcact agagcacaag atggttaatt tgatgagtca acatgcaga atctagtagt     14280 gatgggattt tttggtgact ttgaagaggg ataaaattcc agttgcagaa tgtataagaa    14340
tctcctctct ttgtctgcag ctgtcacttg ccagactgag aacagataa gaaggtttc      14400 tttaccttc aaaaggctct tgcaggaagc attgcttgtt aggagccatc ctgtgctttc     14460
aggtgtcaca gattagcatg gggttggagg gtggagaca gcatcctgaa gagcaggggt     14520
aggtgtggct ttgcctgggg ctgtggcaga gaggagagac atgcagttat caaaagagtc    14580
agctgcactg tcttttttagc tttgcctgt ggacactgga actcagctat ttggagtttc    14640
caacatctct cacatcaagt ccaaggagaa cctttccctt agtttcctca gctgcagaat    14700
gggctgctga cttctcaggg actttgaggg ataactttc atttcattca cccagcagtg    14760
ccctcatgtt tactgttttc aatgagtaac agttgtctcc attagtttgt gtttgttgtt    14820
ttgtaattct gcctttttt tttcctctct ctctatccct actccaaaca ggtaccctgt    14880
ttgcttgtat tgctttctta gaaacacttg gaggagtcac tgcagtttct acttttaatg    14940
gaatttactc agccactgtt gcttggtacc ctggcttcac tttcctgctg tctgctggtc    15000
tgttactact tccagccatc agtctatggt atgtcattat ttttaatcat tttatcagag    15060
ggtatatgga ttaagtgaat tccctaacct caccagtaaa ttacataggt ctgttgaaat    15120
tttgcctcag aacgtgcttt tctcaagaac ttttagacat gaagtgctcg cttcagcagc    15180
atatatacaa aattggaatg acacagtgaa gattggcatg ctccctgtgc aaggatgaca    15240
ggaaaattca tgaagtgttt catattttaa taaaataaat ttttttaatt aaaaaaaga    15300 gaaccggtca tggtggtgta tgtctgaagt ctcagctagt caggagactg agacgggaag    15360
atgattttga gcccaggtgt ttgagaccag cctggacaac atagcaagac ccccatctca    15420
ttaaaataaa taaaaatacg tgaaagcatc tgtcaataat ttggggagac ttaggaagaa    15480
aaagagagtg acatgggtga agaactaaaa gaaggattgt gttcattata actccccacc    15540
tttaaaccat tgattaaatt agcatctaaa attagagatg tatacctta aactatgatt     15600 tcccagagta caatatcccc tgatggtcaa agattgctgt aatgagattg actttcacat    15660
ggattcttgt ataaatgaca aaagcagata ggatgtgctg actattgagt tctctttcca    15720
gagttggctt gtttaatgac tttgtcttgt tttaatgact tgtttaaacg ttaatgttta    15780
aatgttttta aatttaaata ttcaaattaa agaagcacaa aattccattt atgaatagta    15840
catataatgg atagatcaga agcataaata taaaagcaat atttatgcct tctttttgct    15900
ttctatttaa caaaaaatgt gagccaacta gatgaatgat tgctgaaacg tccaagcaaa    15960
tttatttgac acattaatga agagctcatt aatctgtttc tgctgagctc tgtgcatttc    16020
atgtggctga tagcatagca cagtgacggg aatcaaggca atggggccac aagaagccag    16080
gccttctctg ctttctccta agcactttgg ggtaaggctc tgagttaggg aggaaagtgc    16140
ctataagcac aggtgttaag catcctgcca agatggcaaa ctccctaaag ggctggctca    16200
tgtcttatag taggagctca gtacttattg tttctattga attctgatac ctagatctgt    16260
```

```
gtcagagaac aacagtattt gcagttcctc taattttgat gaaaagttat ttatactagt   16320 tatcttttt  aaaagagac  tattcaccta  tcgaattaac  aaaattacca  atacatgctg   16380
tgctggtaag cacatgagac aactgatctt acacattgtt gataatagta ctattcagct   16440
gtatcataaa gcaattcatg aatatatcaa aagctctttt ttcaaagttc atagtgattg   16500
atccagcaat tccttttaga aacatactct aaacaaataa tgagtaattt tgtcaaaaat   16560
tgatatataa aaacgttaat tacagcaaaa aaattttaag tgaccaaact gtccaacagt   16620
gggagaatgt ttaagtaaat gatggtacag ccatttcatg aaaaatgact taactaacaa   16680
gaattgtagc aggcaccgtg gctcacacct ataatcccag cactttggga ggttgaggca   16740
ggaggactgc ttgaggccag gagttcaaga ccaatctggg caacatagtg gacccccat    16800 ctttaccaaa aaaaaacaga ttttttaaa  cagtaggaaa ataacactta aagaaaagaa   16860
ttgcatacat ggtgagtaga ataataggta attctaattt tagtcttcac atgtttataa   16920
attctgttat aacagataga taaaaggcag ttgtccttt  aataataagg taagtagat    16980 gggcttctga gcttttttt  taaccttaca ctgctcaata ttttaaaaat caaaattaca   17040
tactgtctta cctccaaatg tccaagcttc tgagcttcag ctatagctat tgaacaggaa   17100
cttcagtaat agctttagtt ataactagtt tatgtggact acacagagtt aaccatggga   17160
cagatgggat accttagggg tctagaagag aaaaaaaatc atgcagtttt aaaattattt   17220
taagaacacc atgcatgagt cagctggatt caaaatgcca ggatactcct cctaataatc   17280
tgcataattt attaaaagct atgtaactgg gaaaaaagt  tggaaaacag attacttatt   17340
tatgtattgt cttaatctca actttaaaat gtcttgtttc cttttatagt gttgtcaagt   17400
gtaccagctg gaatgaggga agctatgaac ttcttataca agaagaatcc agtgaagatg   17460
cttcagacag gtgactgtga tttaaacaaa caaaaaaaat ctatgaatgc acatatcata   17520
taccatgact tctgaagact ataaatgaat tccacaatca gtgcttcact gagaaccaat   17580
tttacctatc tttcttcta  aactgaacag tcagagagac agctcctggc tttagcttct   17640
tgtggtacca cgcactttga gcactttgtg cgtatcatgc aatatacttg caatacacag   17700 aacaaattc  aaatacgcct cacttttaga cttagaagag aaacattaaa acttaagggt   17760
gtaaggaggg atcaagaaac ttgataaggt caaaagcaat aatctctctg acatattcca   17820
ggctcttaca ctgagaccaa agagaaatct ttacctcagt ttcttcatca gcagaatggg   17880
tttctggcct ctctcaggga taattttgaa ggcataatga aaattatgat gaatcactca   17940
ttggtaggaa aataatgata taagtttcaa atatgtatga ttttacctat acttggtaat   18000
gctttatttt atagagcctg ttaagctgct attgatagtc ggagcttata tactgtgact   18060
tctgaagact atacatgaat tccacaatca gtgctttgtt gatacaaaat ccttaaaagg   18120
gaggcacttt aaagaatatg tattttcac  ttttcttaat atgtttcatc ggtgacaggc   18180
atgataatat ttctatatgt aatgggtaat tgggaaaaaa tagatgataa ataaaattgc   18240
tctaaagaag ttaaaaaact gaatgaacag ctaatactgg tataaagtaa ctaatgtttg   18300
gagccaacat ttgttccttg tgtcagcaaa aggatattca cattccatga tccctggctg   18360
agaattctgc ctctagtctt tcttacccag ctgttgtcta tccttgttca attataaata   18420
ctgctaaggg cattttaaa  atacgatctt gtactcctta aatttgaatc cgtcaacacg   18480
gtcactcata ggaaaatgat caaacaagca agccagtcat gatttgactc cttcccatct   18540
catttcttac tgccttacgc tcatcctgag gtccaccttg gtctctaaaa acaccatgtg   18600
```

```
ttctcatgcc tccatgtctt ttcacacact gttccatttg ctcttcctcc cacattacat    18660
tgaaactttc aagcctcagt cgaaacattg cttcttctgg atagcagcct tcttgacatc    18720
cctcctcact ccccagtccc tacagggctt ccatagctct ttgtgtgcac ttcgatccca    18780
gcattttcca tcgacttgta attgtttctg ctacctgaca atcatcgcct tgagtactgg    18840
gacaaccttt gattactcat tatatcctca ataatatttt gttgaactaa actaaatgac    18900
tacaaaa                                                             18907

<210> SEQ ID NO 2
<211> LENGTH: 463
<212> TYPE: PRT
<213> ORGANISM: Artificial Sequence
<220> FEATURE:
<223> OTHER INFORMATION: Synthetic

<400> SEQUENCE: 2
```

Met Lys Ile Leu Phe Val Glu Pro Ala Ile Phe Leu Ser Ala Phe Ala
1               5                   10                  15

Met Thr Leu Thr Gly Pro Leu Thr Thr Gln Tyr Val Tyr Arg Arg Ile
            20                  25                  30

Trp Glu Glu Thr Gly Asn Tyr Thr Phe Ser Ser Asp Ser Asn Ile Ser
        35                  40                  45

Glu Cys Glu Lys Asn Lys Ser Ser Pro Ile Phe Ala Phe Gln Glu Glu
    50                  55                  60

Val Gln Lys Lys Val Ser Arg Phe Asn Leu Gln Met Asp Ile Ser Gly
65                  70                  75                  80

Leu Ile Pro Gly Leu Val Ser Thr Phe Ile Leu Ser Ile Ser Asp
                85                  90                  95

His Tyr Gly Arg Lys Phe Pro Met Ile Leu Ser Ser Val Gly Ala Leu
            100                 105                 110

Ala Thr Ser Val Trp Leu Cys Leu Leu Cys Tyr Phe Ala Phe Pro Phe
        115                 120                 125

Gln Leu Leu Ile Ala Ser Thr Phe Ile Gly Ala Phe Cys Gly Asn Tyr
    130                 135                 140

Thr Thr Phe Trp Gly Ala Cys Phe Ala Tyr Ile Val Asp Gln Cys Lys
145                 150                 155                 160

Glu His Lys Gln Lys Thr Ile Arg Ile Ala Ile Asp Phe Leu Leu
                165                 170                 175

Gly Leu Val Thr Gly Leu Thr Gly Leu Ser Ser Gly Tyr Phe Ile Arg
            180                 185                 190

Glu Leu Gly Phe Glu Trp Ser Phe Leu Ile Ile Ala Val Ser Leu Ala
        195                 200                 205

Val Asn Leu Ile Tyr Ile Leu Phe Phe Leu Gly Asp Pro Val Lys Glu
    210                 215                 220

Cys Ser Ser Gln Asn Val Thr Met Ser Cys Ser Glu Gly Phe Lys Asn
225                 230                 235                 240

Leu Phe Tyr Arg Thr Tyr Met Leu Phe Lys Asn Ala Ser Gly Lys Arg
                245                 250                 255

Arg Phe Leu Leu Cys Leu Leu Leu Phe Thr Val Ile Thr Tyr Phe Phe
            260                 265                 270

Val Val Ile Gly Ile Ala Pro Ile Phe Ile Leu Tyr Glu Leu Asp Ser
        275                 280                 285

Pro Leu Cys Trp Asn Glu Val Phe Ile Gly Tyr Gly Ser Ala Leu Gly
    290                 295                 300

-continued

```
Ser Ala Ser Phe Leu Thr Ser Phe Leu Gly Ile Trp Leu Phe Ser Tyr
305                 310                 315                 320

Cys Met Glu Asp Ile His Met Ala Phe Ile Gly Ile Phe Thr Thr Met
            325                 330                 335

Thr Gly Met Ala Met Thr Ala Phe Ala Ser Thr Thr Leu Met Met Phe
            340                 345                 350

Leu Ala Arg Val Pro Phe Leu Phe Thr Ile Val Pro Phe Ser Val Leu
        355                 360                 365

Arg Ser Met Leu Ser Lys Val Val Arg Ser Thr Glu Gln Gly Thr Leu
    370                 375                 380

Phe Ala Cys Ile Ala Phe Leu Glu Thr Leu Gly Gly Val Thr Ala Val
385                 390                 395                 400

Ser Thr Phe Asn Gly Ile Tyr Ser Ala Thr Val Ala Trp Tyr Pro Gly
                405                 410                 415

Phe Thr Phe Leu Leu Ser Ala Gly Leu Leu Leu Pro Ala Ile Ser
            420                 425                 430

Leu Cys Val Val Lys Cys Thr Ser Trp Asn Gly Ser Tyr Glu Leu
        435                 440                 445

Leu Ile Gln Glu Glu Ser Ser Glu Asp Ala Ser Asp Arg Ala Cys
    450                 455                 460
```

<210> SEQ ID NO 3
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(36)
<223> OTHER INFORMATION: n is any nucleotide

<400> SEQUENCE: 3
aatgatacgg cgaccaccga gatctacann nnnnnnaagg tgcttctcga tctgcat    57

<210> SEQ ID NO 4
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (25)..(32)
<223> OTHER INFORMATION: n is any nucleotide

<400> SEQUENCE: 4
caagcagaag acggcatacg agatnnnnnn nngtgactgg agttcagacg tgtgct    56

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
caccgggcga ggagctgttc accg    24

<210> SEQ ID NO 6
<211> LENGTH: 24
<212> TYPE: DNA
<213> ORGANISM: Artificial Sequence

```
<220> FEATURE:
<223> OTHER INFORMATION: Synthetic

<400> SEQUENCE: 6
aaaccggtga acagctcctc gccc                                              24

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
caccgaaagc aagctcccca aaatg                                             25

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
aaaccatttt ggggagcttg ctttc                                             25

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
tgccattctc tgttctacgg                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tgcagtgact cctccaagtg                                                   20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
agacaaatcg ctccaccaac                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
cctgcggctt aatttgactc                                                   20
```

SOLUTE CARRIER FAMILY 46 MEMBER 3 (SLC46A3) AS MARKER FOR LIPID-BASED NANOPARTICLE CANCER THERAPY AND DIAGNOSTICS

CROSS REFERENCE

This application claims priority to U.S. Provisional Patent Application Serial Nos. 63/140,315 filed Jan. 22, 2021; 63/170,874 filed Apr. 5, 2021; and 63/248,438 filed Sep. 25, 2021; each incorporated by reference herein in its entirety.

FEDERAL FUNDING STATEMENT

This invention was made with Government support under Grant No. W81XWH-19-1-0257 awarded by the United States Army Medical Research Acquisition Activity and Grant No. T32 CA126432-08 awarded by the National Institutes of Health. The Government has certain rights in the invention.

SEQUENCE LISTING STATEMENT

A computer readable form of the Sequence Listing is filed with this application by electronic submission and is incorporated into this application by reference in its entirety. The Sequence Listing is contained in the file created on Jan. 20, 2022 having the file name "21-1488-US-SeqList_ST25.txt" and is 31 kb in size.

BACKGROUND

Cancer nanomedicine has attracted intense research and clinical interest given the potential to tune nanomaterials for enhanced drug delivery sites of disease. Nanoparticles have been established to improve therapeutic properties largely by extending circulation time and mitigating toxic side effects. Targeting strategies have been devised in an effort to improve the specificity of nanoparticle-cancer cell interactions, but tumor accumulation remains below 1% of the injected dose. Progress has been impeded by a limited understanding of the cellular processes governing these interactions in cancer cells of heterogeneous lineage and genetic backgrounds.

SUMMARY

In a first aspect, the disclosure provides methods of identifying a subject who is susceptible to treatment for cancer with lipid-based nanoparticle therapies, the method comprising determining expression levels of solute carrier family 46 member 3 (SLC46A3) in a plurality of cancer cells from a subject having cancer, wherein a subject with decreased SLC46A3 expression levels as compared to historical controls is susceptible to treatment with lipid-based nanoparticles.

In one embodiment, the disclosure provides methods of identifying cancer cells susceptible to treatment with lipid-based nanoparticle therapies, the method comprising
  (a) obtaining cancer cells from a subject; and
  (b) determining expression levels of SLC46A3 in said cells, wherein the cells with decreased SLC46A3 expression levels as compared to historical controls are susceptible to treatment with lipid-based nanoparticles.

In one embodiment, the method further comprises administering to a subject identified as susceptible to treatment with lipid-based nanoparticle therapies or identified as having cancer cells susceptible to treatment with nanoparticles, an amount effective to treat or diagnose cancer of a lipid-based cancer therapy nanoparticle. In a further embodiment, the methods further comprise monitoring the lipid-based cancer therapy nanoparticle treatment in the subject, comprising determining expression levels at multiple time points of SLC46A3 in a plurality of cancer cells from a subject, wherein the expression levels at later time points relative to the expression level at earlier time points indicates an efficacy of the lipid-based cancer therapy nanoparticle in the subject.

In another aspect, the disclosure provides methods of treating cancer in a subject, the method comprising
  (a) identifying a subject with cancer cells, such as malignant cells, that have a normal or increased SLC46A3 expression level as compared to historical controls, and
  (b) delivering to said subject an amount effective to treat the cancer of:
    (i) a composition to decrease SLC46A3 expression; and
    (ii) a lipid-based cancer therapy nanoparticle.

In one embodiment, the lipid-based nanoparticle comprises a liposomal nanoparticle. In another embodiment, the lipid-based nanoparticle comprises a solid lipid nanoparticle.

In another aspect, the disclosure provides compositions for treating cancer, the composition comprising
  (a) an inhibitor of SLC46A3 expression; and
  (b) a lipid-based chemotherapeutic-containing nanoparticle.

In one aspect, the disclosure provides methods of identifying subjects suitable for enrollment in a clinical trial for nanoparticle cancer therapy, comprising the following steps:
  a) determining expression levels of SLC46A3 in a plurality of cells from multiple subjects diagnosed with cancer;
  b) further determining whether the SLC46A3 expression levels from said patients are increased or decreased levels of expression as compared to historical controls, and
  c) identifying as subjects suitable for enrollment in a clinical trial for nanoparticle cancer therapy those patients with decreased SLC46A3 expression levels compared to historical controls.

DESCRIPTION OF THE FIGURES

FIG. 4. Retention and accumulation of PEGylated liposomes (LIPO-0.3% PEG*) in LOXIMVI tumors is dependent on SLC46A3 expression. (A) Fluorescently labeled LIPO-0.3% PEG* NP were administered to mice bearing LOXIMVI flank tumors via a one-time intratumoral injection or repeat intravenous injections. (B) Whole animal fluorescence images of mice (4 males, 6 females per group) 24 h after being intratumorally injected with LIPO-0.3% PEG* NPs. (C) Quantification of LIPO-0.3% PEG* NP retention after intratumoral administration to LOXIMVI flank tumors. (D) Quantification of LIPO-0.3% PEG* NP accumulation after repeat IV injections. In panels C-D, nanoparticle signal is expressed on the y-axis as radiant efficiency divided by tumor mass (mg). The mean and standard deviation of n=10 are shown with the exception of the LOXIMVI-vector control, repeat IV injection group, where n=9 (<0.01, *<0.001, Mann-Whitney test).

FIG. 9. Raw data and histology images for in vivo studies. (A) Flow cytometry histograms for LIPO-0.3% PEG* (drug-free analog of liposomal irinotecan) in LOXIMVI cells overexpressing SLC46A3 (SLC46A3 OE) or luciferase (vector control) after 4 and 24 hours incubation with NPs. (B) In vivo fluorescence images of mice bearing LOXIMVI flank tumors (n=10/group, 5 male and 5 female) 4 hours after intratumoral injection with LIPO-0.3% PEG* NPs. (C) Radiant efficiency from ex vivo tumors quantified in (D). Radiant efficiency from ex vivo tumors used to generate plots in main manuscript FIG. 4C (E) and FIG. 4D (F). (G) H&E staining of LOXIMVI tumor cross-sections show grossly similar morphology. Top two panels, scale bar=2 mm; bottom two panels, scale bar=0.1 mm.

DETAILED DESCRIPTION

Figure 1A:
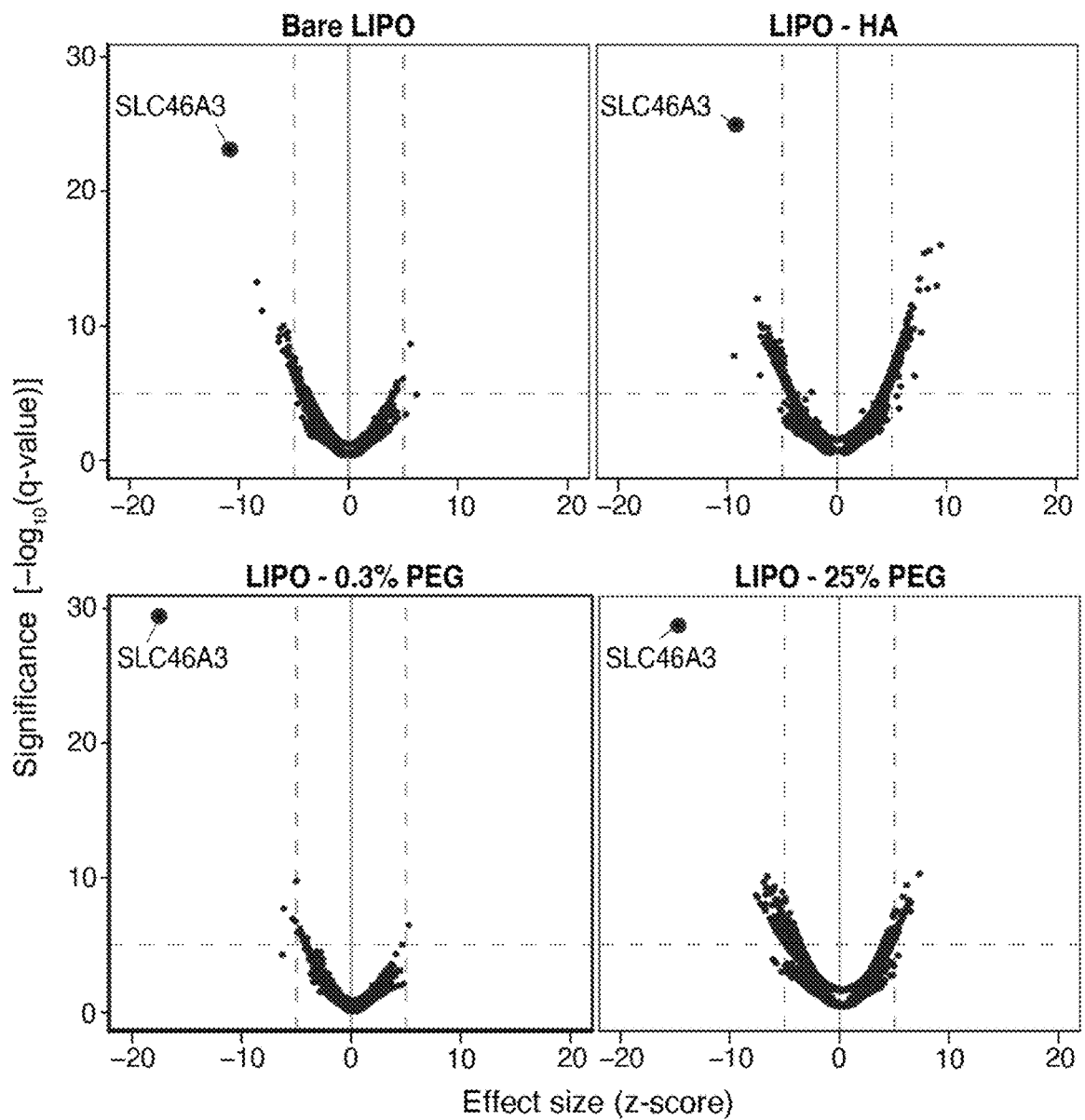
FIG. 1. Native expression of the lysosomal transporter SLC46A3 is strongly predictive of NP-cell interaction for liposome formulations. (A) Univariate analysis identifies SLC46A3 expression as strongly yet inversely correlated with liposome association, regardless of liposomal surface modification. (B) Using linear regression to evaluate the biomarker relationship across core formulations reveals SLC46A3 expression is inversely correlated with NP association in liposome-cell line pairs (p<0.001) but not PLGA- and PS-cell line pairs (p>0.05); n=488 for each plot. (C) Cell lines in the pool exhibit a range of natural SLC46A3 expression levels with a log linear correlation with uptake of liposomes. (D) This correlation is also exhibited when assessing liposome-cell associations via flow cytometry in a non-pooled fashion (p=0.013). Cell lines in red were not part of the pooled screen. Data represented in D is shown as the mean and standard deviation of four biological replicates.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

All embodiments of any aspect of the invention can be used in combination, unless the context clearly dictates otherwise.

As used herein, "about" means+/−5% of the recited value.

In a first aspect, the disclosure provides methods of identifying a subject who is susceptible to treatment for cancer with lipid-based nanoparticle therapies, the method comprising determining expression levels of solute carrier family 46 member 3 (SLC46A3) in a plurality of cells from a subject having cancer, wherein a subject with decreased SLC46A3 expression levels as compared to historical controls is susceptible to treatment with lipid-based nanoparticles.

In one embodiment, the disclosure provides methods of identifying cancer cells susceptible to treatment with lipid-based nanoparticle therapies, the method comprising (a) obtaining cancer cells from a subject; and
(b) determining expression levels of SLC46A3 in said cells, wherein the cells with decreased SLC46A3 expression levels as compared to historical controls are susceptible to treatment with lipid-based nanoparticles.

As disclosed in the attached examples, the inventors have identified SLC46A3 as a biomarker whose expression inversely predicts lipid-based nanoparticle uptake both in vitro and in vivo, and have identified SLC46A3 expression reduction as a means to improve lipid-based nanoparticle delivery to cancers, and thus to improve cancer therapies.

The human SLC46A3 gene sequence is provided as SEQ ID NO:1, and the protein sequence is provided as SEQ ID NO:2 (NCBI Reference Sequence: NC_000013.11).

As used herein, a "nanoparticle" is any particle with a widest diameter in the nm scale (1-999 nm).

As used herein, a "lipid-based nanoparticle" is any nanoparticle comprised of lipids, including but not limited to liposomal nanoparticles and solid lipid nanoparticles.

As used herein, "nanoparticle therapies" comprise nanoparticle delivery of cancer therapeutics or diagnostics to a subject. In one embodiment, the nanoparticle comprises nanoparticle delivery of cancer therapeutics to a subject.

As used herein, "nanoparticle delivery" is defined as the accumulation of nanoparticles containing diagnostic and/or therapeutic modalities in cancer cells.

Any suitable lipid-based nanoparticle therapy may be implicated in the methods disclosed herein, as deemed appropriate by attending medical personnel. In various non limiting embodiments, the lipid-based nanoparticle therapy is selected from the group consisting of cancer therapy nanoparticles shown in Table 1.

TABLE 1

Exemplary clinically approved nanoparticle therapies and diagnostics, grouped by their broad indication

| Name | Particle type/drug | Approved application/indication | Investigated application/indication |
| --- | --- | --- | --- |
| VYXEOS CPX-351 (Jazz Pharmaceuticals) | Liposomal formulation of cytarabine:daunorubicin (5:1M ratio) | Acute myeloid leukemia | Various leukemias |
| NBTXR3 Hensify (Nanobiotix) | Hafnium oxide nanoparticles stimulated with external radiation to enhance tumor cell death via electron production | Locally advanced squamous cell carcinoma | Locally advanced soft tissue sarcoma |
| Doxil Caelyx (Janssen) | Liposomal doxorubicin (PEGylated) | Ovarian cancer (secondary to platinum based therapies) HIV-associated Kaposi's sarcoma (secondary to chemotherapy) Multiple myeloma (secondary) | Various cancers including: solid malignancies, ovarian, breast, leukemia, lymphomas, prostate, metastatic, or liver |
| DaunoXome (Galen) | Liposomal daunorubicin (non-PEGylated) | HIV-associated Kaposi's sarcoma (primary) | Various leukemias |
| Myocet (Teva UK) | Liposomal doxorubicin (non-PEGylated) | Treatment of metastatic breast cancer (primary) | Various cancers including: breast, lymphoma, or ovarian |
| Abraxane (Celgene) | Albumin-particle bound paclitaxel | Advanced non-small cell lung cancer (surgery or radiation is not an option) Metastatic breast cancer (secondary) Metastatic pancreatic cancer (primary) | Various cancers including: solid malignancies, breast, lymphomas, bladder, lung, pancreatic, head and neck, prostate, melanoma, or liver |
| Marqibo (Spectrum) | Liposomal vincristine (non-PEGylated) | Philadelphia chromosome-negative acute lymphoblastic leukemia (tertiary) | Various cancers including: lymphoma, brain, leukemia, or melanoma |
| MEPACT (Millennium) | Liposomal mifamurtide (non-PEGylated) | Treatment for osteosarcoma (primary following surgery) | Osteosarcomas |

TABLE 1-continued

Exemplary clinically approved nanoparticle therapies and diagnostics, grouped by their broad indication

| Name | Particle type/drug | Approved application/indication | Investigated application/indication |
|---|---|---|---|
| Onivyde MM-398 (Merrimack) | Liposomal irinotecan (PEGylated) | Metastatic pancreatic cancer (secondary) | Various cancers including: solid malignancies, breast, pancreatic, sarcomas, or brain |

As used herein, "expression levels" of SLC46A3 may comprise protein expression levels, RNA expression levels, or both. In one embodiment, the expression level comprises gene expression levels of RNA.

The plurality of cells from the subject may be any cancer cells obtained from the subject. In various embodiments, the plurality of cells may comprise cells obtained from any suitable biological sample from the subject, including but not limited to cancer cells obtained via biopsy or cancer-directed surgery or via blood sample, cerebrospinal fluid sample, urine sample, peritoneal fluid sample, pleural fluid sample, or any other bodily fluid sample containing cancer cells.

As used herein, "historical controls" may be any suitable control for comparing SLC46A3 expression. In one embodiment, the control comprises a reference range of expression levels from control cells expressing SLC46A3, or a contemporaneous measurement of SLC46A3 expression in control cells known to express SLC46A3. This embodiment may be useful, for example, when the methods seek to identify reduced SLC46A3 relative to control. In another embodiment, the control may be a reference range of expression levels from control cells that do not express SLC46A3, or a contemporaneous measurement of SLC46A3 expression in control cells known not to express SLC46A3. This embodiment may be useful, for example, when the methods seek to identify cells that express SLC46A3. In another embodiment, the control may comprise a cohort of historical controls such as those profiled and publicly available through The Cancer Genome Atlas (TCGA) database, a reference level determined for a particular cancer type or subtype, or a reference level determined from an individual patient from an earlier timepoint. Those of skill in the art will recognize that other such controls can be used in the methods of the disclosure.

Any decrease in expression levels of SLC46A3 can improve susceptibility of the subject to lipid-based nanoparticle delivery. In various embodiments, the decrease in expression levels relative to historical control is at least 10%, 25%, 50%, 75%, 80%, 85%, 90%, or greater decrease in expression levels relative to control.

In one embodiment, the methods further comprise administering to a subject identified as susceptible to treatment with lipid-based nanoparticle therapies or identified as having cancer cells susceptible to treatment with nanoparticles, an amount effective to treat or diagnose cancer of a lipid-based cancer therapy nanoparticle. In this embodiment, the methods provide improved treatment and diagnostic methods by administering the lipid-based nanoparticle therapies to those subjects that will benefit from the administration. As will be understood by those of skill in the art based on the teachings herein, these methods can also be used to monitor therapy. Thus, in another embodiment the methods further comprise monitoring the lipid-based cancer therapy nanoparticle treatment in the subject, comprising determining expression levels at multiple time points of SLC46A3 in a plurality of cancer cells from a subject, wherein the expression levels at later time points relative to the expression level at earlier time points indicates an efficacy of the lipid-based cancer therapy nanoparticle in the subject.

In this embodiment:
(i) a reduced SLC46A3 expression level at later time points compared to earlier time points indicates an efficacy of the lipid-based nanoparticle delivery; or
(ii) an increased or unchanged SLC46A3 expression level at later time points compared to earlier time points indicates that the lipid-based nanoparticle delivery is unlikely to be effective.

Any suitable lipid-based nanoparticle therapy may be implicated in the methods of this embodiment, as deemed appropriate by attending medical personnel. In one embodiment of these embodiments, the lipid-based cancer therapy nanoparticle is selected from the lipid-based cancer therapy nanoparticles shown in Table 1.

In one embodiment, the subject has an increased or unchanged SLC46A3 expression level at the later time point compared to the earlier time point, wherein the method further comprises administering to the subject a non-lipid cancer therapy nanoparticle to treat or diagnose the cancer. In another embodiment, the subject has an increased or unchanged SLC46A3 expression level at the later time point compared to the earlier time point, wherein the method further comprises administering to the subject an increased dosage or total amount of the lipid-based cancer nanoparticle to treat or diagnose the cancer.

In a second aspect, the disclosure provides methods of treating cancer in a subject, the method comprising
(a) identifying a subject with cancer cells, such as malignant cells, that have a normal or increased SLC46A3 expression level as compared to historical controls, and
(b) delivering to said subject an amount effective to treat the cancer of:
(i) a composition to decrease SLC46A3 expression; and
(ii) a lipid-based cancer therapy nanoparticle.

As disclosed above and in the examples, the inventors have identified SLC46A3 expression reduction as a means to improve lipid-based nanoparticle cancer therapies. Any suitable composition capable of decreasing SLC46A3 RNA and/or protein expression may be used, including but not limited to small molecules, proteins, SLC46A3 antibodies, inhibitory polypeptides, and/or inhibitory nucleic acids. Similarly, any suitable lipid-based cancer therapy nanoparticle may be used, including but not limited to those disclosed in Table 1. The composition to decrease SLC46A3 expression and the lipid-based cancer therapy nanoparticle may be administered together or separately, and may be administered at about the same time, simultaneously, or at different times. For example, the composition to decrease SLC46A3 expression could be dosed separately as a pretreatment prior to administration of the lipid-based cancer therapy nanoparticle.

In one embodiment, the methods comprise delivering to the subject a lipid-based nanoparticle comprising the composition to decrease SLC46A3 expression and a chemotherapeutic to treat the cancer cells. In another embodiment, the composition to decrease SLC46A3 expression comprises SLC46A3-specific siRNA, shRNA, CRISPR, mRNA, miRNA, or oligonucleotides, or any other SLC46A3-specific inhibitory nucleic acid-based strategy. In a specific embodiment, the composition to decrease SLC46A3 expression is SLC46A3-specific siRNA. The sequence of the SLC46A3 gene is provided in SEQ ID NO:1 and the protein sequence is provided in SEQ ID NO:2. It is well within the level of skill in the art, based on the teachings herein, to generate SLC46A3-inhibitory nucleic acids or other SLC46A3 inhibitors (such as antibodies).

As used herein for all embodiments, "treat" or "treating" means accomplishing one or more of the following: (a) reducing the size or volume of tumors and/or metastases in the subject; (b) limiting any increase in the size or volume of tumors and/or metastases in the subject; (c) increasing survival or progression-free survival; (d) reducing the severity of symptoms associated with cancer; (e) limiting or preventing development of symptoms associated with cancer; and (f) inhibiting worsening of symptoms associated with cancer.

Any suitable lipid-based nanoparticle may be used in the methods of each aspect of the disclosure. In one embodiment, the lipid-based nanoparticle comprises a liposomal nanoparticle. As used herein, a liposomal nanoparticle is a spherical nanoparticle vesicle containing at least one lipid bilayer (hydrophobic membrane) surrounding an aqueous (hydrophilic) core.

In one embodiment, the liposomal nanoparticle comprises an anionic or neutral liposomal nanoparticle. In a specific embodiment, the liposomal nanoparticle comprises an anionic liposomal nanoparticle. Any suitable anionic or neutral liposomal nanoparticle may be used.

In one embodiment, the anionic liposomal nanoparticle comprises an electrostatic coating. Any suitable electrostatic coating may be used. In one embodiment, the electrostatic coating comprises poly-L-arginine (PLR). In various other embodiments, the electrostatic coating comprises one or more polyanions selected from the group consisting of polyacrylic acid (PAA), poly-L-aspartate (PLD), poly-L-glutamate (PLE), hyaluronate (HA), dextran sulfate (DXS), fucoidan (FUC), alginate (ALG), chondroitin sulfate (CS), carboxylate ions, and sulfate ions. In specific embodiments, the electrostatic coating comprises PLE and/or PLD.

In another embodiment, the liposomal nanoparticle comprises polyethylene glycol (PEG). Any suitable amount of PEG may be used in the lipid-based nanoparticles. In one embodiment, the PEG is present at between about 0.3 mol % and about 25 mol %. In other embodiments, the liposomal nanoparticle comprises PEG at between about 0.5 mol % and 25 mol %, about 1 mol % and 25 mol %, about 2.5 mol % and 25 mol %, or about 5 mol % and 25 mol %.

The examples provide extensive disclosure of specific lipid-based nanoparticle compositions. In one embodiment, the liposomal nanoparticle core comprises DSPC:DSPG:Cholesterol:DSPE, wherein DSPC is 1,2-distearoyl-sn-glycero-3-phosphocholine, DSPG is 1,2-distearoyl-sn-glycero-3-phospho-(1'-rac-glycerol), and DSPE is 1,2-distearoyl-sn-glycero-3-phosphoethanolamine. In one such embodiment, the DSPC:DSPG:Cholesterol:DSPE are present in a molar ratio of about 31:31:31:6 mol %. In another embodiment, the liposomal nanoparticle core comprises DSPC:Cholesterol:DSPE-PEG(2000) carboxylic acid:DSPE; wherein PEG is polyethylene glycol and 2000 refers to the degree of polymerization. In one such embodiment, the DSPC:Cholesterol:DSPE-PEG(2000) carboxylic acid:DSPE are present in a molar ratio of about 55.67:33.3:5:6 6 mol %, or in a molar ratio of about 35.67:33.3:25:6 mol %.

In another embodiment, the liposomal nanoparticle core comprises DSPC:Cholesterol:PEG_PE:DSPE. In one such embodiment, the DSPC:Cholesterol:PEG_PE:DSPE are present in a molar ratio of about 53.8:39.9:0.3:6 mol %.

In one embodiment, the liposomal nanoparticle core comprises soy PC:cholesterol:PEG_PE:DSPE. In another such embodiment, the soy PC:cholesterol:PEG_PE:DSPE are present in a molar ratio of about 49:40:5:6 mol %

In a further embodiment, the liposomal nanoparticle comprises a composition as detailed in Table 2.

In another embodiment, the lipid-based nanoparticle comprises a solid lipid nanoparticle. As used herein, a "solid lipid nanoparticle" is a nanoparticle comprised of lipids, possessing a lipid core stabilized by surfactants that can encapsulate/solubilize therapeutic components, including but not limited to nucleic acids. In various embodiments, the solid lipid nanoparticle core comprises an ionizable, neutral, or cationic nanoparticle. In other embodiments, the solid lipid nanoparticle core comprises an ionizable, neutral, or cationic lipids, In one embodiment, the solid lipid nanoparticle core comprises DLinMC3DMA:DSPC:DMG-PEG2000:cholesterol. In another embodiment, the DLinMC3DMA:DSPC:DMG-PEG2000:cholesterol are present in a molar ratio of about 50:10:1.5:38.5. In a further embodiment, the DLinMC3DMA:DSPC:DMG-PEG2000:cholesterol are present in a molar ratio of about 23.2:4.6:0.7:71.4

The lipid-based nanoparticle may be of any mean diameter wherein they are nanoparticles as defined herein. In one embodiment, liposomal nanoparticle comprises a mean diameter between about 50 nm and 200 nm.

In all embodiments, the lipid-based nanoparticle may be surface functionalized to include any "cargo" of interest. In one embodiment, the lipid-based nanoparticle may comprise a reactive group for covalent linkage of a cargo. Any suitable reactive group may be used, as is know to those of skill in the art. Any cargo suitable for an intended purpose may be used, including but not limited to a diagnostic, a therapeutic, a detectable molecule (i.e.: radioactive, fluorescent, luminescent, or other detectable group), etc.

For all methods of the disclosure, the subject may be any suitable subject that may benefit from the methods of the disclosure, including but not limited to mammalian subjects. In one embodiment, the subject is a human subject.

In a third aspect, the disclosure provides compositions for treating cancer, the composition comprising
  (a) an inhibitor of SLC46A3 expression; and
  (b) a lipid-based chemotherapeutic-containing nanoparticle.

The compositions may be used, for example, in the therapeutic methods of the disclosure.

In one embodiment, the inhibitor of SLC46A3 expression is selected from the group consisting of an SLC46A3-specific siRNA, shRNA, CRISPR, mRNA, miRNA, or oligonucleotide; or any other SLC46A3-specific inhibitory nucleic acid-based strategy. In a specific embodiment, the inhibitor of SLC46A3 expression comprises SLC46A3-specific siRNA. In one embodiment, the inhibitor of SLC46A3 expression is present within or on the chemotherapeutic-containing nanoparticle.

All embodiments and combinations of embodiments of the lipid-based nanoparticles disclosed for the method aspects of the disclosure are equally applicable in the compositions of the disclosure.

In a fourth aspect, the disclosure provides methods of identifying subjects suitable for enrollment in a clinical trial for nanoparticle cancer therapy, comprising the following steps:
a) determining expression levels of SLC46A3 in a plurality of cells from multiple subjects diagnosed with cancer;
b) further determining whether the SLC46A3 expression levels from said patients are increased or decreased levels of expression as compared to historical controls, and
c) identifying as subjects suitable for enrollment in a clinical trial for nanoparticle cancer therapy those patients with decreased SLC46A3 expression levels compared to historical controls.

All embodiments and combinations of embodiments disclosed for the first three aspects of the disclosure are applicable in this fourth aspect of the disclosure.

EXAMPLES

Summary

To accelerate the translation of cancer nanomedicine, we hypothesize that integrated genomic screens will improve understanding of the cellular processes governing nanoparticle trafficking. We developed a massively parallel high-throughput screening method leveraging barcoded, pooled cancer cell lines annotated with multi-omic data to investigate cell association patterns across a nanoparticle library spanning a range of formulations with clinical potential. This approach identified both the materials properties and cell-intrinsic features mediating nanoparticle-cell association. Coupling the data with machine learning algorithms, we constructed genomic nanoparticle trafficking networks and identified nanoparticle-specific biomarkers. We engineered cell lines to validate SLC46A3 as a biomarker whose expression inversely predicts liposomal nanoparticle uptake both in vitro and in vivo. Our work establishes the power of massively parallel pooled cell screens for nanoparticle delivery and enables the identification and utilization of biomarkers to rationally design nanoformulations for specific patient populations.

Nanoparticle (NP)-based therapeutics have enormous potential for personalized cancer therapy as they can encapsulate a range of therapeutic cargos including small molecules, biologics and, more recently, nucleic acids.(1, 2) Therapy-loaded NPs can be designed to prevent undesired degradation of the cargo, increase circulation time, and direct drugs specifically to target tumors. There have been notable successes in clinical translation of nanomedicines, including liposomal formulations of doxorubicin (Doxil) and irinotecan (Onivyde®).(3) These formulations extend the half-life of the active agent and have the potential to lower toxicity, but do not efficiently accumulate in tumors. (4, 5)

In the era of precision medicine, with the desire to deliver molecularly targeted and gene-based therapies to specific subcellular compartments within cancer cells, it is imperative to holistically probe the structure-function relationship of NPs as they relate to cellular interactions.

To comprehensively capture pan-cancer complexities and enable the statistical power to link NP association with cell intrinsic characteristics, we developed a competitive phenotypic screen to assess associations of a curated NP library across hundreds of cancer cell lines simultaneously. By pooling and plating 488 DNA barcoded cancer cell lines in a single well, we screened the interactions of a range of NP formulations with varied core compositions, surface chemistries, and diameters. We observed that NP core composition has a dominating influence on cell-specific interactions of the studied parameters. Coupling our biomarker findings with k-means clustering, we constructed genomic interaction networks associated with NP engagement, enabling the identification and connection of genes associated with the binding, recognition, and subcellular trafficking of distinct NP formulations. Moreover, through the use of univariate analyses and random forest algorithms, we identified that the gene SLC46A3 holds significant value as a predictive, NP-specific biomarker. We further validated SLC46A3 as a negative regulator of liposomal NP uptake in vitro and in vivo. The strategy outlined herein identifies cellular features underlying nanoparticle engagement, adding a new dimension to the study of cancer nanomedicine.

Screening Nanoparticle Association with Pooled Cell Lines

To screen hundreds of cancer cell lines simultaneously for NP-cancer cell line association patterns, we cultured pooled DNA-barcoded mixtures of cells (referred to herein as PRISM cells) and incubated them with fluorescent NPs. We then implemented a fluorescence-activated cell sorting (FACS) adaptive gating strategy to sort cell populations into four bins (quartiles, A-D) based on fluorescence signal as a proxy for the extent of NP-cell association. Experimental parameters were optimized to ensure sufficient cell number and barcode representation post-cell sorting and NPs were incubated for 4 and 24 hours.

For this screen, we designed a modular NP library to capture the effects of NP core composition, surface chemistry, and size on cell interactions. This panel of 35 NPs encompassed both clinical and experimental formulations. Specifically, anionic liposomes were formulated and electrostatically coated with cationic poly-L-arginine (PLR) followed by a series of polyanions. The polyanions were selected for their synthetic (polyacrylic acid, PAA), semi-synthetic (poly-L-aspartate, PLD; poly-L-glutamate, PLE), or natural (hyaluronate, HA; dextran sulfate, DXS; fucoidan, FUC; alginate, ALG; chondroitin sulfate, CS) origin as well as the inclusion of both carboxylate and sulfate ions. These same electrostatic coatings were used to modify polymeric NP cores (polylactide-co-glycolide, PLGA) to test the effects of core composition on NP-cell interactions. We optimized formulations to obtain a diameter of approximately 100 nm for the liposome and PLGA formulations as the similar sizes would enable cross-core comparisons. We also included commercially manufactured fluorescent carboxylate- and sulfate-modified polystyrene (PS) nanoparticles in a range of diameters from 20-200 nm, enabling study of particle size and surface chemistry. Because of the clinical importance of polyethylene glycol (PEG)-containing formulations, PEGylated versions of liposome, PLGA, and PS particles were prepared, including the drug-free versions of two commercial formulations, liposomal doxorubicin (Doxil) and liposomal irinotecan (Onyvide®). The latter two formulations are denoted as LIPO-5% PEG* and LIPO-0.3% PEG*, respectively. All of the nanoparticles examined exhibited negative or neutral net charge, as the focus of this work is on systemic nanoparticle delivery systems. Positively charged nanoparticles have been shown to undergo nonspecific charge interactions with cells and proteins, leading to toxicity and premature clearance in vivo. Dynamic light scattering (DLS) was used to characterize the diameter, zeta potential, and polydispersity index (Tables 2-3) of this NP library.

TABLE 2

Nanoparticle formulation summary. Core compositions, polyelectrolyte identities and amounts used in the synthesis of the NP library are provided.

| Name | Core | Core Composition | Layer 1 | Layer 1-Wt. Eq. | Layer 2 | Layer 2-Wt. Eq. |
|---|---|---|---|---|---|---|
| LIPO - bare | Liposome | 31:31:31:6 mol % DSPC:DSPG:Cholesterol:DSPE | — | — | — | — |
| LIPO - PLR | Liposome | 31:31:31:6 mol % DSPC:DSPG:Cholesterol:DSPE | PLR | 0.3 | — | — |
| LIPO - PLD | Liposome | 31:31:31:6 mol % DSPC:DSPG:Cholesterol:DSPE | PLR | 0.3 | PLD | 0.65 |
| LIPO- PLE | Liposome | 31:31:31:6 mol % DSPC:DSPG:Cholesterol:DSPE | PLR | 0.3 | PLE | 0.65 |
| LIPO- PAA | Liposome | 31:31:31:6 mol % DSPC:DSPG:Cholesterol:DSPE | PLR | 0.3 | PAA | 0.2 |
| LIPO - HA | Liposome | 31:31:31:6 mol % DSPC:DSPG:Cholesterol:DSPE | PLR | 0.3 | HA | 1.2 |
| LIPO - ALG | Liposome | 31:31:31:6 mol % DSPC:DSPG:Cholesterol:DSPE | PLR | 0.3 | ALG | 1.2 |
| LIPO - DXS | Liposome | 31:31:31:6 mol % DSPC:DSPG:Cholesterol:DSPE | PLR | 0.3 | DXS | 0.65 |
| LIPO - FUC | Liposome | 31:31:31:6 mol % DSPC:DSPG:Cholesterol:DSPE | PLR | 0.3 | FUC | 1.2 |
| LIPO - CS | Liposome | 31:31:31:6 mol % DSPC:DSPG:Cholesterol:DSPE | PLR | 0.3 | CS | 1.2 |
| LIPO - 5% PEG | 5% PEG Liposome | 55.67:33.3:5:6 mol % DSPC:Cholesterol:DSPE-PEG(2000) carboxylic acid:DSPE | — | — | — | — |
| LIPO - 25% PEG | 25% PEG Liposome | 35.67:33.3:25:6 mol % DSPC:Cholesterol:DSPE-PEG(2000) carboxylic acid:DSPE | — | — | — | — |
| LIPO - EGFR | 25% PEG Liposome | 35.67:33.3:25:6 mol % DSPC:Cholesterol:DSPE-PEG(2000) carboxylic acid:DSPE | — | — | — | — |
| LIPO - IGG | 25% PEG Liposome | 35.67:33.3:25:6 mol % DSPC:Cholesterol:DSPE-PEG(2000) carboxylic acid:DSPE | — | — | — | — |
| LIPO - 0.3% PEG* | Onivyde | 53.8:39.9:0.3:6 mol % DSPC:Cholesterol:PEG_PE:DSPE | — | — | — | — |
| LIPO - 5% PEG* | Doxil | 49:40:5:6 mol % soy PC:cholesterol:PEG_PE:DSPE | — | — | — | — |
| PLGA - bare | PLGA | Resomer RG502H Poly(D,L-lactide-glycolide) | — | — | — | — |
| PLGA - PLR | PLGA | Resomer RG502H Poly(D,L-lactide-glycolide) | PLR | 0.4 | — | — |
| PLGA - PLD | PLGA | Resomer RG502H Poly(D,L-lactide-glycolide) | PLR | 0.4 | PLD | 0.65 |
| PLGA - PLE | PLGA | Resomer RG502H Poly(D,L-lactide-glycolide) | PLR | 0.4 | PLE | 0.65 |
| PLGA - PAA | PLGA | Resomer RG502H Poly(D,L-lactide-glycolide) | PLR | 0.4 | PAA | 0.2 |
| PLGA - HA | PLGA | Resomer RG502H Poly(D,L-lactide-glycolide) | PLR | 0.4 | HA | 1.2 |
| PLGA - ALG | PLGA | Resomer RG502H Poly(D,L-lactide-glycolide) | PLR | 0.4 | ALG | 1.2 |
| PLGA - DXS | PLGA | Resomer RG502H Poly(D,L-lactide-glycolide) | PLR | 0.4 | DXS | 0.65 |
| PLGA - FUC | PLGA | Resomer RG502H Poly(D,L-lactide-glycolide) | PLR | 0.4 | FUC | 1.2 |
| PLGA - CS | PLGA | Resomer RG502H Poly(D,L-lactide-glycolide) | PLR | 0.4 | CS | 1.2 |
| PLGA - 50% PEG | PEG-PLGA | Poly(D,L-lactide-glycolide) 50:50-b-PEG | — | — | — | — |
| PS-200nm COOH | Polystyrene | Yellow-green carboxylate-modified fluosphere | — | — | — | — |
| PS-100nm COOH | Polystyrene | Yellow-green carboxylate-modified fluosphere | — | — | — | — |
| PS-40nm COOH | Polystyrene | Yellow-green carboxylate-modified fluosphere | — | — | — | — |
| PS-20nm COOH | Polystyrene | Yellow-green carboxylate-modified fluosphere | — | — | — | — |
| PS-200nm SO3 | Polystyrene | Yellow-green sulfate fluosphere | — | — | — | — |
| PS-20nm SO3 | Polystyrene | Yellow-green sulfate fluosphere | — | — | — | — |
| PS-200nm PEG | Polystyrene | Yellow-green carboxylate-modified fluosphere | — | — | — | — |
| PS-100nm PEG | Polystyrene | Yellow-green carboxylate-modified fluosphere | — | — | — | — |
| PS-40nm PEG | Polystyrene | Yellow-green carboxylate-modified fluosphere | — | — | — | — |
| PS-20nm PEG | Polystyrene | Yellow-green carboxylate-modified fluosphere | — | — | — | — |

TABLE 3

NP size, uniformity, and charge were measured using dynamic light scattering (DLS). Data is represented as the mean and standard deviation of three technical repeats, with the exception of formulations marked with a dagger (†). Size and PDI of these formulations were characterized using the Wyatt Dyna Pro Plate Reader, and only a single value for those measurements is presented.

| Name | Z-Average Size (nm) | Number Mean Size (nm) | PDI | Zeta Potential |
|---|---|---|---|---|
| LIPO - bare | 117.7 ± 4.0 | 78.4 ± 7.2 | 0.3 ± 0.1 | −45.0 ± 6.3 |
| LIPO - PLR | 154.4 ± 1.3 | 104.5 ± 6.1 | 0.1 ± 0.0 | 53.6 ± 1.1 |
| LIPO - PLD | 132.3 ± 1.6 | 92.2 ± 10.2 | 0.1 ± 0.0 | −61.0 ± 1.1 |
| LIPO - PLE | 179.4 ± 0.7 | 124.6 ± 7.0 | 0.2 ± 0.0 | −47.2 ± 0.3 |
| LIPO - PAA | 136.8 ± 2.7 | 104.0 ± 1.7 | 0.1 ± 0.0 | −61.6 ± 1.4 |
| LIPO - HA | 159.7 ± 2.3 | 111.2 ± 4.6 | 0.1 ± 0.0 | −46.6 ± 0.8 |
| LIPO - ALG | 150.2 ± 4.0 | 101.5 ± 3.0 | 0.1 ± 0.0 | −78.7 ± 5.2 |
| LIPO - DXS | 133.2 ± 2.9 | 108.7 ± 6.4 | 0.1 ± 0.0 | −74.2 ± 2.5 |
| LIPO - FUC | 155.5 ± 3.9 | 67.8 ± 37.5 | 0.1 ± 0.0 | −61.2 ± 0.7 |
| LIPO - CS | 163.9 ± 3.7 | 120.8 ± 1.3 | 0.2 ± 0.0 | −61.9 ± 1.1 |
| LIPO - 5% PEG† | — | 101.9 | 0.2 | −53.1 ± 1.1 |
| LIPO - 25% PEG† | — | 94.2 | 0.2 | −46.0 ± 1.2 |
| LIPO - EGFR† | — | 131.1 | 0.3 | −45.2 ± 3.2 |
| LIPO - IGG† | — | 99.2 | 0.3 | −37.7 ± 2.7 |
| LIPO - 0.3% PEG* | 132.2 ± 1.6 | 75.5 ± 2.1 | 0.2 ± 0.0 | −50.2 ± 3.2 |
| LIPO - 5% PEG*† | — | 106.2 | 0.3 | −46.3 ± 1.6 |
| PLGA - bare | 175.4 ± 5.3 | 117.7 ± 10.4 | 0.1 ± 0.0 | −37.4 ± 0.8 |

TABLE 3-continued

NP size, uniformity, and charge were measured using dynamic light scattering (DLS). Data is represented as the mean and standard deviation of three technical repeats, with the exception of formulations marked with a dagger (†). Size and PDI of these formulations were characterized using the Wyatt Dyna Pro Plate Reader, and only a single value for those measurements is presented.

| Name | Z-Average Size (nm) | Number Mean Size (nm) | PDI | Zeta Potential |
|---|---|---|---|---|
| PLGA - PLR | 189.0 ± 4.3 | 123.1 ± 7.5 | 0.2 ± 0.0 | 63.5 ± 0.4 |
| PLGA - PLD | 173.4 ± 3.1 | 111.4 ± 1.9 | 0.2 ± 0.0 | −53.0 ± 1.4 |
| PLGA - PLE | 157.8 ± 2.7 | 88.6 ± 10.9 | 0.2 ± 0.0 | −40.8 ± 0.9 |
| PLGA- PAA | 168.8 ± 4.2 | 105.8 ± 4.0 | 0.1 ± 0.0 | −62.8 ± 2.3 |
| PLGA - HA | 164.3 ± 4.1 | 90.7 ± 32.8 | 0.1 ± 0.0 | −45.0 ± 0.4 |
| PLGA - ALG | 197.1 ± 6.1 | 116.0 ± 14.7 | 0.2 ± 0.0 | −59.4 ± 1.4 |
| PLGA - DXS | 172.4 ± 10.5 | 118.1 ± 6.8 | 0.1 ± 0.0 | −61.7 ± 0.2 |
| PLGA - FUC | 172.1 ± 9.1 | 96.8 ± 21.1 | 0.2 ± 0.0 | −53.3 ± 2.2 |
| PLGA - CS | 205.0 ± 3.9 | 93.2 ± 18.8 | 0.2 ± 0.0 | −47.0 ± 2.4 |
| PLGA - 50% PEG | 170.3 ± 1.8 | 104.5 ± 4.4 | 0.2 ± 0.0 | −37.5 ± 0.8 |
| PS-200nm COOH | 204.3 ± 3.2 | 172.0 ± 8.8 | 0.1 ± 0.0 | −36.7 ± 2.5 |
| PS-100nm COOH | 123.2 ± 2.1 | 102.9 ± 3.0 | 0.0 ± 0.0 | −48.6 ± 2.6 |
| PS-40nm COOH | 65.7 ± 1.4 | 48.7 ± 5.7 | 0.1 ± 0.0 | −36.1 ± 1.3 |
| PS-20nm COOH | 79.0 ± 1.8 | 35.4 ± 2.3 | 0.3 ± 0.0 | −55.5 ± 1.9 |
| PS-200nm SO3 | 257.6 ± 3.8 | 223.7 ± 7.1 | 0.1 ± 0.0 | −36.6 ± 0.6 |
| PS-20nm SO3 | 118.8 ± 7.3 | 35.2 ± 8.6 | 0.3 ± 0.0 | −13.1 ± 0.4 |
| PS-200nm PEG | 303.8 ± 16.8 | 202.6 ± 48.2 | 0.3 ± 0.0 | −4.4 ± 2.9 |
| PS-100nm PEG | 125.9 ± 2.1 | 100.5 ± 2.8 | 0.1 ± 0.0 | −4.9 ± 0.6 |
| PS-40nm PEG | 97.2 ± 1.3 | 67.3 ± 3.9 | 0.1 ± 0.0 | −7.8 ± 0.5 |
| PS-20nm PEG | 131.8 ± 8.2 | 51.3 ± 11.6 | 0.3 ± 0.0 | −3.6 ± 0.5 |

To ensure that our methods led to robust and meaningful data we selected an anti-epidermal growth factor receptor (EGFR) antibody as an active targeting control. A nonlethal EGFR antibody or IgG isotype control was covalently incorporated onto a liposome via a PEG tether.

After incubation with the NP library and fluorescence-activated cell sorting, cells were lysed, and the DNA barcodes were amplified, sequenced, and deconvoluted according to previously detailed protocols.(14, 27) After quality control analysis of technical (n=2) and biologic (n=3) replicates, all 488 cell lines met quality control measures and were carried forward for downstream analyses.

A probabilistic model was developed and applied to the data to infer the relative distribution of each cell line into the pre-determined bins (A-D) for each NP formulation. The probability of a cell from a given cell line falling into a given bin is used to represent those distributions, i.e., $P_A+P_B+P_C+P_D=1$. The technical details and the model's implementation are presented in the Supplementary Text section. Given the concordance of the inferred probabilities among the biologic replicates, we collapsed the replicates through their arithmetic average. Probabilities were then summarized using a weighting factor alpha ($\alpha$) to calculate a weighted average (WA) for each NP-cell line pair: $WA=-\alpha P_A-P_B+P_C+\alpha P_D$ in which a higher WA implies higher NP-cell association and vice versa. We trialed a range of weighting factors ($\alpha=2, 10, 20$ and $100$) and found that downstream results were unchanged with the higher $\alpha$ values, and therefore, $\alpha=2$ was used for subsequent analyses.

Cancer cells distinguish nanoparticles based on core composition Pearson-based unsupervised hierarchical clustering of pairwise WAs identified NP core material as a strong determinant of cell association, with the three core materials tested (liposomal, PLGA and PS) forming distinct clusters. This result was unexpected as we hypothesized surface chemistry to be a larger predictor of NP-cell interactions. Principal component analysis (PCA) similarly identified these core specific trends at both the 4 and 24 hour time points. Further analysis within each core material did reveal surface chemistry dependent trends, though they were more subtle than core-based clustering.

In contrast, no clusters were apparent when PCA was performed based on cell line, indicating that cancer cells of the same lineage did not have similar NP-association trends). Heterogeneity in NP-cell association in proliferating cells has been attributed to various aspects of cell growth and metabolism. To ensure that differential cell proliferation did not confound our results, we performed a parallel growth experiment with the same pooled cells and found no correlation between estimated doubling time and WA.

Cell-Intrinsic Features Mediate Nanoparticle Trafficking

We applied data from the Cancer Cell Line Encyclopedia (CCLE) to identify genomic features that act as predictive biomarkers for NP-cell association. To do this, we employed both univariate analyses and a random forest algorithm to correlate the baseline molecular features of each cell line (cell lineage; gene copy number; messenger RNA, microRNA, protein or metabolite abundance; function-damaging, hotspot or missense mutations) with NP association.

EGFR-Targeting Compounds Identify Relevant Biomarkers with High Confidence

Using univariate analysis for all CCLE features, we identified EGFR gene expression and protein abundance as the two most significantly correlated hits ($q=4\times10^{-100}$ and $q=4\times10^{-76}$, respectively) with anti-EGFR antibody, but much less significantly ($q=6\times10^{-9}$ and $q=4\times10^{-10}$, respectively) associated with the isotype control.

In EGFR-conjugated liposomes, these same hits were also identified more significantly ($q=6\times10^{-21}$ and $q=2\times10^{-18}$, respectively) than the IgG control ($q=3\times10^{-9}$ and $q=3\times10^{-6}$, respectively). The statistical significance of EGFR biomarkers was lower for the antibody-conjugated liposome than the free antibody, which may be due to steric blockage introduced by covalently linking an antibody to a NP surface that may interfere with binding to its target. Thus, we demonstrated the ability to quantitatively compare expected biomarker targets of both free antibodies and antibody-conjugated NPs using our platform. This method of analysis will provide therapeutic insights in the design of antibody-drug conjugates, specifically in evaluating the effects of conjugation site or linker chemistry.

Biomarker Number and Significance are Influenced by Nanoparticle Properties

We employed univariate analysis to correlate association and CCLE features for each NP formulation, thresholding q-values less than $1\times10^{-10}$. Selection of this cutoff was guided by the IgG-conjugated antibody analysis, which returned few hits above this threshold. For liposomal NPs, we observed that the number of significant biomarkers was higher at 4 h than 24 h. We believe this may be indicative of active uptake processes, established to take place within the first few hours of NP-cell interactions, whereas at 24 hours, we may be capturing features associated with less specific interactions. We also observed that liposome surface modification influences the number and significance of biomarkers. Specifically, liposomes electrostatically coated with polysaccharides (HA, ALG, DXS, FUC, CS) had the highest amount of associated biomarkers, which we hypothesize is due to the high degree of interactions between sugars and cell surface proteins as well as the potential for naturally occurring polysaccharides to interact with a wide range of cell surface elements. In line with this hypothesis, the addition of PEG, a well-established antifouling polymer, reduces the number and significance of associated biomarkers almost to zero. In contrast to the highly specific hits generated from EGFR-conjugated liposomes (formulated using 25% PEG liposomes), this abrupt decrease in significant biomarkers further indicates the ability of our platform to identify specific NP binding and recognition elements. In contrast to the liposomal formulations, PLGA formulations, regardless of surface modification, resulted in few biomarkers at either time point. Lastly, a high number of significant biomarkers was associated with both carboxylated and sulfated PS NPs included in our screen, though there was no time dependence, in contrast to the liposomal formulation. While this result was initially surprising, as the PS formulations are made of synthetic polystyrene polymers, meaningful biological interactions with anionic polystyrenes, both in polymer and particle form, have been reported. Specifically, it was described that these systems have the appropriate mix of hydrophobicity and anionic charge character to interact favorably with trafficking proteins, including the caveolins.

NP Biomarkers are Connected and Create Trafficking Networks

We additionally identified predictive biomarkers for the tested NP formulations using a random-forest algorithm. We annotated these candidate biomarkers to include the categories of gene expression, gene copy number, or protein abundance. Data from the 4 h time point was chosen for this analysis based on the EGFR-related hits for liposomes, which were more significant at 4 h than at 24 h. As we were interested in applying this approach to identify cellular features positively correlated with uptake (e.g., increased expression of trafficking proteins), hits negatively correlated with NP association were removed from this analysis. Next, we used K-means clustering to visualize biomarkers based on their relative importance and presence across formulations. Clusters 1 and 2 contained many hits shared across NP formulations and were especially enriched for liposomal and PS NPs. These 205 genes and proteins were input into a database(40-42) to generate a protein-protein interaction (PPI) network that was found to be highly interconnected (PPI enrichment p-value $<1\times10^{-16}$). Notably, the network is enriched in proteins found in the plasma membrane, extracellular region, and extracellular matrix (false discovery rate [FDR]=$8\times10^{-12}$, $3\times10^{-9}$, and $3\times10^{-8}$, respectively) based on enrichment analysis with gene ontology (GO) localization datasets.(43-45) The identification of overlapping biomarkers that are localized to the cell surface and have established protein-protein interactions led us to hypothesize that these proteins are important in early NP trafficking. Enrichment analyses using GO molecular functions datasets showed enrichment in numerous binding processes, giving further credence to this theory. These results serve as a framework for the comprehensive investigation of cellular processes important for NP engagement, which may prove useful for fundamental trafficking studies and target identification.

SLC46A3 is a Negative Regulator of Liposomal NP Uptake

Evaluating univariate results across NP formulations, we identified one biomarker with a strong, inverse relationship with liposomal NP association: expression of solute carrier family 46 member 3 (SLC46A3), a lysosomal transporter. This is, to our knowledge, the first description of SLC46A3 as a NP-specific biomarker. We sought to validate the predictive power of SLC46A3 expression for liposomal NP association.

Figure 5A:
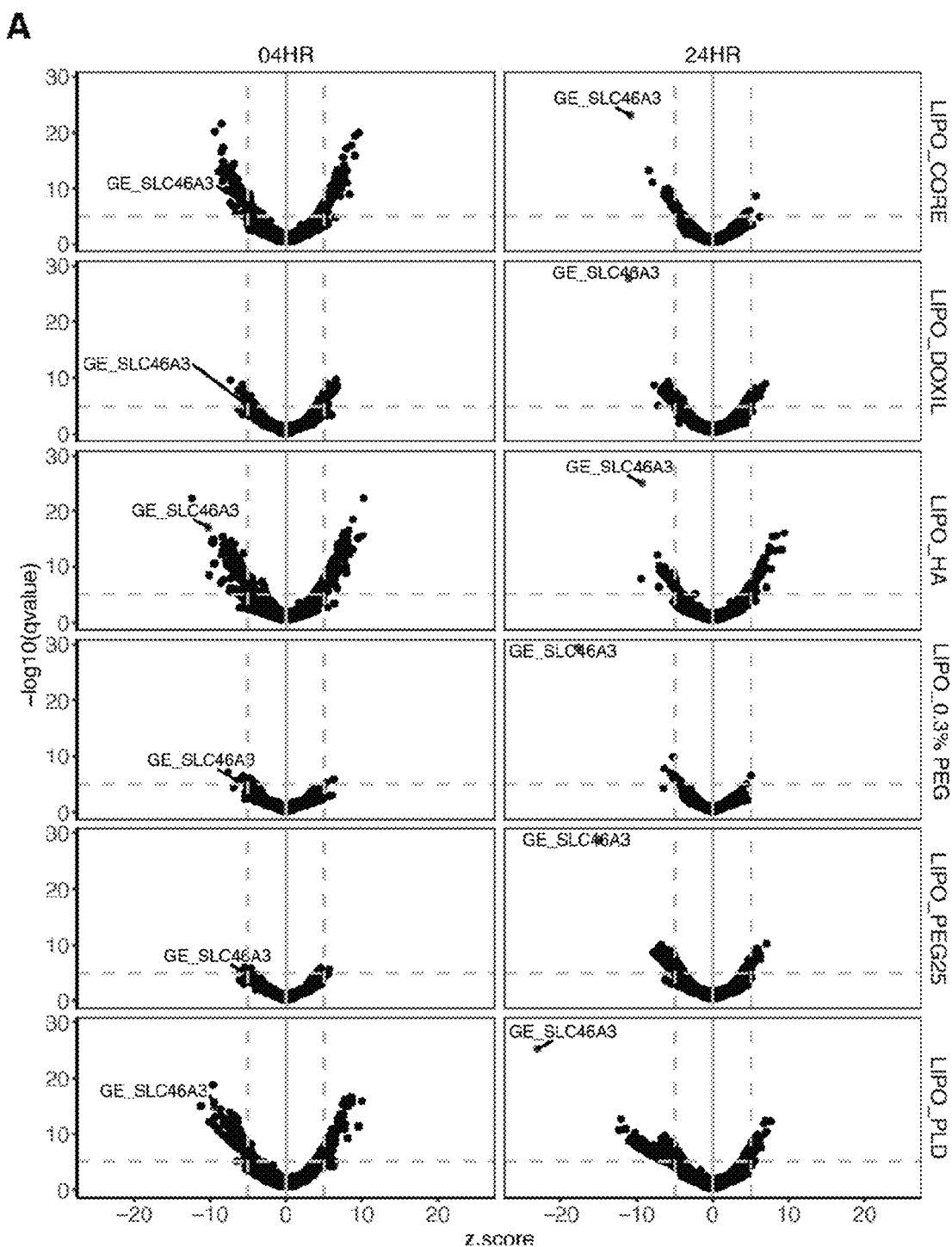
FIG. 5 Expanded SLC46A3 univariate analysis and lineage analysis. (A) Gene expression of SLC46A3 was a significant biomarker with negative z-score for liposome (LIPO) formulations with and without PEG and more significant at 24 h than at 4 h. Volcano plots for six liposomal NP formulations highlighting the position of SLC46A3 biomarker, which has higher significance and more negative z-score at 24 h compared to 4 h. SLC46A3 expression was not a top hit for (B) PLGA or (C) PS formulations at either time point. (D) The inverse relationship of SLC46A3 expression was observed for tested LIPO formulations regardless of cancer cell lineage.
Figure 5D:
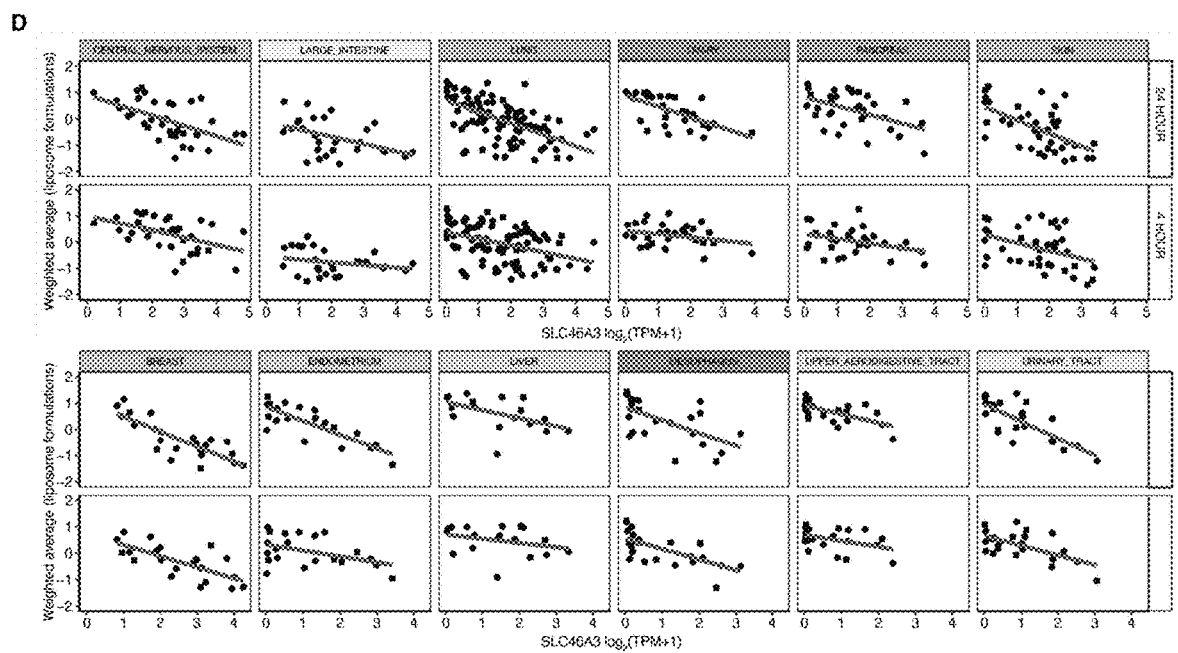

SLC46A3 expression was the most significant hit on univariate analysis and also the top ranked random forest feature for each liposomal NP tested at 24 h, regardless of surface modification (FIGS. 1A and 5). This inverse relationship between SLC46A3 expression and NP association was found to be specific to liposomal NPs, and not observed with PLGA or PS NPs, and was maintained regardless of cancer cell lineage (FIGS. 1B and 5).

Figure 6A:
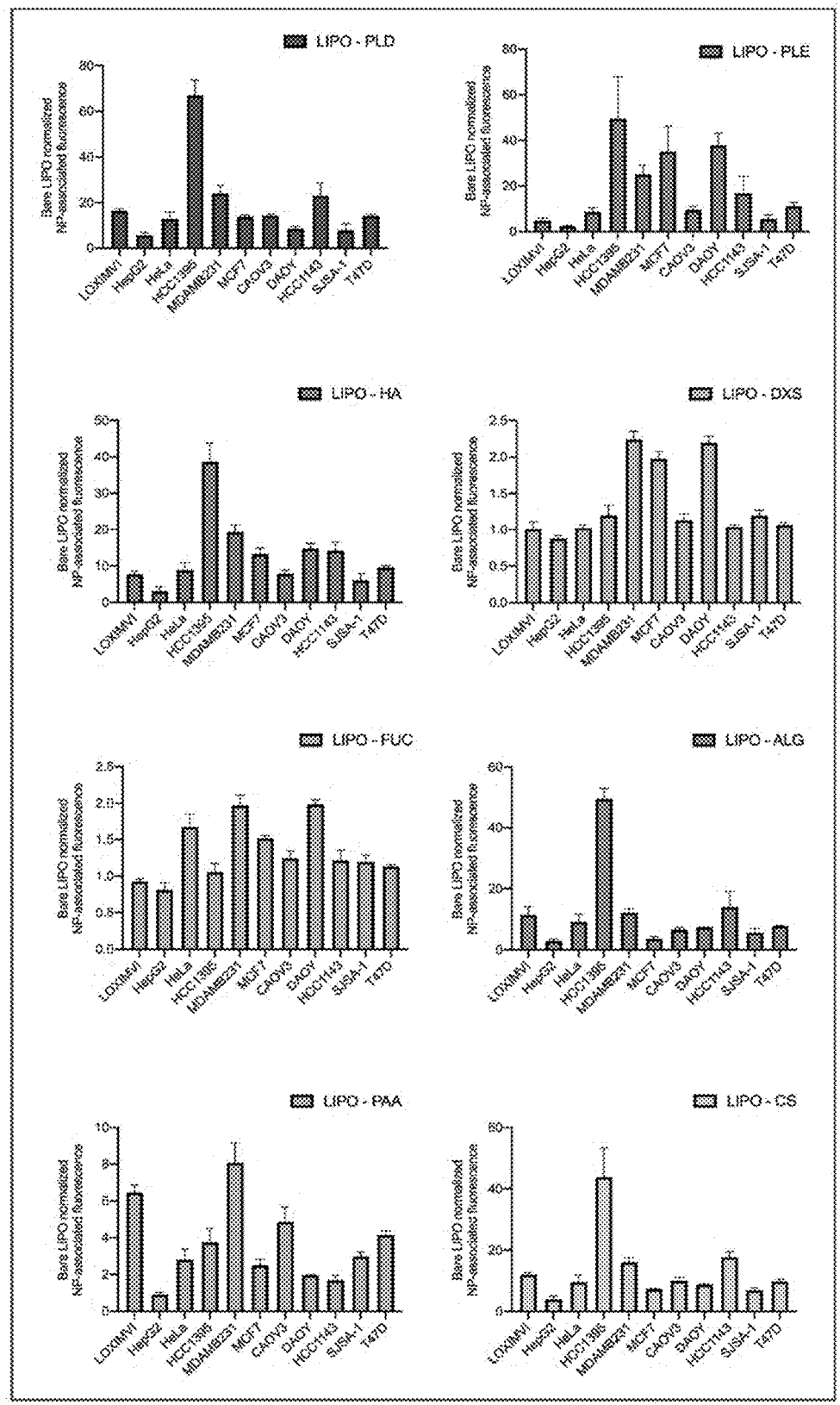
FIG. 6. Expanded non-pooled screening via flow cytometry of cell interactions with (A) liposomal and (B) PS NP formulation at 24 h. Data is represented as the mean and standard deviation of four biological replicates.
Figure 6B:
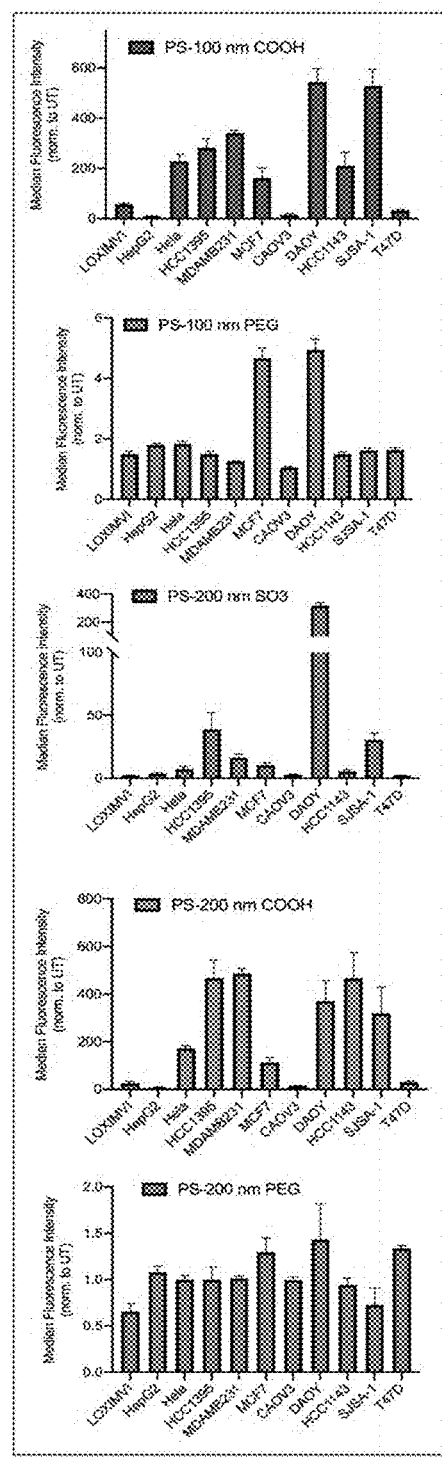

We selected nine cancer cell lines from the pool and four additional cell lines, spanning multiple lineages, with a range of native SLC46A3 expression levels for screening in a non-pooled fashion (FIG. 1C-D). Analogous to the pooled screen, individual cell lines were profiled using flow cytometry and NP-associated fluorescence was quantified after 24 h incubation (FIGS. 13D and 6). In line with observations from pooled screening, the inverse relationship between liposome association and native SLC46A3 expression was maintained, suggesting that SLC46A3 may play a key role in trafficking of liposomal NPs.

To further functionally probe whether SLC46A3 expression level governs NP association, we selected two cancer cell lines from the pooled screen that displayed strong phenotypes (FIG. 2A). The melanoma cell line LOXIMVI exhibited high association and breast cancer cell line T47D exhibited low association with liposomal NP formulations (FIG. 2B). We developed a toolkit using these cell lines by knocking out SLC46A3 in T47D cells and inducing overexpression in LOXIMVIs (FIGS. 7A-H).

Figure 2C:
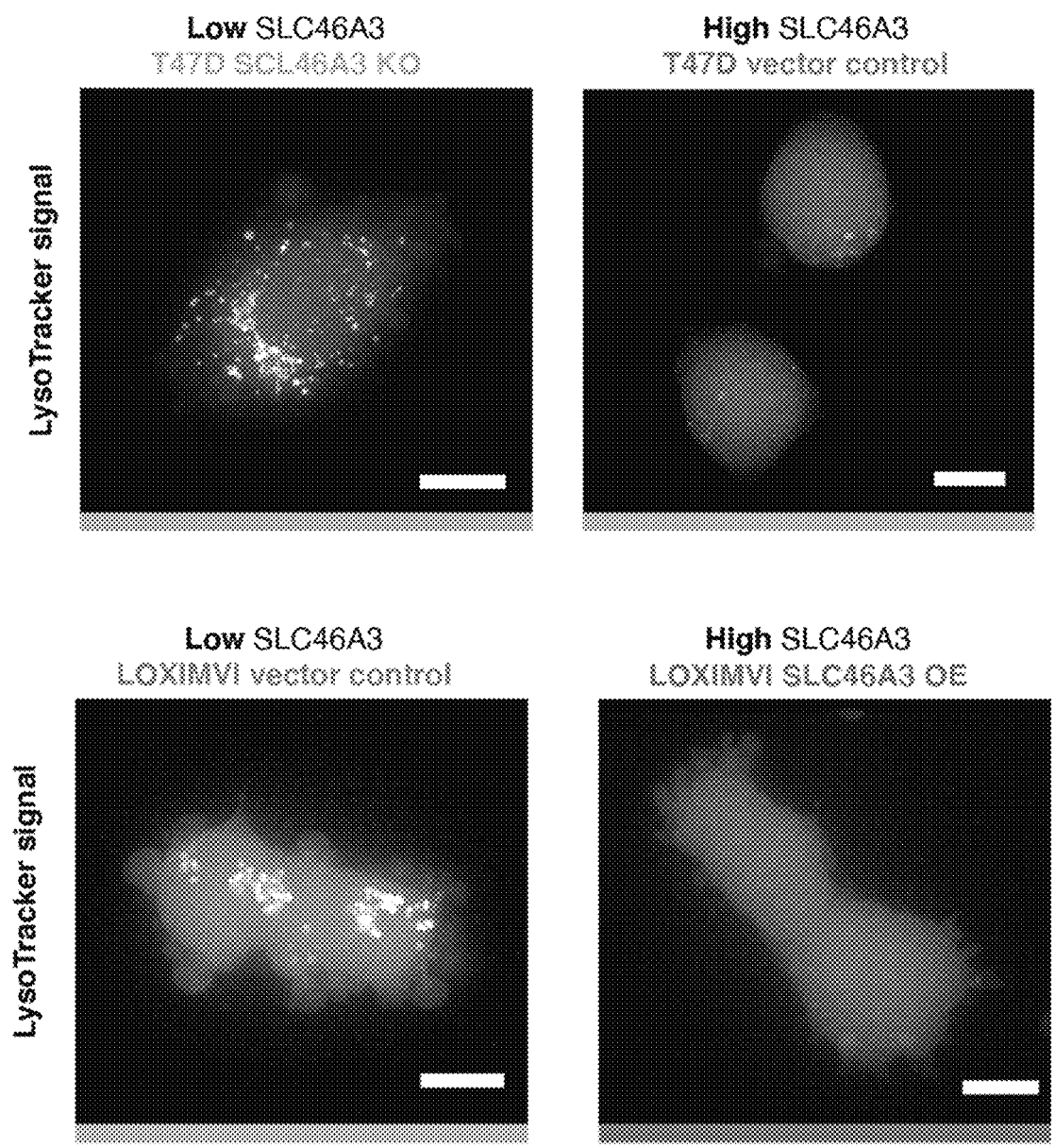
FIG. 2. Modulating SLC46A3 expression in cancer cell lines is sufficient to negatively regulate interaction with liposome NP formulations. (A) T47D and LOXIMVI cells have high and low SLC46A3 expression, respectively, with respect to SLC46A3 expression levels represented in the cell line pool. (B) LOXIMVI cells have predominantly high association with all tested liposomal NP formulations and T47D cells have low association with all tested liposomal NP formulations. (C) Representative micrographs of signal in engineered cell lines showing endolysosomal compartments. Scale bars=10 μm. (D) Using lentivirus to overexpress SLC46A3 in LOXIMVI cells and CRISPR/Cas9 to knock out SLC46A3 in T47D cells, we show that modulation results in significantly changed liposome association, as determined via flow cytometry (** $p<0.001$, Kruskal-Wallis test), NP-associated fluorescence is defined as median fluorescence intensity normalized to untreated cells. Data is represented as the mean and standard deviation of four biological replicates. (E) These shifts in NP association were consistently observed across all tested liposomes, independent of surface modification. No shifts were observed with PLGA or PS formulations.

As SLC46A3 is a protein associated with lysosomal membranes, we utilized LysoTracker® dye to evaluate the effect of SLC46A3 modulation on endolysosomal compartments in both T47D and LOXIMVI engineered cell lines (FIG. 2C). We observed an SLC46A3 expression level-dependent change: cells with higher SLC46A3 levels (T47D-vector control, LOXIMVI-SLC46A3 OE) exhibited more brightly dyed endolysosomal compartments compared to their low SLC46A3 expression counterparts (T47D-SLC46A3 knockout, LOXIMVI-vector control).

Figure 7:
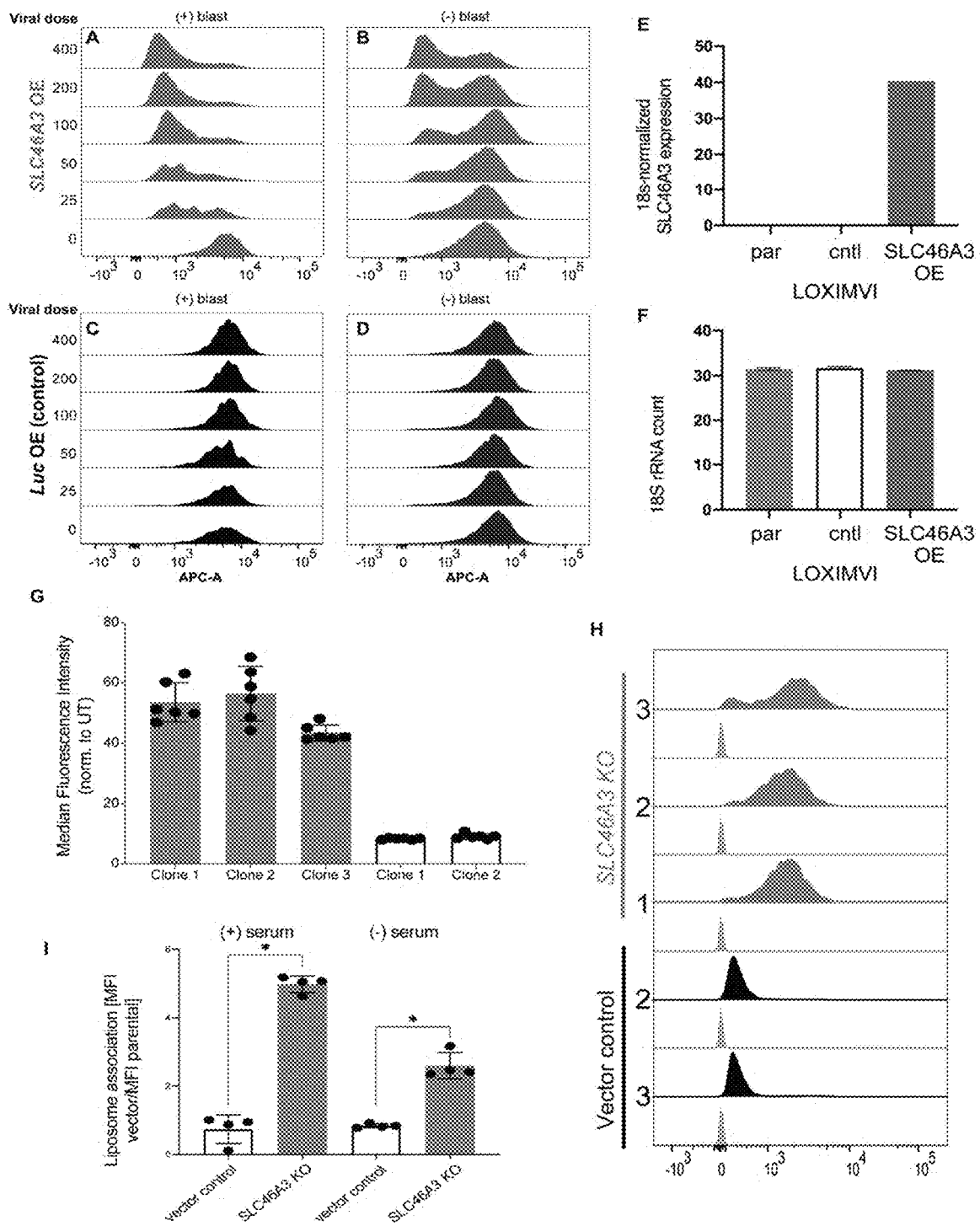
FIG. 7. Flow cytometry profiling of engineered cell lines after SLC46A3 modulation. After transduction (lentiviral dose, 0-400 μL), LOXIMVI were cultured (A, C) with and (B, D) without blasticidin (blast). Cells were then incubated with liposomal NPs (bare LIPO) for 24 h prior to flow cytometry analysis with NP-associated fluorescence detected in the APC-A channel. (A, B) A virus concentration-dependent decrease in liposome-cell association is observed but not in (C, D) the vector control cells. (E) Summary of qPCR profiling of SLC46A3 in LOXIMVI cells. (F) Ribosomal RNA count of cell samples used to generate PCR data in panel E. (G) Quantification of liposomal association with clonal T47D-SLC46A3 knockouts generated using the CRISPR/Cas9 system. Three clonal populations were tested for the SLC46A3 knockout to ensure a consistent phenotype was observed. Data is represented as the mean and standard deviation of six biological replicates. (H) Representative flow histograms of clonal populations treated with liposomal NPs for 24 h; with NP-associated fluorescence detected in the APC-A channel. (I) Flow cytometry analysis reveals SLC46A3-related trends in liposomal NP association with T47D cells are maintained with and without serum present in cell culture medium. T47D cells were cultured either with or without 10% FBS and treated with liposomal NPs for 24 h. Flow cytometry was used to quantify the liposome-cell association extent, and median fluorescence intensity (MFI) values for the vector control and SLC46A3 KO cells were divided by the MFI of the liposome-treated parental T47D cells. Significant increases in liposome association (*, $p<0.05$, Mann-Whitney) were observed in SLC46A3 KO in both groups. Data is represented as the mean and standard deviation of four biological replicates.

Overexpression of SLC46A3 in LOXIMVI cells significantly abrogated interaction with bare liposomes (p=0.006) using flow cytometry profiling (FIG. 2D). The T47D-SLC46A3 knockout cell line demonstrated significantly increased association with bare liposomes compared to parental or vector control lines (p=0.0017, FIG. 2D). We further confirmed that these trends are generalizable across a range of surface functionalized liposomes (FIG. 2E). Moreover, no significant changes in NP association were observed for PLGA and PS NPs. We also confirmed that the presence of serum proteins in cell culture media does not abrogate this trend (FIG. 7I). Taken together, these data indicate modulation of SLC46A3 alone in cancer cells is sufficient to negatively regulate association and uptake of liposomal NPs.

As flow cytometry does not provide spatial information with respect to NP-cell interactions, we employed imaging cytometry to characterize NP localization in a high throughput manner (FIG. 3A-F). We selected four representative formulations: three liposomal NPs to probe the relationship of SLC46A3 expression with liposome trafficking; and one PLGA NP formulation with a common outer layer.

Figure 3:
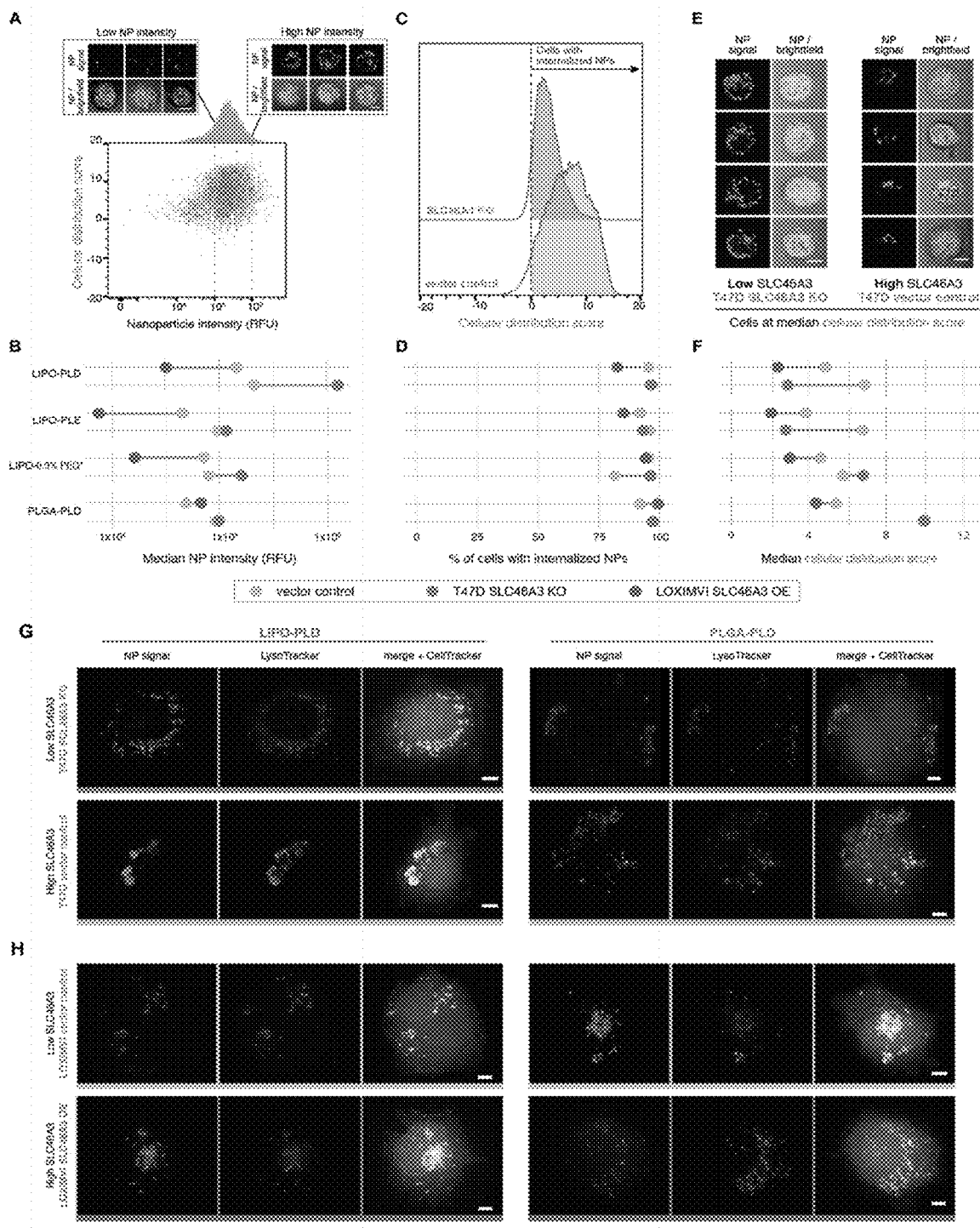
FIG. 3. High throughput imaging cytometry confirms NP internalization and reveals SLC46A3 dependent changes to intracellular trafficking. (A) Imaging cytometry was used to investigate the intensity (x-axis) and distribution (y-axis) of NPs in a high-throughput manner. Bivariate density plot of n=10,000 cells (T47D-vector control) after 24 h incubation with LIPO-PLD NPs, with representative cell images at low and high NP signal. (B) Cellular distribution patterns of NPs were scored such that scores greater than 0 indicate cells with internalized NPs. Representative data from LIPO-PLD NPs in engineered T47D cells are shown. (C) Representative cell images at the median cellular distribution score for engineered T47D cells treated with LIPO-PLD NPs. (D) Quantification of median intensity of tested NP formulations in engineered T47D and LOXIMVI cell lines demonstrated SLC46A3-dependent changes. (E) NPs remained predominantly internalized independent of SLC46A3 expression levels. (F) Shifts in the median cellular distribution scores were observed in response to SLC46A3 modulation. Live cell micrographs of (G) T47D-vector control and T47D-SLC46A3 knockout cells and (H) LOXIMVI-vector control and LOXIMVI-SLC46A3 OE cells incubated with LIPO-PLD and PLGA-PLD NPs for 24 h. Scale bar=5 μm.

Consistent with trends observed by flow cytometry, we observed an inverse relationship between NP intensity and SLC46A3 expression for liposomal, but not PLGA, NPs (FIG. 3A-B). Using brightfield images, we applied a mask to investigate cellular localization of NPs. All tested formulations were internalized, and this did not change with SLC46A3 modulation (FIG. 3C-D), so we hypothesize that SLC46A3 plays a role in retention of NPs rather than directly blocking uptake.

We investigated localization of NPs by scoring NP signal based on distribution within each cell (FIG. 3E-F). We observed stark differences in median cellular distribution scores of liposomal NPs in relation to SLC46A3 expression levels in T47D cells. This was not observed for PLGA NPs, mimicking the previously observed core-specific relationship between NP-cell association and SLC46A3 expression. Changes in this score, though less pronounced, were also observed for liposomal NPs in LOXIMVI cells.

Figure 8A:
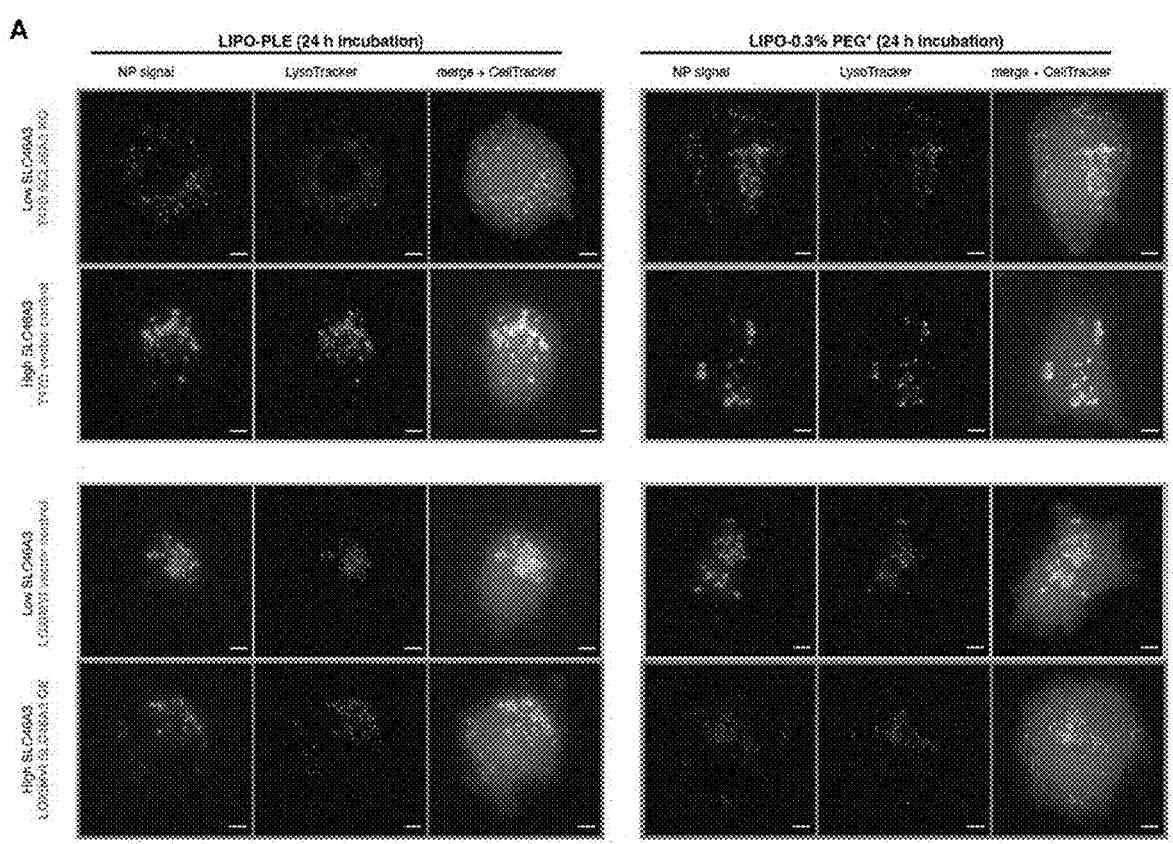
FIG. 8. Liposomal nanoparticles exhibit SLC46A3-dependent changes in intracellular trafficking. Live cell micrographs of (A) LIPO-PLE and LIPO-0.3% PEG* NPs incubated with engineered T47D and LOXIMVI cells for 24 h. (B) Live cell micrographs of LIPO-PLD NPs incubated with T47D and LOXIMVI cells for 4 h. Scale bar=5 μm.
Figure 8B:
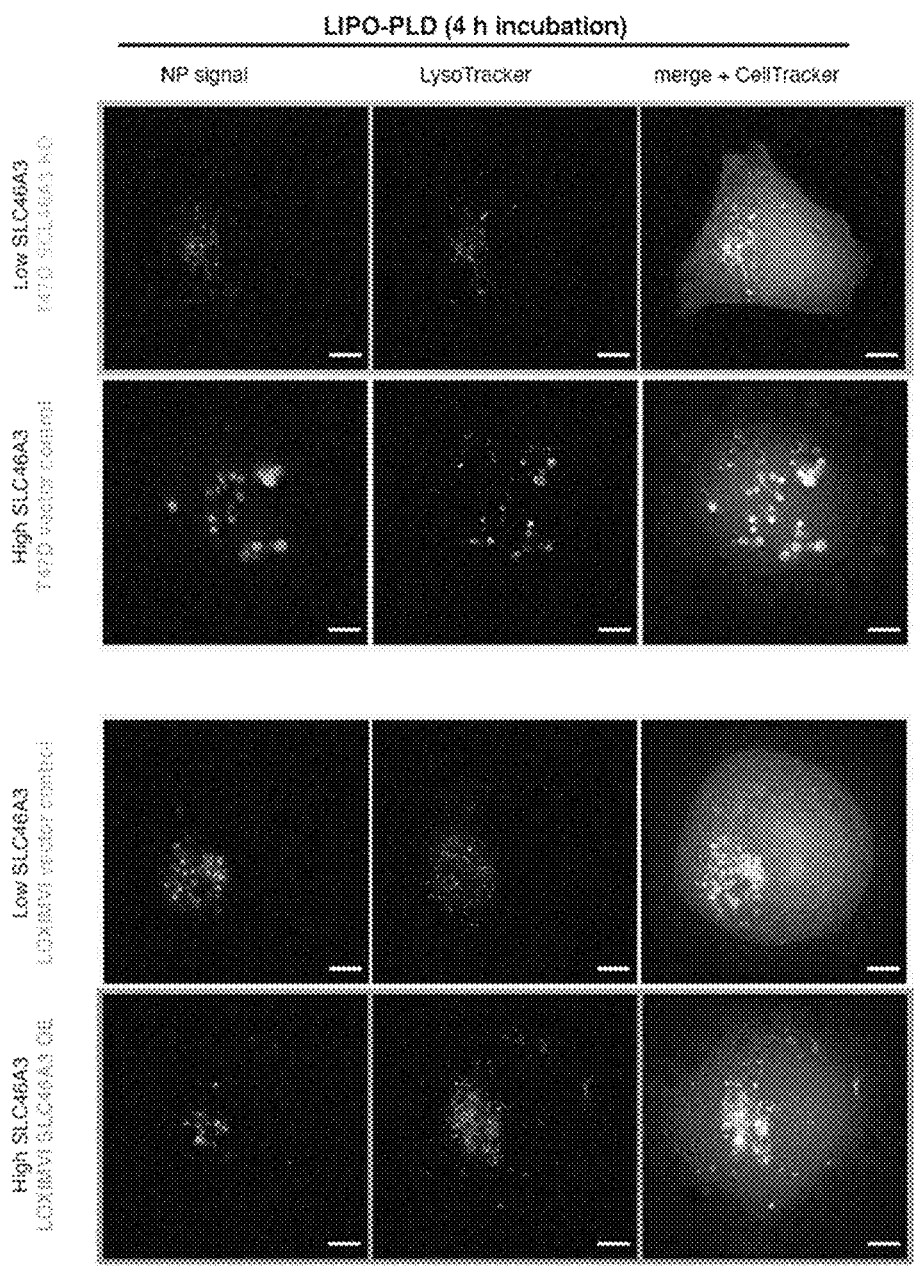

To confirm these findings with higher spatial resolution, we employed deconvolution microscopy of live cells and incorporated a lysosomal stain to observe changes in intracellular trafficking (FIG. 3G-H). NPs appeared uniformly distributed within T47D-SLC46A3 KO cells, co-localizing with endolysosomal vesicles. In contrast, LIPO-PLD NPs were localized to large endolysosomal clusters in T47D-vector control cells. This trend was also observed for LIPO-PLE and LIPO-0.3% PEG* NPs and at the earlier time point of 4 h (FIG. 8). Changes in localization were not observed for the tested PLGA PLD NPs. This again indicates a NP core-dependent relationship with SLC46A3.

In the engineered LOXIMVI cell lines, we also observed co-localization of liposomal NPs with endolysomal signal. However, predictable changes in NP localization were not detected, in line with smaller changes in median cellular distribution scores. Taken together, these results suggest that the relationship between SLC46A3 expression and NP uptake is twofold: SLC46A3 predictably and negatively regulates the amount of liposomal NPs accumulating within a cell and modulates subcellular trafficking in certain contexts.

Knockdown of SLC46A3 with siRNA Leads to Predictable Changes in NP Delivery

We have shown that knockout of SLC46A3 using CRISPR/Cas9 leads to increased nanoparticle-cell association for liposomes. Knocking down SLC46A3 expression with small interfering RNA (siRNA) results in a statistically significant increase in nanoparticle-cell association ($p<0.001$). The data is provided in Table 4, further confirming the genotype-phenotype relationship of SLC46A3 and liposomal nanoparticle delivery.

TABLE 4

Nanoparticle association expressed as MFI in the T47D cell line after 24 hr treatment with siRNA directed against SLC46A3 or scrambled siRNA control.

| siRNA Treatment | NP Treatment | Median fluorescence intensity (MFI) | Standard Deviation | n | P value, 2-tailed |
| --- | --- | --- | --- | --- | --- |
| siRNA_SLC46A3 | 0.3% PEG Liposome | 11692.86 | 1366.55 | 7 | 0.0006 |
| siScramble | 0.3% PEG Liposome | 5398.43 | 1876.48 | 7 | |
| siRNA_SLC46A3 | No nanoparticle | 87.80 | 1.93 | 3 | >0.05 |
| siScramble | No nanoparticle | 87.40 | 0.00 | 3 | |

Liposome Retention and Accumulation Remains SLC46A3-Dependent In Vivo

To evaluate the potential clinical utility of SLC46A3 as a negative regulator of liposomal NP delivery, we tested in vivo delivery of an FDA-approved nanoparticle analog, the drug-free version of liposomal irinotecan (LIPO-0.3% PEG*), in mice bearing subcutaneous LOXIMVI flank tumors. NPs were administered via a one-time intratumoral (IT) injection or repeat intravenous (IV) administration to evaluate tumor retention and accumulation, respectively (FIG. 4A, FIG. 9).

NP signal was quantified both 4 and 24 h following IT administration. In line with our hypothesis, as well as in vitro NP-associated fluorescence data (FIG. 9A), we observed an inverse relationship between SLC46A3 expression and LIPO-0.3% PEG* NP retention that became more pronounced over time ($p=0.0115$, 4 h; $p=0.0002$, 24 h) (FIG. 4C-D, FIG. 9B-E). Moreover, these findings also align with our initial findings, in which SLC46A3 expression was a more significant biomarker at 24 h (q-value=$3.49\times10^{-30}$, Table 3, FIG. 5) than at 4 h (q-value=$1.47\times10^{-4}$, Table 3, FIG. 5).

To determine if this newly identified biomarker can be used to predictably govern accumulation of non-targeted NPs, which bear no specific functional ligands on their surface, following systemic administration, we quantified NP signal following IV injections. Notably, we observed a significant relationship between SLC46A3 and NP accumulation ($p=0.0019$) (FIG. 4D, FIG. 9F). This demonstrates the predictive power of SLC46A3 as a NP specific biomarker that holds true even in complex physiologic settings.

Together, these data highlight the real-world relevance of the screening assay in general as well as the utility of SLC46A3 in particular a clinically actionable biomarker.

SLC46A3 Expression Predicts mRNA Delivery Efficacy Via Solid Lipid Nanoparticles Given the strong relationship between SLC46A3 expression and liposomal nanoparticles, we hypothesized that the relationship would hold true for other lipid-based nanoparticles. Indeed, SLC46A3 expression is predictive of improved transfection via solid lipid nanoparticles containing messenger RNA encoding green fluorescent protein (GFP mRNA). Transfection efficiency as measured by median GFP fluorescence or % of cells GFP positive is decreased in LOXIMVI cells engineered to overexpress SLC46A3 compared to control. Data is shown in Table 5

TABLE 5

Transfection of engineered LOXIMVI cells after lipid nanoparticle delivery of GFP mRNA. Transfection is measured by median GFP fluorescence and % GFP positive cells. LNP1 formulation is 50:10:1.5:38.5 DLinMC3DMA:DSPC:DMG-PEG2000:cholesterol; LNP2 formulation is 23.2:4.6:0.7:71.4 DLinMC3DMA:DSPC:DMG-PEG2000:cholesterol. The N:P was held constant at 6 and all cells were dosed for 24 hours.

| LNP Formulation | mRNA dose (ng) | LOXIMVI control | | | LOXIMVI SLC46A3 OE | | |
|---|---|---|---|---|---|---|---|
| | | Median GFP Intensity | Std Dev | N | Median GFP Intensity | Std Dev | N |
| None | 0 | 17.1 | 0.8 | 3 | 17.1 | 0.8 | 3 |
| LNP1 | 200 | 2366.5 | 1243.8 | 2 | 530.0 | 167.4 | 3 |
| | 100 | 435.0 | 145.7 | 2 | 127.7 | 13.1 | 3 |
| | 50 | 90.5 | 26.2 | 2 | 105.5 | 33.3 | 3 |
| LNP2 | 200 | 640.3 | 31.0 | 3 | 408.0 | 52.3 | 2 |
| | 100 | 270.7 | 92.2 | 3 | 183.5 | 30.4 | 2 |
| | 50 | 193.3 | 33.4 | 3 | 102.6 | 16.1 | 2 |

| LNP Formulation | mRNA dose (ng) | LOXIMVI control | | | LOXIMVI SLC46A3 OE | | |
|---|---|---|---|---|---|---|---|
| | | % GFP positive | Std Dev | N | % GFP positive | Std Dev | N |
| None | 0 | 0.1 | 0.0 | 3 | 0.0 | 0.0 | 3 |
| LNP1 | 200 | 98.5 | 0.5 | 2 | 93.0 | 2.8 | 3 |
| | 100 | 90.9 | 5.3 | 2 | 62.3 | 4.1 | 3 |
| | 50 | 49.7 | 10.1 | 2 | 53.4 | 11.0 | 3 |
| LNP2 | 200 | 93.5 | 0.6 | 3 | 89.3 | 0.1 | 2 |
| | 100 | 81.9 | 7.8 | 3 | 71.6 | 3.5 | 2 |
| | 50 | 71.1 | 3.9 | 3 | 54.0 | 5.3 | 2 |

Discussion and Conclusions

This work represents the first high-throughput interrogation of NP-cancer cell interactions through the lens of multi-omics. Harnessing the power of pooled screening and high throughput sequencing, we developed and validated a platform to identify predictive biomarkers for NP interactions with cancer cells. We utilized this platform to screen a 35 member NP library against a panel of 488 cancer cell lines. This enabled the comprehensive study and identification of key parameters mediating NP-cell interactions, highlighting the importance of considering both nanomaterials and cellular features in concert.

Moreover, through the use of univariate analyses and random forest algorithms, we identified biomarkers correlated with NP association. The robust and quantitative nature with which we detected EGFR hits for antibody-targeted NPs shows the utility of this platform for the development and optimization of antibody-targeted therapeutics.

By clustering NP-specific biomarkers across formulations, we constructed interaction networks, identifying and connecting genes associated with NP binding, recognition, and subcellular trafficking. This provides the scientific community with a blueprint for the fundamental study of cellular processes mediating NP engagement, with applications for both basic and translational research.

We additionally identified gene expression of SLC46A3 as a negative regulator of liposomal NP uptake. We validated these findings in a panel of non-pooled cell lines and engineered cell lines with modulated SLC46A3 levels. Importantly, as all current FDA approved NPs for anticancer applications are liposomal formulations, there is significant potential for this biomarker to be quickly implemented in clinical studies with existing, approved formulations. To this end, we recapitulated our findings in an in vivo model using an analog of an FDA-approved liposomal NP formulation. Our findings present the key first step toward identifying and utilizing such NP-specific biomarkers.

In summary, we present a powerful platform to study NP-cancer cell interactions simultaneously through the use of pooled screening, genomics, and machine learning algorithms. This provides a new dimension to the study of cancer nanomedicine. Application of this platform will serve useful not only for the rational design of nanocarriers, but also for the identification of specific phenotypes primed to benefit from targeted drug delivery and nanomedicine.

REFERENCES AND NOTES

1. J. J. Shi, P. W. Kantoff, R. Wooster, O. C. Farokhzad, Cancer nanomedicine: progress, challenges and opportunities. *Nat. Rev. Cancer* 17, 20-37 (2017).
2. M. J. Mitchell, M. M. Billingsley, R. M. Haley, M. E. Wechsler, N. A. Peppas, R. Langer, Engineering precision nanoparticles for drug delivery. *Nat. Rev. Drug. Discov.* 20, 101-124 (2020).
3. S. Tran, P. J. DeGiovanni, B. Piel, P. Rai, Cancer nanomedicine: a review of recent success in drug delivery. *Clin. Transl. Med.* 6, 1-21 (2017).
4. S. Wilhelm, A. J. Tavares, Q. Dai, S. Ohta, J. Audet, H. F. Dvorak, W. C. W. Chan, Analysis of nanoparticle delivery to tumours. *Nat. Rev. Mater.* 1, 16014 (2016).
5. Y. H. Cheng, C. L. He, J. E. Riviere, N. A. Monteiro-Riviere, Z. M. Lin, Meta-Analysis of Nanoparticle Delivery to Tumors Using a Physiologically Based Pharmacokinetic Modeling and Simulation Approach. *ACS Nano* 14, 3075-3095 (2020).

6. Y. S. Youn, Y. H. Bae, Perspectives on the past, present, and future of cancer nanomedicine. *Adv. Drug Deliver. Rev.* 130, 3-11 (2018).
7. W. Poon, B. R. Kingston, B. Ouyang, W. Ngo, W. C. W. Chan, A framework for designing delivery systems. *Nat. Nanotechnol.* 15, 819-829 (2020).
8. W. Poon, Y. N. Zhang, B. Ouyang, B. R. Kingston, J. L. Y. Wu, S. Wilhelm, W. C. W. Chan, Elimination Pathways of Nanoparticles. *ACS Nano* 13, 5785-5798 (2019).
9. S. Correa et al., Tuning Nanoparticle Interactions with Ovarian Cancer through Layer-by-Layer Modification of Surface Chemistry. *ACS Nano* 14, 2224-2237 (2020).
10. N. Boehnke, S. Correa, L. Hao, W. Wang, J. P. Straehla, S. N. Bhatia, P. T. Hammond, Theranostic Layer-by-Layer Nanoparticles for Simultaneous Tumor Detection and Gene Silencing. *Angew. Chem. Int. Ed. Engl.* 59, 2776-2783 (2020).
11. N. Boehnke, K. J. Dolph, V. M. Juarez, J. M. Lanoha, P. T. Hammond, Electrostatic Conjugation of Nanoparticle Surfaces with Functional Peptide Motifs. *Bioconjug. Chem.* 31, 2211-2219 (2020).
12. J. E. Dahlman et al., Barcoded nanoparticles for high throughput in vivo discovery of targeted therapeutics. *Proc. Natl. Acad. Sci. U.S.A.* 114, 2060-2065 (2017).
13. B. Nogrady, How cancer genomics is transforming diagnosis and treatment. *Nature* 579, S10-S11 (2020).
14. C. N. Yu et al., High-throughput identification of genotype-specific cancer vulnerabilities in mixtures of barcoded tumor cell lines. *Nat. Biotechnol.* 34, 419-423 (2016).
15. S. M. Corsello et al., Discovering the anticancer potential of non-oncology drugs by systematic viability profiling. *Nat. Cancer* 1, 235-248 (2020).
16. S. Correa, N. Boehnke, E. Deiss-Yehiely, P. T. Hammond, Solution Conditions Tune and Optimize Loading of Therapeutic Polyelectrolytes into Layer-by-Layer Functionalized Liposomes. *ACS Nano* 13, 5623-5634 (2019).
17. S. Correa et al., Highly Scalable, Closed-Loop Synthesis of Drug-Loaded, Layer-by-Layer Nanoparticles. *Adv. Funct. Mater.* 26, 991-1003 (2016).
18. Z. J. Deng, S. W. Morton, E. Ben-Akiva, E. C. Dreaden, K. E. Shopsowitz, P. T. Hammond, Layer-by-Layer Nanoparticles for Systemic Codelivery of an Anticancer Drug and siRNA for Potential Triple-Negative Breast Cancer Treatment. *ACS Nano* 7, 9571-9584 (2013).
19. S. W. Morton, Z. Y. Poon, P. T. Hammond, The architecture and biological performance of drug-loaded LbL nanoparticles. *Biomaterials* 34, 5328-5335 (2013).
20. G. Decher, Fuzzy nanoassemblies: Toward layered polymeric multicomposites. *Science* 277, 1232-1237 (1997).
21. E. C. Dreaden et al., Tumor-Targeted Synergistic Blockade of MAPK and PI3K from a Layer-by-Layer Nanoparticle. *Clin. Cancer Res.* 21, 4410-4419 (2015).
22. E. C. Dreaden, S. W. Morton, K. E. Shopsowitz, J. H. Choi, Z. J. Deng, N. J. Cho, P. T. Hammond, Bimodal Tumor-Targeting from Microenvironment Responsive Hyaluronan Layer-by-Layer (LbL) Nanoparticles. *ACS Nano* 8, 8374-8382 (2014).
23. O. P. Oommen, C. Duehrkop, B. Nilsson, J. Hilborn, O. P. Varghese, Multifunctional Hyaluronic Acid and Chondroitin Sulfate Nanoparticles: Impact of Glycosaminoglycan Presentation on Receptor Mediated Cellular Uptake and Immune Activation. *ACS Appl. Mater. Inter.* 8, 20614-20624 (2016).
24. J. S. Suk, Q. G. Xu, N. Kim, J. Hanes, L. M. Ensign, PEGylation as a strategy for improving nanoparticle-based drug and gene delivery. *Adv. Drug Deliver. Rev.* 99, 28-51 (2016).
25. E. Frohlich, The role of surface charge in cellular uptake and cytotoxicity of medical nanoparticles. *Int. J. Nanomed.* 7, 5577-5591 (2012).
26. E. A. Berg, J. B. Fishman, Labeling Antibodies Using N-Hydroxysuccinimide (NHS)-Fluorescein. *Cold Spring Harb. Protoc.* 3, 229-231 (2019).
27. X. Jin et al., A metastasis map of human cancer cell lines. *Nature* 588, 331-336 (2020).
28. J. A. Kim, C. Aberg, A. Salvati, K. A. Dawson, Role of cell cycle on the cellular uptake and dilution of nanoparticles in a cell population. *Nat. Nanotechnol.* 7, 62-68 (2012).
29. C. Aberg, J. A. Kim, A. Salvati, K. A. Dawson, Reply to 'The interface of nanoparticles with proliferating mammalian cells'. *Nat. Nanotechnol.* 12, 600-603 (2017).
30. E. Panet et al., The interface of nanoparticles with proliferating mammalian cells. *Nat. Nanotechnol.* 12, 598-600 (2017).
31. P. Rees, J. W. Wills, M. R. Brown, C. M. Barnes, H. D. Summers, The origin of heterogeneous nanoparticle uptake by cells. *Nat. Commun.* 10 (2019).
32. J. Barretina et al., The Cancer Cell Line Encyclopedia enables predictive modelling of anticancer drug sensitivity (vol 483, pg 603, 2012). *Nature* 492, 290-290 (2012).
33. M. Ghandi et al., Next-generation characterization of the Cancer Cell Line Encyclopedia. *Nature* 569, 503-508 (2019).
34. K. Tsuchikama, Z. Q. An, Antibody-drug conjugates: recent advances in conjugation and linker chemistries. *Protein Cell* 9, 33-46 (2018).
35. J. Rejman, V. Oberle, I. S. Zuhorn, D. Hoekstra, Size-dependent internalization of particles via the pathways of clathrin- and caveolae-mediated endocytosis. *Biochem. J.* 377, 159-169 (2004).
36. S. Behzadi et al., Cellular uptake of nanoparticles: journey inside the cell. *Chem. Soc. Rev.* 46, 4218-4244 (2017).
37. Y. Shamay et al., P-selectin is a nanotherapeutic delivery target in the tumor microenvironment. *Sci. Transl. Med.* 8, 345 (2018).
38. G. Saravanakumar, D. G. Jo, J. H. Park, Polysaccharide-Based Nanoparticles: A Versatile Platform for Drug Delivery and Biomedical Imaging. *Curr. Med. Chem.* 19, 3212-3229 (2012).
39. J. Voigt, J. Christensen, V. P. Shastri, Differential uptake of nanoparticles by endothelial cells through polyelectrolytes with affinity for caveolae. *Proc. Natl. Acad. Sci. U.S.A.* 111, 2942-2947 (2014).
40. D. Szklarczyk et al., STRING v11: protein-protein association networks with increased coverage, supporting functional discovery in genome-wide experimental datasets. *Nucleic Acids Res.* 47, D607-D613 (2019).
41. C. von Mering, M. Huynen, D. Jaeggi, S. Schmidt, P. Bork, B. Snel, STRING: a database of predicted functional associations between proteins. *Nucleic Acids Res.* 31, 258-261 (2003).
42. B. Snel, G. Lehmann, P. Bork, M. A. Huynen, STRING: a web-server to retrieve and display the repeatedly occurring neighbourhood of a gene. *Nucleic Acids Res.* 28, 3442-3444 (2000).
43. D. Martin, C. Brun, E. Remy, P. Mouren, D. Thieffry, B. Jacq, GOToolBox: functional analysis of gene datasets based on Gene Ontology. *Genome Biol.* 5, R101 (2004).

44. M. Ashburner et al., Gene Ontology: tool for the unification of biology. *Nat. Genet.* 25, 25-29 (2000).
45. S. Carbon et al., The Gene Ontology resource: enriching a GOld mine. *Nucleic Acids Res.* 49, D325-D334 (2021).
46. K. J. Hamblett et al., SLC46A3 Is Required to Transport Catabolites of Noncleavable Antibody Maytansine Conjugates from the Lysosome to the Cytoplasm. *Cancer Res.* 75, 5329-5340 (2015).
47. C. K. Tsui et al., CRISPR-Cas9 screens identify regulators of antibody-drug conjugate toxicity. *Nat. Chem. Biol.* 15, 949-958 (2019).
48. K. Kinneer et al., SLC46A3 as a Potential Predictive Biomarker for Antibody-Drug Conjugates Bearing Noncleavable Linked Maytansinoid and Pyrrolobenzodiazepine Warheads. *Clin. Cancer Res.* 24, 6570-6582 (2018).
49. Q. Zhao et al., Increased expression of SLC46A3 to oppose the progression of hepatocellular carcinoma and its effect on sorafenib therapy. *Biomed. Pharmacother.* 114, 108864 (2019).
50. G. M. Li et al., Mechanisms of Acquired Resistance to Trastuzumab Emtansine in Breast Cancer Cells. *Mol. Cancer Ther.* 17, 1441-1453 (2018).
51. C. H. Adelmann et al., MFSD12 mediates the import of cysteine into melanosomes and lysosomes. *Nature* 588, 699-704 (2020).
52. S. Stern, B. Neun, NCL Method GTA-12. *NCI Hub*, doi:10.17917/YPTH-N396.
53. M. Stephens, False discovery rates: a new deal. *Biostatistics* 18, 275-294 (2017).
54. R Core Team, R: A language and environment for statistical computing. R Foundation for Statistical Compouting. https://www.R-project.org/.
55. H. Wickham, ggplot2: Elegant Graphics for Data Analysis. Use R, 1-212 (2009).
56. Y. Tang, M. Horikoshi, W. X. Li, ggfortify: Unified Interface to Visualize Statistical Results of Popular R Packages. *R. J.* 8, 474-485 (2016).
57. M. Horikoshi, Y. Tang, ggfortify: Data Visualization Tools for Statistical Analysis Results. https://CRAN.R-project.org/package=ggfortify (2016).

Supplemental Information

Materials and Methods

Materials
Reagents 1,2-distearoyl-sn-glycero-3-phospho-(1'-rac-glycerol) (sodium salt) (DSPG), 1,2-distearoyl-sn-glycero-3-phosphoethanolamine (DSPE), 1,2-distearoyl-sn-glycero-3-phosphocholine (DSPC), 1,2-dioleoyl-sn-glycero-3-ethylphosphocholine (chloride salt) (18:1 EPC), L-α-phosphatidylcholine (Soy-PC), 1,2-distearoyl-sn-glycero-3-phosphoethanolamine-N-[carboxy(polyethylene glycol)-2000] (sodium salt) (MPEG-2k-DSPE, for Ab liposomes), 1,2-distearoyl-sn-glycero-3-phosphoethanolamine-N-[methoxy (polyethylene glycol)-2000] (ammonium salt) (PEG_PE), and cholesterol were purchased from Avanti Polar Lipids. Sulfo-cyanine5 NHS ester and cyanine5 free acid were purchased from Lumiprobe. Methoxy PEG amine (HCl salt), MW 2000 Da (for PS PEGylation) was purchased from JenKem Technologies. Chloroform and methanol were purchased from TCI and Sigma, respectively. Poly(D,L-lactide-glycolide) (Resomer RG502H, 7 kDa:17 kDa) and Poly(D,L-lactide-glycolide) 50:50-b-PEG (10 kDa PLGA, 2 kDa PEG) were purchased from Sigma.

Non-glycosylated monoclonal human IgG1 antibody against human EGFR (hegfr-mab12, lot: EG12-39-01) and isotype control—Human IgG1 (bgal-mabl, lot: BG1-41-01) were purchased from InvivoGen. Human EGFR (Research Grade Cetuximab Biosimilar) antibody was purchased from R&D Biosystems. Poly-L-arginine hydrochloride (PLR200, 38.5 kDa), poly-L-aspartic acid sodium salt (PLD100, 14 kDa), and poly-L-glutamic acid sodium salt (PLE100, 15 kDa) were purchased from Alamanda Polymers. Sodium hyaluronate (40 kDa) was purchased from Lifecore Biomedical. Dextran sulfate (15 kDa), fucoidan (from fucus vesiculosus), and polyacrylic acid (8 kDa) were purchased from Sigma. Sodium alginate was purchased from NovaMatrix. Chondroitin sulfate A (10-30 kDa average MW) was purchased from Carbosynth Ltd. Yellow-green fluorescent polysytrene microspheres (Fluospheres), 5 M bioreagent grade NaCl solution, and 1 M bioreagent-grade HEPES were purchased from Fisher Scientific.

Whatman nuclepore polycarbonate hydrophilic membranes (400, 200, 100 and 50 nm sizes) were purchased from GE. All glassware was obtained from Chemglass. 5 mL Falcon brand round-bottom tubes with 35 μm cell strainer cap, 50/15 mL Falcon tubes and 50/5/2 mL DNA/Protein Eppendorf tubes were purchased from VWR. D02-E100-05-N and C02-E100-05-N tangential flow filtration filters were purchased from Repligen. Polystyrene semi-micro cuvettes for the Malvern Zetasizer™ were purchased from VWR and DTS1070 folded capillary cells were purchased directly from Malvern. Black, glass bottom 364 well plates for the Wyatt DLS were purchased directly from the Peterson (1957) Nanotechnology Core Facility.

RPMI-1640 (Invitrogen/Corning), and PBS solution pH 7.4 (Gibco) were purchased from Fisher Scientific. Heat inactivated fetal bovine serum (FBS), Tween20, Igepal™ CA-630, Trizma hydrochloride, and Potassium chloride solution (~1 M in $H_2O$) were purchased from Sigma. Proteinase K was purchased from Qiagen. Matrix Storage Blocks (96 well, 1 mL) were purchased from ThermoFisher. Tissue culture plasticware, trypsin EDTA, Accutase, and penicillin streptomycin were purchased from Corning. LabTek 8-chamber coverslips (cat. no. 155409), CellTracker™ Blue CMAC, CellTracker™ Orange CMRA, and LysoTracker™ Green were purchased from Fisher Scientific.

Cells

The generation and culture conditions of the stably barcoded and pooled cells (500 human cancer cell lines) are described in reference 16. The CAOV3, DAOY, HeLa, HepG2, HCC1395, HCC1143, MDA-MB-231, MCF7, SJSA-1, and SW948 cell lines were obtained from ATCC. The LOXIMVI and T47D cell lines were gifts from the Gertler Lab, and the Jurkat cell line was a gift from the Sabatini Lab. Cells were cultured at 37° C. with 5% $CO_2$. Cell line-specific culture information is provided in the SLC46A3 Validation Studies section below.

Methods

The nanoparticle-specific methods described below detail conditions utilized for synthesis and characterization and have been adapted in part from references 9, 10, 11, and 16.

Base Liposome Synthesis

Cholesterol and 1,2-distearoyl-sn-glycero-3-phosphocholine (DSPC) were dissolved in chloroform. 1,2-distearoyl-sn-glycero-3-phosphoethanolamine (DSPE) and 1,2-distearoyl-sn-glycero-3-phospho-(1'-rac-glycerol) (DSPG) were dissolved in a 65:35:8 mixture of chloroform, methanol and deionized water (milli-Q). A lipid mixture composed of 31 mol % DSPC, 31 mol % cholesterol, 31 mol % DSPG and 6 mol % DSPE was prepared in 50 mL round bottom flask and methanol was added dropwise until the solution cleared. The lipid solution was evaporated using a rotovap system under heat (60° C., water bath) until completely dry (<15 mBarr) to make a thin lipid film. A sonicator bath was filled with milliQ water and heated until >65° C. The round bottom flask containing the lipid film was partially submerged in the water bath and milliQ water was added to re-suspend the lipid film to a concentration of 2 mg lipid/mL solution. The liposome solution was sonicated for 1 minute and then removed for 1 minute. This process was repeated three times and then transferred to Avestin a liposome extruder. The extruder was connected to a Cole-Palmer Heated Recirculator Bath to maintain a temperature >65° C. throughout the extruder. The liposome solution was extruded through sequentially smaller nucleopore membranes until a 50-100 nm liposome was obtained. This usually required two passes through a stack of one 400 and one 200 nm membrane followed by two passes through one 100 nm membrane and two passes through a 50 nm membrane. These liposomes were fluorescently labeled through NHS-coupling of sulfo-cyanine NHS ester dye to DSPE headgroups according to the dye manufacturer (Lumiprobe) instructions. Lipid film generation, rehydration, extrusion, and dye labeling steps were similarly applied to all liposome formulations unless noted otherwise.

Tangential Flow Filtration (TFF)

To remove excess dye, crude nanoparticle solution was connected to a Spectrum Labs system using Teflon-coated tubing. D02-E100-05-N membranes were used to purify the particles until dye was no longer seen in the permeate. This usually required 15-volume equivalent washes to be collected in the permeate. Dye levels in the permeate were monitored by running samples on a Tecan plate reader. Samples were run at flow rates of 80 mL/min with size 16 tubing. Once purified, the sample was concentrated and then recovered by reversing the direction of the peristaltic pump. To improve nanoparticle yield, 1-3 mLs of water were run backwards through the tubing to recover any remaining particles. 1×PBS was used as the exchange buffer for the first five washes followed by milliQ water for the rest of the purification steps. Following TFF, liposomes were characterized for size and zeta using dynamic light scattering (see Characterization of Nanoparticles). For LbL synthesis, TFF was used for purification between after deposition of each polyelectrolyte layer, following the above procedure. Instead of PBS, only milliQ water was passed through the TFF for LbL NP purification.

Synthesis of PEGylated Liposomes

To make the lipid stocks, cholesterol, DSPC, DSPE-PEG (2000) carboxylic acid, PEG-PE, and soy PC were dissolved in chloroform while DSPE was dissolved in a 65:35:8 mixture of chloroform, methanol and deionized water (milliQ). For the 5% PEG formulation (LIPO-5% PEG), a lipid mixture composed of 55.67 mol % DSPC, 33.3 mol % cholesterol, 5 mol % DSPE-PEG(2000) carboxylic acid and 6 mol % DSPE was prepared in a 50 mL round bottom flask. For the 25% PEG formulation (LIPO-25% PEG), a lipid mixture composed of 35.67 mol % DSPC, 33.3 mol % cholesterol, 25 mol % DSPE-PEG(2000) carboxylic acid and 6 mol % DSPE was prepared in a 50 mL round bottom flask. For the drug-free formulation of liposomal irinotecan (LIPO-0.3% PEG*), a lipid mixture composed of 53.8 mol % DSPC, 39.9 mol % cholesterol, 0.3 mol % PEG-PE and 6 mol % DSPE was prepared in a 50 mL round bottom flask. Lastly, for the drug-free formulation of liposomal doxorubicin (LIPO-5% PEG*), a lipid mixture composed of 49 mol % soy PC, 40 mol % cholesterol, 5 mol % PEG-PE and 6 mol % DSPE was prepared in 50 mL round bottom flask. Methanol was added dropwise to all flasks until each mixture was clear. Lipid film generation, rehydration, extrusion, and dye labeling steps are described in the base liposome synthesis section. For the extrusion step, we note that the described PEGylated formulations were passed through one 400 and one 200 nm membrane followed by two passes through one 100 nm membrane.

PLGA Nanoparticle Synthesis

PLGA was dissolved at a concentration of 10 mg/mL in acetone and Cy5 free acid dye was dissolved at a concentration of 50 mg/mL in DMSO. 6 mL of milliQ water were added to a 20 mL scintillation vial and stirred gently on a plate. In a 2 mL Eppendorf tube, 2 ul of the dye was added to 1 mL of the PLGA solution, mixed and drawn into syringe with a 27-gauge needle attached. In the scintillation vial, the tip of the needle was submerged below the water line and the PLGA-Cy5 solution was slowly added to the water under constant stirring. The solution was let stir ~3 hours to allow for solvent evaporation. An additional 2 mL milliQ water were added the solution prior to purification using tangential flow filtration (as described previously).

Synthesis of Layer-by-Layer Nanoparticles

Liposomes and PLGA nanoparticles were layered by adding an equal volume of nanoparticle solution (not exceeding 1 mg/mL) to an equal volume of polyelectrolyte solution under sonication at room temperature. The mixture was sonicated for roughly 3 seconds. The optimal weight equivalent (wt. eq.) for each layer was determined through a polyelectrolyte titration using 50 uL samples of the nanoparticle for each tested wt. eq. Each test ratio was layered as described above and then characterized. If the resulting particle had a zeta potential greater than 30 mV or less than −30 mV, and an acceptable size, it was chosen as the optimal wt. eq. for each layer. The wt. eqs. of the cationic first layer, PLR, were 0.3 for the liposome core and 0.4 for the PLGA core. For the anionic second layer, the same weight equivalents of polyelectrolyte were used for both the liposome and PLGA core. The weight equivalent of each polyelectrolyte layer are as follows: 0.65 wt. eq. PLD, 0.65 wt. eq. PLE, 1.2 wt. eq. HA, 0.65 wt. eq. dextran sulfate, 1.2 wt. eq. fucoidan, 1.2 wt. eq. alginate, 0.2 wt. eq. PAA, and 1.2 wt. eq. chondroitin sulfate. Polyelectrolyte solutions for liposome layering, except for HA and alginate, were prepared in 50 mM HEPES and 40 mM NaCl (pH 7.4) which was diluted to 25 mM HEPES and 20 mM NaCl upon 1:1 mixing with the nanoparticle substrate in water. HA and alginate stocks were prepared in 10 mM HEPES which was diluted to 5 mM HEPES upon mixing with the nanoparticle substrate in water. All polyelectrolyte solutions for PLGA nanoparticle layering were prepared in water. Layered particles were incubated at room temperature for one hour before being purified via TFF and characterized.

Synthesis of PEG-PLGA Nanoparticles

PEG-PLGA (50:50, 10k PLGA, 2k PEG) was dissolved at a concentration of 10 mg/mL in a 1:1 ratio of acetone to DMSO and cyanine5 free acid dye was dissolved at a concentration of 50 mg/mL in DMSO. 6 mL of milliQ water was added to a 20 mL scintillation vial and stirred gently on a plate. In a 2 mL Eppendorf tube, 1 μL of the dye was added to 0.5 mL of the PEG-PLGA solution, mixed and drawn into syringe with a 27-gauge needle attached. In the scintillation vial, the tip of the needle was submerged below the water line and the PEG-PLGA-cyanine5 solution was slowly added to the water under constant stirring. The solution was let stir ~3 hours to allow for solvent evaporation. An additional 2 mL milliQ water were added the solution prior to purification via TFF and characterization.

PEGylation of Carboxylated Polystyrene Nanoparticles 20, 100 and 200 nm yellow green carboxylated fluospheres were prepared at stocks of 2% solids and 40 nm yellow green carboxylated fluospheres were prepared at a stock of 5% solids. A 5 mg/mL stock of 3k PEG-$NH_3Cl$ was prepared in DPBS and a 15 mg/mL stock of EDC was prepared in PBS. For the 20, 100 and 200 nm fluospheres, 200 µLs of 3k PEG-$NH_3Cl$ and 100 µLs of each fluospheres were combined and mixed in separate 1.5 mL Eppendorf tubes. For the 40 nm fluosphere, 200 uLs of 3k PEG-$NH_3Cl$ and 40 uLs of fluospheres were combined and mixed in a 1.5 mL Eppendorf tube. To each Eppendorf tube, 200 µL of the EDC solution was added. All reactions were carried out a room temperature and protected from light for 6-8 hours while mixing.

Fluorescently Tagging Antibodies

The cetuximab antibody was prepared in 0.1M sodium bicarbonate (pH 8.2) at a concentration of 0.5 mg/mL and the isotype IgG antibody was prepared in water at 2 mg/mL. SulfoCy5 NHS ester dye was prepared in DMSO at a concentration of 50 mg/mL. 200 µL of the cetuximab antibody was added to a protein lobind tube. In a separate protein lobind tube, 50 µL of the IgG antibody was added with 150 µL of 0.1M sodium bicarbonate (pH 8.4). To each solution, 1 µL of sulfoCy5 NHS ester dye was added. Both reactions were carried out a room temperature and protected from light for 6-8 hours while mixing. To purify the antibodies, a 3k MWCO spin column was used. Each antibody was washed 15 times to purify.

Conjugation of Antibodies to Nanoparticles

EDC and sulfoNHS stocks were prepared at 10 mg/mL in water. Isotype IgG and cetuximab antibodies were prepared at 0.2 mg/mL in PBS. 25% PEG liposomes (LIPO-25% PEG) were prepared at 1 mg/mL in water. 1 mL of nanoparticle was added to two separate protein lobind tubes. To each tube, 8 uL of EDC and 16 uL of sulfoNHS was added. Each tube was mixed at room temperature and protected from light for 30 minutes. 0.5 mL of isotype IgG was added to one lobind tube and 0.5 mL of cetuximab was added to the other lobind tube. Each reaction was mixed at room temperature and protected from light for 1 hour. After an hour, tangential flow filtration was used for purification and nanoparticles were characterized via DLS.

Synthesis of Solid Lipid Nanoparticles (LNPs)

GFP mRNA was dissolved in sodium acetate buffer (25 mM, pH 2.5) in a glass vial equipped with a stir bar and lipids (cationic lipid: 5 mg/mL, PEG lipid: 1 mg/mL, phospholipids: 5 mg/mL, cholesterol: 4 mg/mL) were separately dissolved in ethanol at a constant molar ratio. See table 5 for specific ratios. The mRNA solution was stirred at 700 rpm and the lipid mixture was added under stirring. After stirring for 10 seconds, the solution was let rest for 5 minutes. After this, the solution was diluted 1:1 with RNAase-free water. Resulting LNPs were purified via ultracentrifugation and stored at 4° C. mRNA encapsulation was quantified using the commercially available RiboGreen assay.

TABLE 6

Characterization of LNPs 1 and 2 detailed in table 5.

| | Z-average (nm) | PDI | Zeta Potential (mv) | mRNA encapsulation (%) |
|---|---|---|---|---|
| LNP1 | 100.5 ± 3.0 | 0.125 ± 0.054 | 18.2 + 2.9 | 91 |
| LNP2 | 112.8 ± 1.0 | 0.216 ± 0.027 | 35.2 + 1.7 | 92 |

Characterization of Nanoparticles

Nanoparticle hydrodynamic size and polydispersity were measured using dynamic light scattering (Malvern ZS90 Particle Analyzer). Zeta measurements were also acquired with the Malvern ZS90 using laser doppler electrophoresis. Nanoparticle solutions were diluted in milliQ water in polystyrene, semi-micro cuvettes for size measurements and DTS1070 folded capillary cuvettes for zeta measurements. For LIPO-5% PEG, LIPO-25% PEG, LIPO-5% PEG*, LIPO-EGFR and LIPO-IgG, the hydrodynamic size for each nanoparticle was measured using high throughput dynamic light scattering (Wyatt Dyna Pro Plate Reader) with samples diluted in milliQ water and tested in a black, glass bottom 384 well plate.

Pooled PRISM Cell Dosing with NPs and Preparation for Flow Cytometry

Cells were seeded at 200,000 cells/well in 0.5 mL RPMI-1640 media supplemented with 10% FBS in a 12-well plate. Cells were allowed to grow for 24 hours prior to treatment with nanoparticles. Prior to dosing, all PLGA nanoparticle formulations were normalized to a concentration of 50 µg/mL and all other nanoparticle formulations were normalized to a concentration of 100 µg/mL. Cells were dosed with 50 µL of normalized PLGA nanoparticles and 25 µL of normalized nanoparticles for all other formulations. Cells and nanoparticles were incubated for either 4 or 24 hours at 37° C. and 5% $CO_2$.

After incubation, cells were washed once with 500 µL of warm PBS and dissociated with 150 µL 0.25% Trypsin-EDTA. After 5 minutes at 37° C., the trypsin was quenched with 200 µL of media and the cells were triturated vigorously to ensure that all cells had been dissociated from the plate. Cells were then transferred to a fluorescence-activated cell sorting (FACS) tube through a cell strainer cap and placed on ice until sorted.

Pooled PRISM Cell Dosing with Antibodies 10 wells of cells were washed twice with 200 µL of room temperature PBS and dissociated with 200 µL of accutase by incubating at 37° C. for 5 mins. After incubation, 300 µL of cold FACS buffer (PBS+2% FBS) was added to each well and the cells were triturated. Each well was transferred and combined in a 15 mL falcon tube and spun at 1000 rpm for 5 minutes at 4° C. After spinning, the supernatant was removed and the cells were counted and resuspended in FACS buffer at a concentration of 1e6 cells/mL. 200 µLs of the cell suspension was transferred to 12 separate FACS tubes. To three of the tubes, nothing was added to remain as an untreated control. To three tubes, 15 µL of 0.1 mg/mL Cy5-cetuximab was added. To three tubes, 15 µL of 0.1 mg/mL Cy5-IgG was added. To the final three tubes, 5 µL of EGFR-AF488 (used at undiluted stock concentration provided by manufacturer) were added. All tubes were vortexed gently and incubated in the dark at 4° C. for one hour. After an hour, 200 µL of cold FACS buffer was added to each tube, the cells were triturated and then spun at 1000 rpm for 5 minutes at 4° C. After centrifugation, the supernatant was removed and the cells were resuspended in 300 µL of cold FACS buffer. The cells were stored on ice until flow sorting.

Preparation of Untreated and Sorting Control Samples

Cells were washed once with warm PBS. For cells that were lysed in well, 150 µL of lysis buffer was added to each well and cells were incubated for 5 minutes at 37° C. After incubation, 100 µL of PBS was added and the lysed cells were triturated and transferred to an Eppendorf tube. For trypsinized cells, after a PBS wash, 150 µL 0.25% Trypsin-EDTA was added to the wells and incubated for 5 minutes at 37° C. To quench the trypsin, 200 µL of media was added to the well and the cells were triturated and transferred to either a FACS tube (for sorted control) or Eppendorf tube (for unsorted control). The unsorted control cells were pelleted by centrifuging at 1000 rpm for 5 minutes and resuspended directly into 150 µL of lysis buffer.

Flow Cytometry and FACS Information

For FACS, samples were sorted using a BD Cell Sorter (BD Biosciences). Samples dosed with Cy5 nanoparticles or Cy5 antibodies were sorted on the APC channel (ex. 640, filters 660/20). Samples dosed with yellow green fluospheres or AF-488 antibodies were sorted on the GFP channel (ex. 488, filters 530/30).

For all flow analysis in validation studies, samples were analyzed using a BD Flow Cytometer with high throughput sampler (BD Biosciences). Samples dosed with Cy5 nanoparticles were analyzed on the APC channel (ex. 640, filters 670/30). Samples dosed with yellow green fluospheres were analyzed on the GFP channel (ex. 488, filters 515/20). Data was analyzed using FlowJo™ (version 10), and cells were gated for single cells based on an untreated, parental cell line for each condition using the side scatter and forward scatter plots; singlet gates were applied to all samples of the same parental cell line. Analysis of NP intensity was based on a single color (APC or GFP, as above) without compensation.

PRISMseq

Samples lysed in DNA Lysis Buffer (20 mM Tris-HCl (pH 8.4), 50 mM KCl, 0.45% NP-40, 0.45% Tween-20, 10% Proteinase K) were denatured at 95° C. and amplified with a 2×KAPA polymerase master mix. Custom primers (IDT) allowed samples to be dual-indexed for multiplexed Illumina sequencing by directly adding Illumina flow-cell binding sequences to the amplicon:

```
forward primer:
                          (SEQ ID NO: 3)
5'AATGATACGGCGACCACCGAGATCTACANNNNNNNNN

AAGGTGCTTCTCGATCTGCAT reverse primer:
                          (SEQ ID NO: 4)
5'CAAGCAGAAGACGGCATACGAGATNNNNNNNNNGTGA

CTGGAGTTCAGACGTGTGCT,
``` where N represents the indexing nucleotides. Resulting products were quality control checked for single-band amplification using gel electrophoresis and then pooled and purified for sequencing using the Zymo DNA Clean & Concentrator kit. After pooling, the PCR product was quantified using a Fluorometer. Samples were sequenced using Illumina technology. Samples were loaded onto the flow cell at a final concentration of 10 pM with a 20% PhiX spike-in due to low diversity. Sequencing was run for 50 cycles, single-read.

SLC46A3 Validation Studies

Non Pooled Screening

HCC1143 (RPMI-1640), HCC1395 (RPMI-1640), HeLa (RPMI-1640), SW948 (RPMI-1640), LOXIMVI (RPMI-1640), SJSA-1 (RPMI-1640), MCF7 (Eagle's Minimum Essential Medium, EMEM), DAOY (EMEM), MDA-MB-231 (Dulbecco's Modified Eagle's Medium, DMEM), CAOV3 (DMEM), T47D (RPMI-1640), and HepG2 (DMEM) cells were seeded individually at 10,000 cells/well in 100µL of media, supplemented with 10% FBS and 1× Penicillin-Streptomycin. Base media are provided in parentheses following cell line names. Cells were allowed to grow overnight prior to treatment with nanoparticles. Prior to dosing, all nanoparticle formulations were normalized to a concentration of 50 µg/mL. Cells were dosed with 10µL of normalized nanoparticles. Cells and nanoparticles were incubated for either 4 or 24 hours at 37° C. and 5% CO2.

After incubation, cells were washed once with 100µL of warm PBS and dissociated with 20 µL 0.25% Trypsin-EDTA. After 5 minutes at 37° C., the trypsin was quenched with 180µL of media and the cells were triturated vigorously to ensure that all cells had been dissociated from the plate. Cells were placed on ice until analyzed using high throughput sampler.

SLC46A3 Overexpression: Viral Transfection of LOXIMVI Cells

Lentiviral vectors were purchased from the Broad Institute's Genetic Perturbation Platform (GPP), specifically ccsbBroad304_09945 (SLC46A3) and ccsbBroad304_99991 (Luciferase, vector control).

LOXIMVI cells were grown and passaged in RPMI-1640 supplemented with 10% FBS and 1× Pen/Strep until ready for infection. LOXIMVI cells were trypsinized, counted and resuspended to a concentration of $1.36 \times 10^6$ cells/mL. A solution of 2× polybrene was added to the cell suspension such that the final concentration of polybrene was 8 µg/mL. Cells were seeded into two six-well plates at 750,000 cells/well. Lentiviral vectors were separately added to plates at six different doses: 0, 25, 50, 100, 200, and 400 µLs. After, 1 mL of media was added to each well and the cells were incubated overnight at 37° C. and 5% $CO_2$ and media changed at 17 hours post-seeding. At 48 hours after seeding, the cells were re-seeded at 375,000 cells/well in 2 mLs of blasticidin containing media (final blasticidin concentration was 1 µg/mL). The selection progress was monitored via flow cytometry (FIG. 8).

SLC46A3 Knock-Out Via CRISPR-Cas9 in T47D Cells

SLC46A3 knock-out T47D cell lines were generated by infection with lentiCRISPRv2-Opti (Addgene #163126) vectors encoding Cas9 and single guide RNAs (sgRNAs).[51] The following oligonucleotides were used for sgRNA cloning and include cloning overhangs for ligation after BsmBI digest of lentiCRISPRv2-Opti vector:

```
sgGFP_F:
                          (SEQ ID NO: 5)
caccGGGCGAGGAGCTGTTCACCG sgGFP_R:
                          (SEQ ID NO: 6)
aaacCGGTGAACAGCTCCTCGCCC sgSLC46A3_F:
                          (SEQ ID NO: 7)
caccgAAAGCAAGCTCCCCAAAATG sgSLC46A3_R:
                          (SEQ ID NO: 8)
aaacCATTTTGGGGAGCTTGCTTTc
```

Clonal knock-out cell lines were isolated through fluorescence-activated cell sorting, and biallelic frame-shifts were confirmed by deep-sequencing (allele 1: −32 bp frameshift 501 reads; allele 2: −10 bp frameshift; 477 reads). The T47D SLC46A3 knock-out line described has the mutant alleles c.442_453del and c.440_449del.

Quantification of SLC46A3 protein expression via western blot was not possible due to the lack of commercially available antibodies with proper specificity. In addition to our own experimental conclusions, this point has also been referenced in the literature.[48]

SLC46A3 Knockdown Via siRNA in T47D Cells

T47D cells were plated in a 96 well plate at 8,000 cells per well and let grow for 24 hours. Then, siRNA (Silencer Select s49280) against SLC46A3 and a non-targeting, scramble control (siScramble) were dosed using a commercially available transfection kit and protocol. After 24 hours, Cy5 labeled LIPO-0.3% PEG was added at the same concentration and amount noted above and incubated for an additional 24 hours prior to flow cytometry assessment of NP-cell association.

For PCR profiling, T47D cells were plated in a 6 well plate at 400,000 cells per well and let grow for 24 hours. Then, Then, siRNA (Silencer Select s49280) against SLC46A3 and a non-targeting, scramble control (siScramble) were dosed using a commercially available transfection kit and protocol. Knockdown was assessed both 24 and 48 hours post transfection via PCR.

Quantitative Real-Time PCR for SLC46A3 Transcript Levels

Total RNA was prepared from the indicated cell lines using a kit from Qiagen. cDNA synthesis was performed using the Invitrogen SuperScript™ VILO system (ThermoFisher Scientific) according to the manufacturer's instructions prior to quantitative real-time PCR with the Applied Biosystems PowerUP™ SYBR Green master mix (ThermoFisher Scientific) using an Applied Biosystems QuantStudio™ 6 instrument in fast mode. Quantitation of transcript abundance was calculated from standard curves and normalized to 18S rRNA. The following oligonucleotides were used for real-time PCR:

```
SLC46A3_F:
                                (SEQ ID NO: 9)
tgccattctctgttctacgg SLC46A3_R:
                                (SEQ ID NO: 10)
tgcagtgactcctccaagtg 18S rRNA_F:
                                (SEQ ID NO: 11)
agacaaatcgctccaccaac 18S rRNA_R:
                                (SEQ ID NO: 12)
cctgcggcttaatttgactc
```

Imaging Cytometry Sample Preparation

Engineered T47D and LOXIMVI cells were plated in T25 flasks in 5 mL of media at the following densities: 2.3-2.6× $10^6$ cells/flask for LOXIMVI-vector control, LOXIMVI-SLC46A3 OE, and T47D-vector control cells; 3.8×$10^6$ cells/flask for T47D-SLC46A3 knockout cells. Cells were allowed to adhere for 24 h (37° C., 5% $CO_2$) prior to treatment with 250 µL NP solutions, ranging from 0.05-0.1 mg/mL core concentration, for 24 h.

For CellTracker™/LysoTracker™ staining, the following staining solutions were prepared: 50 nM LysoTracker™ Green and/or 50 µM CellTracker™ Orange CMRA in serum-free RPMI-1640. CellTracker™ and LysoTracker™ concentrations were selected based on manufacturer recommendations as well as literature protocol[52].

Cells were trypsinized and transferred to 15 mL falcon tubes prior to washing 2× with warmed PBS. Between washes, cells were pelleted at 300 rcf for 5 min. For CellTracker™ and LysoTracker™ staining, cells were re-suspended in 0.5 mL respective staining solution, and incubated in the dark at 37° C. for 60 min. Cells were then pelleted and washed 2× with warmed PBS.

For fixation, cell pellets were re-suspended in 2% formaldehyde in PBS, incubated on ice for 20 min, then washed 2× with PBS. Cell pellets were then re-suspended in Hoechst-3342 (1 µg/mL in PBS) for 2 min prior to washing 2× with PBS. Cells were re-suspended and stored in 2% FBS in PBS overnight prior to running samples on ImageStream.

Samples were run on an ImageStreamX™ Mark II(Luminex). Single color controls were prepared using the above protocol for compensation. For analysis, only the Cy5 (NP) and brightfield channels were used.

Imaging Cytometry Analysis Workflow

Data analysis was carried out using AMNIS IDEAS™ software (version 6.2). First, singlet cells were gated based upon scatter plots using brightfield images (Ch01), with aspect ratio intensity on the y-axis and cell area on the x-axis; the same gate was used for all samples. Using the built-in software functionality, the brightfield mask with a 5% erosion was applied to all singlet cells, and a cellular distribution score was generated using the built-in 'Internalization' function in the IDEAS software. Raw data was exported from IDEAS as '.fcs' files, and data was FlowJo™ software was used to visualize the data and compute metrics such as median intensity and median cellular distribution scores.

Deconvolution Optical Microscopy

Chambered cover glass was coated with rat tail collagen (Corning, 3004 of 50 Kg/mL in 0.02N acetic acid). After 5 minutes, the wells were washed with room temperature PBS and allowed to dry in a sterile environment. Wells were stored at 4° C. up to one week prior to seeding cells in 3004 media at the following densities: 5,000 cells/well for T47D-vector control cells, LOXIMVI-vector control and SLC46A3 OE cells; 5,500 cells/well for T47D-SLC46A3 KO cells. The cells were allowed to adhere for 24 h (37° C., 5% $CO_2$) prior to treatment with 154 of a 0.1 mg/mL NP solution (Cy5 channel) for either 4 or 24 h. Then, cells were washed 3× with warm PBS before adding LysoTracker™ Green (130 nM final concentration)+CellTracker™ Blue CMAC (13 µM final concentration) solution, which was prepared right before use in phenol red-free RPMI 1640. Cells were incubated in the dark at 37° C., 5% $CO_2$ for 45 min prior to aspirating dye solution, washing 3× with warm PBS, and adding 3004 phenol red-free RPMI 1640 to each well. The cells were imaged with the Applied Precision DeltaVision™ Ultimate Focus Microscope with TIRF Module (Inverted Olympus X71 microscope) equipped with 405, 488, 512, and 568 nm lasers. Images were acquired with a either a 60× (with enhanced magnification) or 100× objective. All images were acquired with OMX softWoRx™ software (Applied Precison/GE). Image LUTs were linearly adjusted to improve contrast using FIJI. Z slices were merged into Z projections as shown in FIGS. 3G-H and 8. For CellTracker™ signal, a single (bottom most) slice was interleaved with the Z projection of the NP and LysoTracker™ signal.

Animal Studies

All animal experiments were approved by the Massachusetts Institute of Technology Committee on Animal Care (CAC) and were conducted under the oversight of the Division of Comparative Medicine (DCM). Flank tumors of LOXIMVI-vector control and LOXIMVI-SLC46A3 OE cells were established with a subcutaneous injection of 0.5-1.0×$10^6$ cells as a 1:1 mixture with MatriGel™ (Corning) and PBS to the right flank of NCr nude mice.

Nanoparticle Formulation

Cy5 labeled NPs (1 mg/mL, LIPO-0.3% PEG*) were formulated in 5% dextrose (sterilized by filtering through a 0.2 µM filter).

Intratumoral Injection Studies

For intratumoral (IT) studies, within genders, mice with established flank tumors were randomly assigned to either the 4 or 24 h dosing cohort (n=10; for 4 hour time point n=5 female+5 male mice, for 24 hour time point, n=6 female+4 male mice/cohort). Four or 24 hours after injection, mice were imaged using the In Vivo Imaging System (IVIS) Spectrum whole animal imaging device (PerkinElmer) using ex=640/em=700 nm to capture Cy5 signal. Immediately following imaging, mice were humanely euthanized and tumors were excised and imaged again via IVIS. Tumors were then placed into pre-weighed tubes containing 1 mL PBS. Tumors were weighed and their weights recorded for normalization of tumor fluorescence by tumor mass.

Tumor tissue was embedded in OCT™ compound (Tissue-Tek) and frozen over dry ice prior to sectioning. Sectioning and hematoxylin and eosin (H&E) staining was performed by Koch Institute's histology core facility.

To confirm animal gender did not confound our findings, using data obtained from the IT study, we compared the total radiant efficiency divided by tumor mass (mg) of male and female mice at both the 4 and 24 h time points, and we did not find a statistically significant difference in NP tumor accumulation (p>0.05).

Intravenous Injection Studies

For intravenous (IV) studies, n=10 for the SLC46A3 overexpressing group (n=5 female+5 male mice) and n=9 for the vector control group (n=5 female+5 male mice). Nanoparticles were administered to mice using tail vein injections (3 total, spaced 24 hour apart). Four hours after the third and final injection, mice were humanely euthanized and tumors were excised and imaged using the In Vivo Imaging System Lumina whole animal imaging device (PerkinElmer) to capture Cy5 signal (ex=620/em=670 nm). Tumors were then placed into pre-weighed tubes containing 1 mL PBS. Tumors were weighed and their weights recorded for normalization of tumor fluorescence by tumor mass.

Statistical Analysis

Methods pertaining to nanoPRISM analysis are detailed in Supplementary Text, below. All statistical analysis for non-pooled validation studies was performed using GraphPad PRISM 9. For single comparisons (non-parametric), the Mann-Whitney test was used. For multiple comparison testing, the Kruskall-Wallis test was used to compare treatment groups to the parental control.

Supplementary Text nanoPRISM Probabilistic Model Development

In the statistical analysis of the sequencing data, a simple probabilistic model is employed to infer each cell's probability from a given cell line to fall into the predefined bins after treating with a given NP formulation. In particular, for each NP treatment, the observed count for cell line. and bin j and technical replicate k is denoted with $x_{i,j,k}$, and standard Poisson model for sequencing noise is assumed, i.e. $x_{i,j,k} \sim \text{Pois}(\mu_{i,j,k})$.

Furthermore, the expected value of this random variable, $\mu_{i,j,k}$, is factored into three operational quantities $\mu_{i,j,k} = \lambda_{j,k} S_i P_{i,j}$, where $\lambda_{j,k}$ is a sample-specific scaling factor to take into the sequencing and PCR efficiency into account. $S_i$ is the initial abundance of line before the treatment, and $P_{i,j}$ is the probability of each cell to fall into bin j.

In this formulation, we denote the control samples (not sorted into the bins) with a dummy binj=0 and $P_{i,0}=1$ for all i, and maximize the likelihood function $$L = \sum_{i,j,k} x_{i,j,k} \log(S_i P_{i,j} \lambda_{j,k}) - S_i P_{i,j} \lambda_{j,k} - \log(x_{i,j,k}!)$$

subject to the constraints $P_{i,A}+P_{i,B}+P_{i,C}+P_{i,D}=1$, $S_i>0$, $\lambda_{j,k}>0$, $P_{i,k} \geq 0$, for all i, j, k, using a standard projected gradient descent algorithm to infer the binning probabilities $P_{i,k}$ independently for each biological sample and their concordance across replicates are used as a QC check. The R scripts used to process the data and infer the binning probabilities are available upon request.

Univariate Analysis Description

For each given WA profile and each dataset in the cancer cell line encyclopedia (CCLE), we regressed the WA profile of the NP formulation on each column of the feature dataset and calculated the regression coefficient along with its corresponding standard error under the homogeneity assumption. Next, we applied the adaptive shrinkage method[53] to obtain moderated effect sizes, standard deviations and corresponding q-values. In the figures, the ratio of the posterior effect sizes and the standard deviations are presented as z-scores. This analysis was conducted in R[54] and figures were produced using the package ggplot2[55].

Random Forest Description

For the multivariate biomarker analysis, the weighted average of the binning probabilities scores, W's, are used as the response variable and standard random forest regression models (RF) fitted proceeding a correlation-based feature selection. In particular, we fit two RF models for each NP formulation where the first one, CCLE model, uses a concatenation of the core cell line characteristics (mRNA expression, mutation status, copy number changes, and lineage annotations), while the second one, ALL, includes more features (proteomics, CRISPR knock-outs, micro RNA, metabolomics) by limiting the analysis on the overlapping cell lines across all the datasets. For each model, 10-fold cross-validation is employed while in each fold an RF model fit after choosing the most correlated 500 features to the response variable). The cross-validated predictions then used to calculate Pearson scores (the correlation between the observed and predicted responses), and $R^2$ values to assess the model performance. As the final step, these values are reported along with the default feature importances.

Principal Component Analysis and K-Means Clustering

Principal component analysis (PCA) was performed using the weighted average of each nanoparticle-cell line pair from the by collapsing data by nanoparticle or cell-line. K-means clustering was performed on a subset of biomarkers generated by RF method that met the following criteria: CCLE features including gene expression, gene copy number, or protein abundance; univariate analysis z-score greater than 0. The Pearson correlation for biomarkers was then input for k-means clustering to generate 5 clusters. These analyses were conducted in R using ggfortify[56,57] to perform PCA or k-means clustering and figures were produced using the package ggplot2[55].

We claim:

1. A method of identifying a subject who is susceptible to treatment for cancer with lipid-based nanoparticle therapies, the method comprising determining expression levels of solute carrier family 46 member 3 (SLC46A3) in a plurality of cancer cells from a subject having cancer, wherein a subject with decreased SLC46A3 expression levels as compared to a control is susceptible to treatment with lipid-based nanoparticles, wherein the control is selected from the group consisting of (i) a reference range of expression levels from control cells expressing SLC46A3, (ii) a contemporaneous measurement of SLC46A3 expression in control cells known to express SLC46A3, (iii) a cohort of controls profiled and publicly available through a publicly available database, (iv) a reference level determined for a particular cancer type or subtype, and (v) a reference level determined from an individual patient from an earlier timepoint; and
  wherein the method further comprises administering to a subject identified as susceptible to treatment with lipid-based nanoparticle therapies or identified as having cancer cells susceptible to treatment with nanoparticles, an amount of a lipid-based cancer therapy nanoparticle effective to treat or diagnose cancer.

2. The method of claim 1, wherein the SLC46A3 expression level of the subject is increased or unchanged after the administering, wherein the method further comprises administering to the subject a non-lipid cancer therapy nanoparticle to treat or diagnose the cancer.

3. The method of claim 1, wherein the SLC46A3 expression level of the subject is increased or unchanged after the administering, wherein the method further comprises administering to the subject an increased dosage or total amount of the lipid-based cancer nanoparticle to treat or diagnose the cancer.

4. The method of claim 1, wherein the lipid-based nanoparticle comprises a liposomal nanoparticle.

5. The method of claim 4, wherein the liposomal nanoparticle comprises an anionic liposomal nanoparticle.

6. The method of claim 5, wherein the anionic liposomal nanoparticle comprises an electrostatic coating.

7. The method of claim 6, wherein the electrostatic coating comprises one or more polyanions selected from the group consisting of polyacrylic acid (PAA), poly-L-aspartate (PLD), poly-L-glutamate (PLE), hyaluronate (HA), dextran sulfate (DXS), fucoidan (FUC), alginate (ALG), chondroitin sulfate (CS), carboxylate ions, and sulfate ions.

8. The method of claim 1, wherein the lipid-based nanoparticle comprises a solid lipid nanoparticle.

9. The method of claim 8, wherein the solid lipid nanoparticle core comprises an ionizable, neutral, or cationic nanoparticle.

* * * * *